(12) United States Patent
Choi et al.

(10) Patent No.: US 12,404,507 B2
(45) Date of Patent: Sep. 2, 2025

(54) USING MICRORNAS TO CONTROL ACTIVATION STATUS OF HEPATIC STELLATE CELLS AND TO PREVENT FIBROSIS IN PROGRESSIVE LIVER DISEASES

(71) Applicant: THE GENERAL HOSPITAL CORPORATION, Boston, MA (US)

(72) Inventors: Michael Yoonsuk Choi, Boston, MA (US); Byeong-Moo Kim, Wellesley, MA (US)

(73) Assignee: THE GENERAL HOSPITAL CORPORATION

( * ) Notice: Subject to any disclaimer, the term of this patent is extended or adjusted under 35 U.S.C. 154(b) by 1143 days.

(21) Appl. No.: 17/238,612

(22) Filed: Apr. 23, 2021

(65) Prior Publication Data

US 2021/0238604 A1    Aug. 5, 2021

Related U.S. Application Data

(62) Division of application No. 16/302,940, filed as application No. PCT/US2017/033570 on May 19, 2017, now Pat. No. 11,015,196.

(60) Provisional application No. 62/339,431, filed on May 20, 2016.

(51) Int. Cl.
  *C12N 15/113* (2010.01)
  *A61K 35/407* (2015.01)
  *A61P 1/16* (2006.01)

(52) U.S. Cl.
  CPC .......... *C12N 15/113* (2013.01); *A61K 35/407* (2013.01); *A61P 1/16* (2018.01); *C12N 2310/141* (2013.01); *C12N 2330/50* (2013.01)

(58) Field of Classification Search
  None
  See application file for complete search history.

(56) References Cited

U.S. PATENT DOCUMENTS

| | | | |
|---|---|---|---|
| 8,759,313 B2 * | 6/2014 | Schrum | C12N 15/113 536/24.5 |
| 9,090,878 B2 | 7/2015 | Sancho-Bru et al. | |
| 10,039,735 B2 * | 8/2018 | Jalan | A61K 31/7016 |
| 11,015,196 B2 * | 5/2021 | Choi | A61K 35/407 |
| 2012/0009672 A1 | 1/2012 | Sancho-Bru et al. | |
| 2015/0225719 A1 | 8/2015 | Chen et al. | |
| 2016/0060627 A1 | 3/2016 | Elmen et al. | |

FOREIGN PATENT DOCUMENTS

| | | |
|---|---|---|
| EP | 2829613 A1 | 1/2015 |
| WO | 2016022536 A2 | 2/2016 |

OTHER PUBLICATIONS

Kishnani et al., (Genet Med. Nov. 2014; 16(11):e1, 29 pages) (Year: 2014).*
Mannaerts et al., "Gene expression profiling of early hepatic stellate cell activation reveals a role for Igfbp3 in cell migration", PLoS One 8(12) e84071 (2013).
Taghdouini et al., "In vitro reversion of activated primary human hepatic stellate cells", Fibrogenesis Tissue Repair 8: 14 (2015).
Wang et al., "Hepatitis B viral RNA directly mediates down-regulation of the tumor suppressor microRNA miR-15a/miR-16-1 in hepatocytes", J Biol Chem 288(25) 18484-18493 (2013).

* cited by examiner

*Primary Examiner* — Richard A Schnizer
(74) *Attorney, Agent, or Firm* — NIXON PEABODY LLP; David S. Resnick; Jeanne N. Jodoin

(57) ABSTRACT

Provided herein are methods and compositions for treatment and/or prevention of liver disease. Aspects of the present disclosure relate to the engineering of a quiescent Hepatic Stellate Cell, and use of the engineered quiescent Hepatic Stellate Cell, or population thereof in the treatment and/or prevention of liver disease.

16 Claims, 9 Drawing Sheets

Specification includes a Sequence Listing.

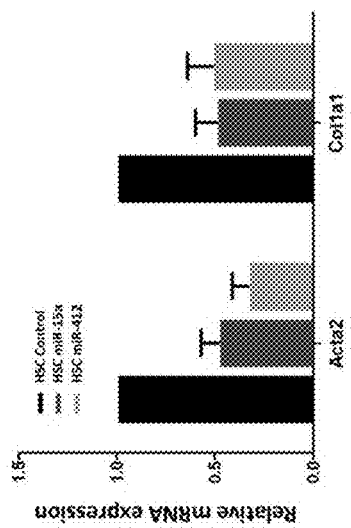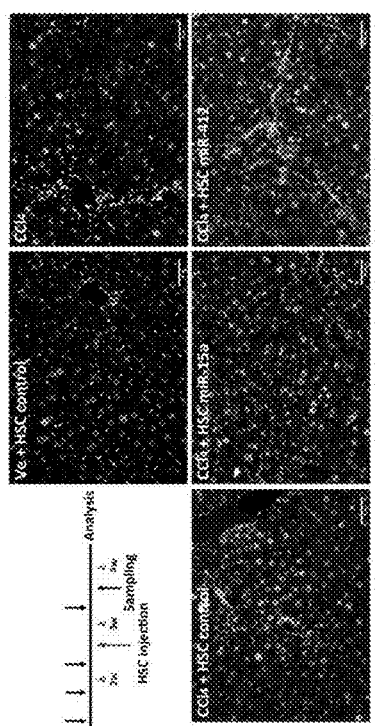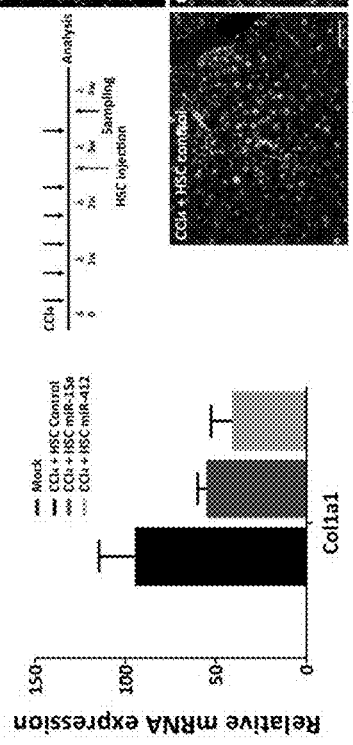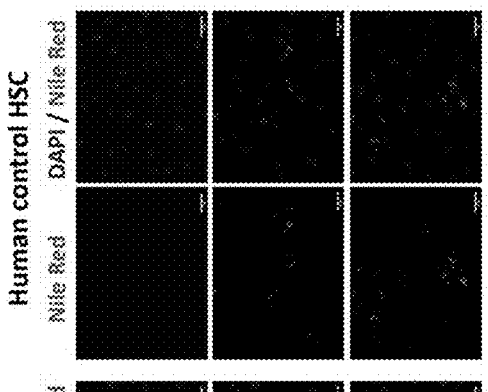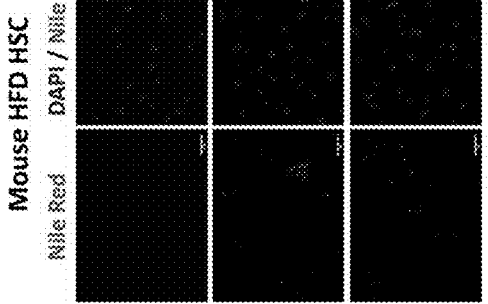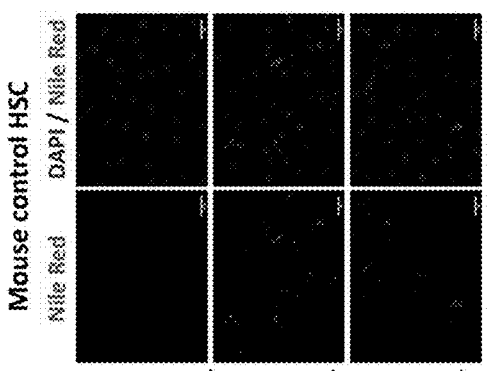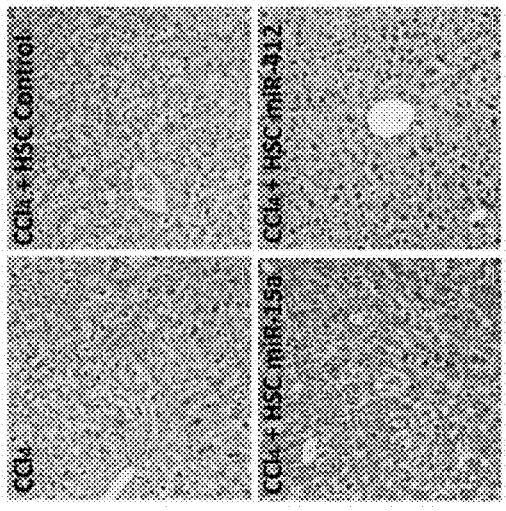

USING MICRORNAS TO CONTROL ACTIVATION STATUS OF HEPATIC STELLATE CELLS AND TO PREVENT FIBROSIS IN PROGRESSIVE LIVER DISEASES

CROSS-REFERENCE TO RELATED APPLICATIONS

This application is a Divisional Application of U.S. Ser. No. 16/302,940, filed Nov. 19, 2018, which is a 35 U.S.C. § 371 National Phase Entry Application of International Application No. PCT/US2017/033570 filed May 19, 2017, which designates the U.S. and claims benefit under 35 U.S.C. § 119(e) of U.S. Provisional Application No. 62/339,431 filed May 20, 2016, the contents of which are incorporated herein by reference in their entireties.

SEQUENCE LISTING

The sequence listing of the present application has been submitted electronically via EFS-Web as an ASCII formatted sequence listing with a file name "Seq_Listing_TXT_030258-089591PCT.txt", creation date of Apr. 19, 2021 and a size of 4,145 bytes. The sequence listing submitted via EFS-Web is part of the specification and is herein incorporated by reference in its entirety.

FIELD OF THE INVENTION

The field of the invention relates to the treatment of liver disease.

BACKGROUND

Non-alcoholic fatty liver disease (NAFLD) is currently the most common hepatic disorder in industrialized nations. Furthermore, it is expected to become the most common cause of end-stage liver disease, hepatic transplant, and hepatocellular carcinoma in the developed world. In the United States, 80 million people are estimated to be affected due to the high prevalence of NAFLD risk factors including obesity, diabetes, and hyperlipidemia. Reducing risk factors for NAFLD is the main mode of management and with no FDA approved drugs for it, the unmet need for treating this common but serious hepatic illness is obvious.

SUMMARY

The methods and compositions described herein are based, in part, on the discovery that quiescent hepatic stellate cells comprise higher levels of miR-412 and/or miR15a expression when compared to an activated hepatic stellate cell. The methods and compositions described herein are also based, in part, on the discovery that inducing quiescence of hepatic stellate cells and/or administering engineered quiescent hepatic stellate cells to a subject can treat liver disease.

Accordingly, described herein are methods and compositions relating to the administration of and/or expression of miR-15a and/or miR-412 for the treatment and/or prevention of liver diseases, such as Non-Alcoholic Fatty Liver Disease (NAFLD). Also provided herein are methods and compositions relating to the generation and administration of "quiescently reprogrammed" hepatic stellate cells (HSCs) for the treatment and/or prevention of liver disease.

Provided herein in one aspect, is a method for treating and/or preventing a liver disease in a subject, the method comprising: administering a first composition comprising miR-412 or a nucleic acid encoding miR-412 to a subject who has, or is suspected of having liver disease, thereby treating the liver disease in the subject.

In one embodiment of this aspect and all other aspects provided herein, the liver disease is selected from the group consisting of: liver fibrosis, α1 anti-trypsin deficiency, autoimmune hepatitis, biliary atresia, cirrhosis, non-alcoholic fatty liver disease, hepatic cancer, hepatic fibrosis, hepatic steatosis (fatty liver disease), galactosemia, gallstones, Gilbert's syndrome, hemochromatosis, lysosomal acid lipase deficiency, primary biliary cholangitis, porphyria, Reye's syndrome, sarcoidosis, toxic hepatitis, type 1 glycogen storage disease, tyrosinemia, viral hepatitis A, viral hepatitis B, viral hepatitis C, and Wilson disease.

In another embodiment of this aspect and all other aspects provided herein, the liver disease is NAFLD or hepatotoxicity.

In another embodiment of this aspect and all other aspects provided herein, the liver disease is one that is associated with liver fibrosis or induces liver fibrosis.

In another embodiment of this aspect and all other aspects provided herein, the composition further comprises miR-15a or a nucleic acid sequence encoding miR-15a.

In another embodiment of this aspect and all other aspects provided herein, the method further comprises a step of administering a second composition comprising miR15a or nucleic acid encoding miR-15a.

In another embodiment of this aspect and all other aspects provided herein, the composition further comprises a pharmaceutically acceptable carrier.

In another embodiment of this aspect and all other aspects provided herein, the method further comprises a step of diagnosing the subject with liver disease, or liver fibrosis.

In another embodiment of this aspect and all other aspects provided herein, the subject is diagnosed with a liver disease or liver fibrosis prior to the administration step.

In another embodiment of this aspect and all other aspects provided herein, the administration is repeated at least once.

In another embodiment of this aspect and all other aspects provided herein, the subject is a mammal.

In another embodiment of this aspect and all other aspects provided herein, the subject is a human.

In another embodiment of this aspect and all other aspects provided herein, the composition is administered via direct injection, intra-hepatic injection, i.v. administration, or parenteral administration.

Another aspect provided herein relates to a method of inducing a quiescent state in a hepatic stellate cell (HSC), the method comprising: contacting a hepatic stellate cell with a composition comprising miR-412 and/or a composition comprising a nucleic acid sequence encoding miR-412 for a time and under conditions that are sufficient to induce quiescence in the HSC cell.

In one embodiment of this aspect and all other aspects provided herein, the method further comprises a composition comprising miR15a or a nucleic acid encoding miR15a.

In another embodiment of this aspect and all other aspects provided herein, the hepatic stellate cell is contacted with a composition comprising miR-412 and miR-15a (or nucleic acid sequences encoding miR-412 and miR-15a) substantially simultaneously.

In another embodiment of this aspect and all other aspects provided herein, expression of alpha smooth actin (Acta2) and/or alpha-1 type I collagen (Colla1) protein levels are decreased in the HSC cell by at least 10% as compared to the expression of Acta2 and/or Col1a1 in an activated HSC, thereby indicating the HSC is quiescent or is induced to be quiescent. In other embodiments, expression of Acta2 and/or Col1a1 is reduced by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or even 100% (below detectable levels using standard laboratory techniques).

In another embodiment of this aspect and all other aspects provided herein, the size and/or number of intracellular lipid droplets of the HSC are increased by at least 10% as compared to the size or number of intracellular lipid droplets in an activated HSC, thereby indicating the HSC is quiescent. In other embodiments, the size and/or number of intracellular lipid droplets of the HSC are increased by at least 20%, at least 30%, at least 40%, at least 50%, at least 60%, at least 70%, at least 80%, at least 90%, at least 95%, at least 99%, at least 1-fold, at least 2-fold, at least 10-fold, at least 100-fold, at least 1000-fold or more. In some embodiments, an activated HSC does not have any intracellular lipid droplets as detected using standard microscopy techniques. As such, a quiescent HSC cell can also be distinguished from an activated one by the mere presence of one or more intracellular lipid droplets as detected using standard microscopy techniques.

In another embodiment of this aspect and all other aspects provided herein, the hepatic stellate cell is a human cell or is derived from a human primary cell or cell line.

Also provided herein, in another aspect, is a method for engineering a quiescent HSC, the method comprising: contacting a HSC cell with at least one quiescence-inducing agent for a time and under conditions that are sufficient to induce quiescence in the HSC, thereby generating an engineered, quiescent HSC. In another aspect, is a method for engineering a quiescent HSC, the method comprising: expressing at least one quiescence-inducing agent in a hepatic stellate cell for a time and under conditions that are sufficient to induce quiescence in the HSC, thereby generating an engineered, quiescent HSC.

In one embodiment of this aspect and all other aspects provided herein, the quiescence-inducing agent comprises miR-412 or a nucleic acid sequence encoding miR-412 and optionally miR-15a or a nucleic acid sequence encoding miR-15a.

In another embodiment of this aspect and all other aspects provided herein, the quiescence-inducing agent is transiently or constitutively expressed in the HSC. In another embodiment of this aspect and all other aspects provided herein, the quiescence-inducing agent is a nucleic acid sequence that is integrated into the genome of the HSC (e.g., substantially permanent expression).

In another embodiment of this aspect and all other aspects provided herein, the method further comprises administering a second quiescence-inducing agent comprising miR15a or a nucleic acid sequence encoding miR15a.

In another embodiment of this aspect and all other aspects provided herein, the nucleic acid sequence encoding miR-412 and/or the nucleic acid sequence encoding miR-15a is/are comprised by a vector.

In another embodiment of this aspect and all other aspects provided herein, the engineered quiescent HSC cell comprises reduced expression levels (e.g., of at least 10%, at least 20%, at least 30%, at least 40%, at least 50%, at least 60%, at least 70%, at least 80%, at least 90%, at least 95%, at least 99%, or even 100% (i.e., absent)) of at least one gene marker of HSC activation as compared to the expression levels of the at least one gene marker in an activated HSC In another embodiment of this aspect and all other aspects provided herein, the at least one gene marker of HSC activation is alpha smooth actin (Acta2) and/or alpha-1 type I collagen (Col1a1).

In another embodiment of this aspect and all other aspects provided herein, the HSC cell is mammalian cell. For example, the HSC cell is a human cell. Autologous or allogeneic HSC cells can be isolated directly from the liver of a subject using methods known to those of skill in the art (e.g., liver biopsy). Alternatively, HSC cells (e.g., human) can be derived from a reprogrammed somatic cell, such as an induced pluripotent stem cell, a cell line, a biopsy sample, a pluripotent stem cell, or an embryonic stem cell. It is also specifically contemplated herein that the HSCs, particularly those used for treatment, are not derived from an embryonic source.

In another embodiment of this aspect and all other aspects provided herein, the HSC is derived from an embryonic stem cell, a pluripotent stem cell, or an induced pluripotent stem cell (iPS cell).

Another aspect provided herein relates to a method for treating and/or preventing a liver disease in a subject in need thereof, the method comprising: administering to a subject having or at risk of having a liver disease, a composition compromising a quiescent HSC cell or a population thereof, thereby treating and/or preventing the liver disease in the subject.

In one embodiment of this aspect and all other aspects provided herein, the quiescent HSC cell or population thereof comprises exogenous expression of a nucleic acid encoding miR-412 and optionally, exogenous expression of a nucleic acid encoding miR-15a.

In another embodiment of this aspect and all other aspects provided herein, the liver disease is selected from the group consisting of: liver fibrosis, α1 anti-trypsin deficiency, autoimmune hepatitis, biliary atresia, cirrhosis, non-alcoholic fatty liver disease, hepatic cancer, hepatic fibrosis, hepatic steatosis (fatty liver disease), galactosemia, gallstones, Gilbert's syndrome, hemochromatosis, lysosomal acid lipase deficiency, primary biliary cholangitis, porphyria, Reye's syndrome, sarcoidosis, toxic hepatitis, type 1 glycogen storage disease, tyrosinemia, viral hepatitis A, viral hepatitis B, viral hepatitis C, and Wilson disease.

In certain embodiments, the liver disease is non-alcoholic fatty liver disease or hepatotoxicity.

In another embodiment of this aspect and all other aspects provided herein, the composition further comprises a pharmaceutically acceptable carrier.

In another embodiment of this aspect and all other aspects provided herein, wherein the method further comprises a step of diagnosing the subject with liver disease prior to administration of the composition.

In another embodiment of this aspect and all other aspects provided herein, administration of the composition is repeated at least once.

Another aspect provided herein relates to a composition comprising a quiescent HSC or a population thereof and a pharmaceutically acceptable carrier.

In another embodiment of this aspect and all other aspects provided herein, the quiescent HSC comprises reduced expression levels of at least one gene marker of HSC activation as compared to the expression levels of the at least one gene marker in an activated HSC. For example, the expression of the at least one gene marker of HSC activation is reduced by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or even 100% (below detectable levels using standard laboratory techniques) as compared to the expression of the at least one gene marker in an activated HSC.

In another embodiment of this aspect and all other aspects provided herein, the at least one gene marker of HSC activation is alpha smooth actin (Acta2) and/or alpha-1 type I collagen (Colla1).

In another embodiment of this aspect and all other aspects provided herein, the HSC is a 10-100 fold smaller in size as compared to the size of an activated HSC.

In another embodiment of this aspect and all other aspects provided herein, the quiescent HSC or population thereof is/are human cell(s).

In another embodiment of this aspect and all other aspects provided herein, the quiescent HSC or population thereof comprises a nucleic acid sequence encoding miR-412 and/or a nucleic acid sequence encoding miR-15a.

In another embodiment of this aspect and all other aspects provided herein, the expression of miR-412 and optionally miR-15a is transient, inducible, constitutive or permanent expression. In one embodiment, a nucleic acid encoding miR-412 and/or a nucleic acid encoding miR-15a is/are integrated into the genome of the HSC.

Another aspect provided herein relates to an engineered hepatic stellate cell and a scaffold. In some embodiments, the scaffold is optionally biodegradable. It will be appreciated by one of skill in the art that the engineered stellate cells can be grown or deposited in or on the scaffold.

BRIEF DESCRIPTION OF THE FIGURES

FIGS. 9A-9G Decreased expression of Colla1 in the liver when CCl4 challenged mice are treated with quiescently reprogrammed HSCs, measured with PCR (FIG. 9A). Data are presented as mean +/−SD. Quiescently reprogrammed HSCs injected into the spleen grafted on to the liver, as evidenced by the liver producing the GFP signal built into the vector driving the miRNA expression (FIG. 9B). Ve+HSC control, olive oil vehicle gavage and injecting control HSC; CCl4, CCl4 gavage only; CCl4+HSC control, CCl4 gavage and injecting HSCs with empty GFP-vector; CCl4+HSC miR-15a, CCl4 gavage and injecting HSCs with miR-15a-GFP-vector; CCl4+HSC miR-412, CCl4 gavage and injecting HSCs with miR-412-GFP-vector. Forced expression of miR-15a or miR-412 in activated HSCs downregulated alpha smooth muscle actin (Acta2) and alpha-1 type I collagen (Colla1) measured with PCR (FIG. 9C). Data are presented as mean +/−SD. Quiescent, reprogrammed HSCs injected into the spleen decreased the level of liver damage measured by hepatocyte ballooning and death (FIG. 9D). CCl4, CCl4 gavage only; CCl4+HSC control, CCl4 gavage and injecting HSCs with empty GFP-vector; CCl4+HSC miR-15a, CCl4 gavage and injecting HSCs with miR-15a-GFP-vector; CCl4+HSC miR-412, CCl4 gavage and injecting HSCs with miR-412-GFP-vector. Delivering a candidate microRNA, miR-15a or miR-412, into activated mouse HSCs causes reappearance of Nile Red stain-positive lipid droplets, resembling quiescent HSCs (FIG. 9E). Similar results are seen with primary HSCs harvested from a mouse model of NASH (choline-deficient, L-amino acid-defined, high-fat diet model) (FIG. 9F) and activated primary human HSCs (FIG. 9G).

DETAILED DESCRIPTION

Figure 1:
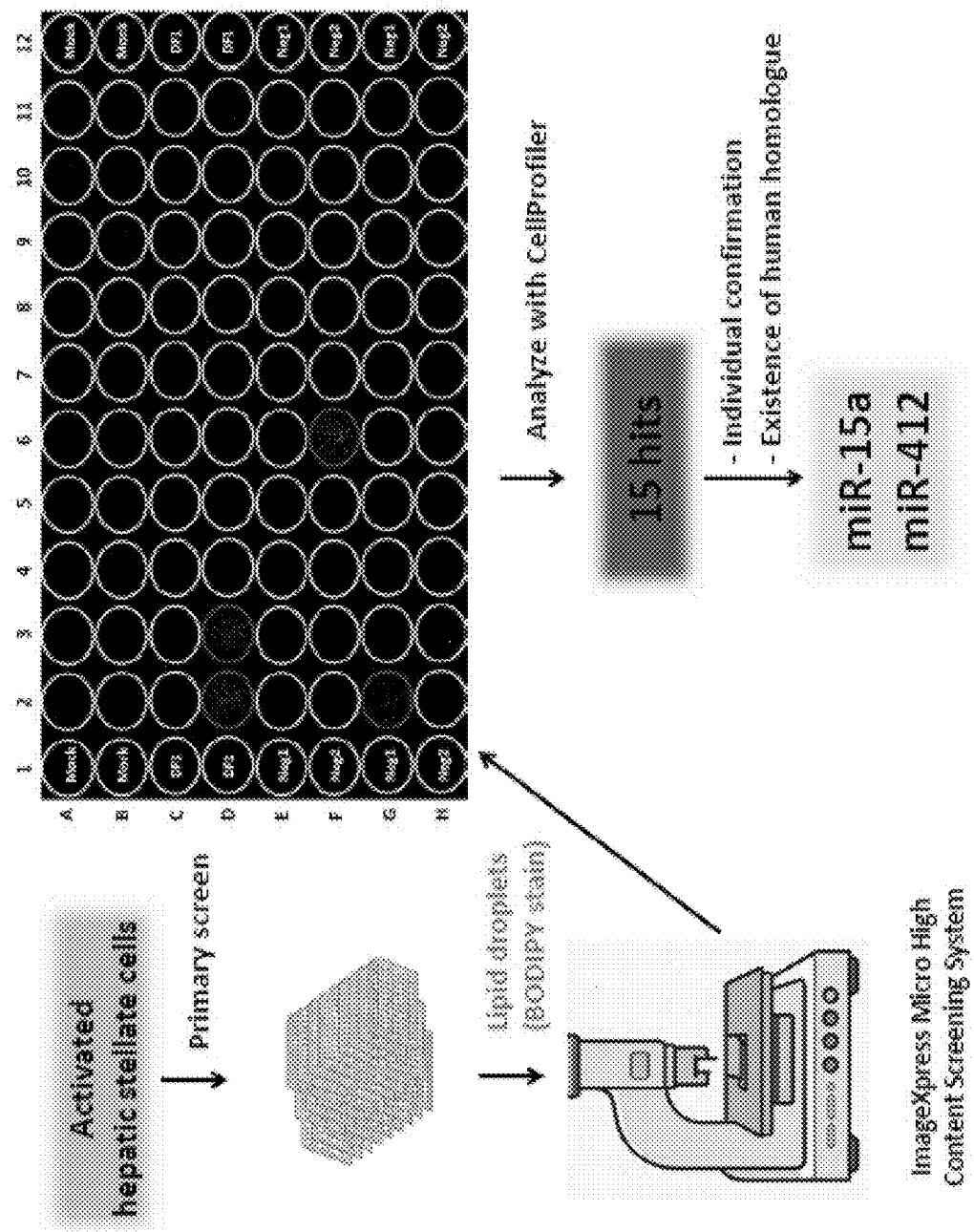
FIG. 1 shows a schematic depicting a full genome microRNA screen for reversion of activated HSCs back to quiescence.
Figure 2:
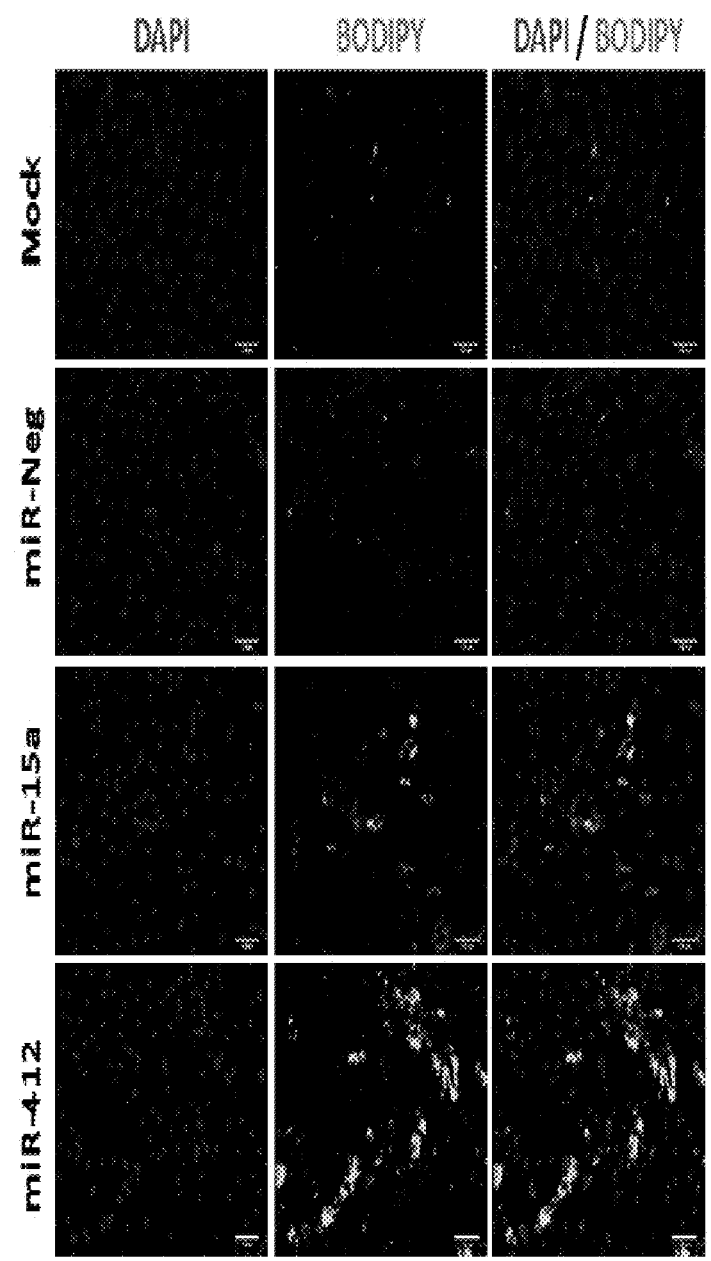
FIG. 2 is a series of micrographs showing that activated HSCs transfected with candidate miRNAs reform retinoic acid positive lipid droplets.
Figure 3:
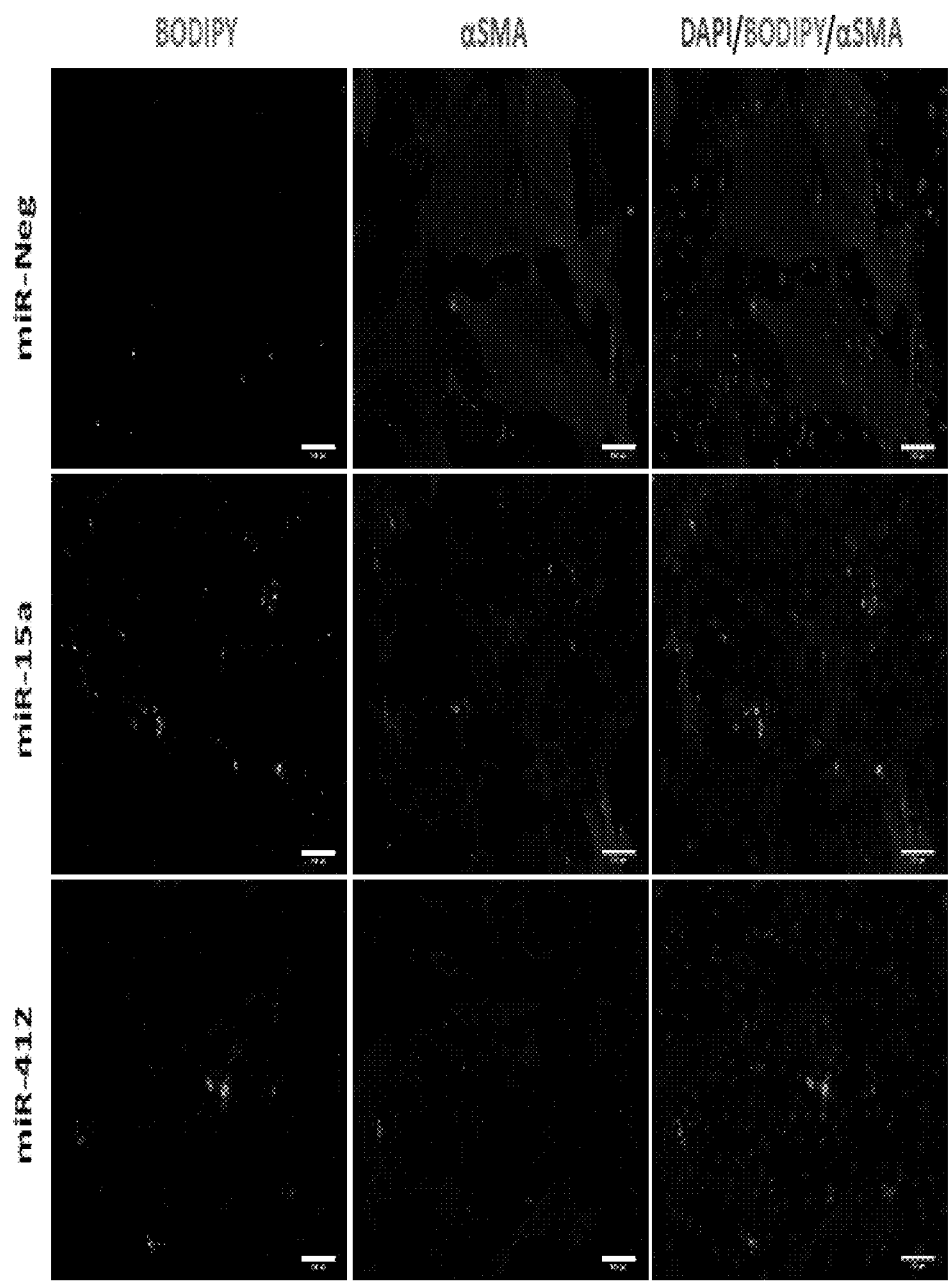
FIG. 3 is a series of micrographs showing that activated HSCs transfected with candidate miRNAs have decreased αSMA expression and increased amounts of lipid droplets.
Figure 4:
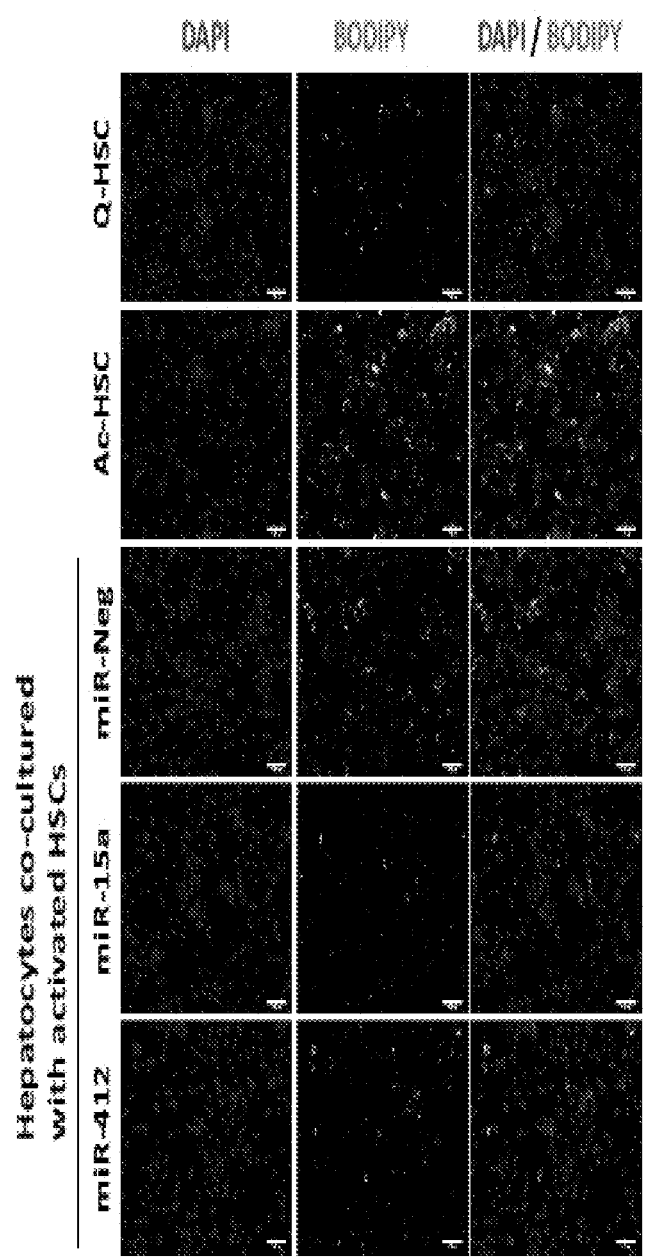
FIG. 4 is a series of micrographs showing that activated HSCs transfected with candidate miRNAs lose the ability to cause steatosis in co-cultured hepatocytes. Lipid is stained with BODIPY-green.
Figure 5:
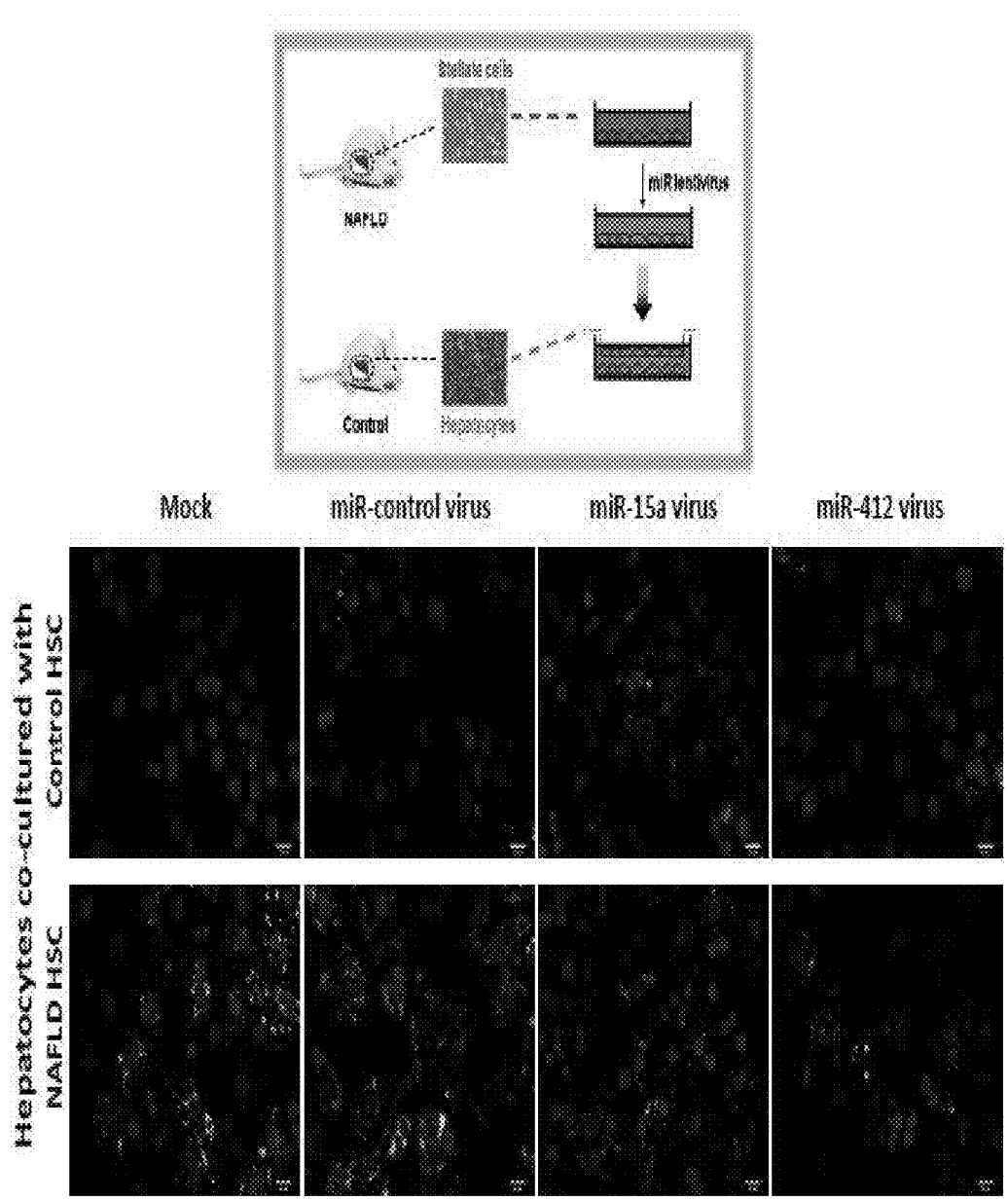
FIG. 5 shows the experimental design and results indicating that NAFLD HSCs infected with candidate miRNA lentivirus lose the ability to cause steatosis in co-cultured hepatocytes. Lipid is stained with BODIPY-green.

Provided herein are methods and compositions comprising microRNAs (e.g., miR-412 and/or miR-15a) or nucleic acid sequences encoding such miRNAs and their use in prevention and/or treatment of liver disease, for example, hepatic fibrotic pathology and/or progressive liver disease. These methods and compositions are based, in part, on the discovery that certain miRNAs can inhibit tissue fibrosis by reverting activated hepatic stellate cells to quiescent hepatic stellate cells.

Definitions

A "subject" or subjects, as that term is used herein includes humans and other primate subjects, such as monkeys and apes for veterinary medicine purposes; however, the technology is also contemplated for use with domestic animals, such as horses, pigs, sheep, cattle, and goats, as well as, companion animals, such as dogs and cats. The technology can also be applied to animals used for research purposes or companionship including guinea pigs, mice, rats, pigs, ferrets etc. The subjects can be male or female and can be of any suitable age, including infant, juvenile, adolescent, adult, and geriatric subjects.

As used herein, the term "quiescent hepatic stellate cell" refers to the phenotype and/or function of a hepatic stellate cell that is substantially similar to the phenotype and/or function of an endogenous hepatic stellate cell from a non-diseased liver. Quiescent stem cells are distinguished from activated hepatic stellate cells by size (e.g., activated stellate cells are 10-100 fold larger in size than quiescent stem cells), morphology (e.g., quiescent HSCs comprise intracellular lipid droplets, while activated HSCs lose such intracellular droplets), collagen secretion (e.g., activated HSCs produce and secrete collagen while quiescent HSCs do not) and function (e.g., quiescent HSCs are associated with appropriate liver function, such as proper maintenance and storage of retinoids etc.; activated HSCs show impaired HSC function). In one embodiment, a quiescent HSC expresses desmin and glial fibrillary acidic protein (GFAP), which is not expressed (or is expressed in very low levels) in activated HSCs.

As will be appreciated by one of skill in the art, there is a spectrum of phenotypes that exist for hepatic stellate cells, with total quiescence of the HSC on one end and complete activation status of the HSC on the other end. In the middle of the spectrum are HSC phenotypes that can be in flux from an activated state towards a quiescent state, or vice versa. That is, intermediate HSCs can include characteristics of both the quiescence status and activated status at the same time and to varying degrees. Such phenotypes can be described herein using terms such as as "induced to a quiescent or activated state," or "entering a quiescent or activated state," or "loss of a quiescent or activated state," and the like.

As used herein, the term "quiescent reprogramming" refers to the process of inducing quiescence (e.g., reversible or permanent) in a hepatic stellate cell for the purpose of maintaining quiescent status of a hepatic stellate cell or reverting the status of an activated hepatic stellate cell to quiescent status. As used herein, the term "quiescently reprogrammed" is used to describe a hepatic stellate cell that has undergone the process of quiescent reprogramming using any method described herein.

As used herein, the term "gene marker of HSC activation" refers to the expression of a gene product (e.g., a protein) at a level that is associated with the activated state of a hepatic stellate cell, for example, activated HSCs comprise increased expression of collagen (e.g., collagen α1 or collagen α1) or collagen-producing enzymes (e.g., Acta2 or Colla1), or increased expression of α-SMA. The presence of such markers, or high/increasing expressions of such markers can indicate that the hepatic stellate cell has or is entering the activated state, thereby losing the characteristics of a quiescent hepatic stellate cell. Alternatively, the absence of such markers or low/decreasing levels of expression can indicate that the hepatic stellate cell is entering the quiescent state or has been quiescently reprogrammed.

As used herein, the term "engineered HSC," and "engineered, quiescent HSC" refers to hepatic stellate cells that express miR-412 and/or miR15a and that display a substantially similar phenotype and/or function of an endogenous quiescent hepatic stellate cell from a non-diseased liver. In some embodiments, the engineered HSC is one that does not or cannot enter an activated state, even under conditions that promote HSC activation. In one embodiment, the engineered HSC is a cell that is maintained in a quiescent state for a desired time. An engineered HSC can comprise transient expression of miR-412 and/or miR-15a, where expression of the miRNAs is lost over a period of time, thereby restoring the phenotype, function etc. of the engineered HSC to those of an unengineered HSC (e.g., an HSC that can be activated). In other embodiments, the engineered HSC can comprise constitutive expression, where expression of miR-412 and/or miR-15a is expressed under all conditions, or can comprise inducible expression, wherein expression of miR-412 and/or miR-15a can be turned on or off by the presence of an inducing or repressive agent. In one embodiment, an engineered HSC is a hepatic stellate cell that comprises "substantially permanent expression" of a nucleic acid encoding miR-412 and/or a nucleic acid encoding miR-15a by integration of such nucleic acids into the genome.

As used herein, the term "quiescence inducing agent" refers to an agent that can modify the cell cycle of a hepatic stem cell, particularly to induce quiescence of an activated hepatic stellate cell.

As used herein the term "stem cell" refers to a cell (e.g., a human cell) that can self-renew and differentiate to at least one cell type. The term "human stem cell" encompasses human stem cell lines, human-derived iPS cells, human embryonic stem cells, human pluripotent cells, human multipotent stem cells or human adult stem cells.

The term "isolated cell" as used herein refers to a cell that has been removed from an organism or population of cells in which it was originally found, or a descendant of such a cell. Optionally the cell has been cultured in vitro, e.g., in the presence of other cells.

The term "isolated population" with respect to an isolated population of cells as used herein refers to a population of cells that has been removed and separated from a mixed or heterogeneous population of cells. In some embodiments, an isolated population is a substantially pure population of cells (e.g., hepatic stellate cells) as compared to the heterogeneous population from which the cells were isolated or enriched (e.g., liver tissue). In some embodiments, the isolated population is an isolated population of hepatic stellate cells, e.g., a population of hepatic stellate cells that are at least 80%, at least 85%, at least 90%, at least 92%, at least 95%, at least 98%, at least 99%, or even 99.9% or higher (e.g., a substantially pure population) as compared to a heterogeneous population of cells comprising hepatic stellate cells and/or cells from which the hepatic stellate cells were derived.

The term "substantially pure," with respect to a particular cell population, refers to a population of cells that is at least about 75%, preferably at least about 85%, more preferably at least about 90%, and most preferably at least about 95% pure, with respect to the cells making up a total cell population. That is, the terms "substantially pure" or "essentially purified," with regard to a population of hepatic stellate cells, refers to a population of cells that contain fewer than about 20%, more preferably fewer than about 15%, 10%, 8%, 7%, most preferably fewer than about 5%, 4%, 3%, 2%, 1%, or less than 1%, of cells that are not hepatic stellate cells as defined by the terms herein.

As used herein, the term "treating" includes reducing or alleviating at least one adverse effect or symptom of a condition, disease or disorder. For example, the term "treating" and "treatment" refers to administering to a subject an effective amount of a composition, e.g., an effective amount of a composition comprising a population of engineered hepatic stellate cells, or miRNA, miRNA mimic or nucleic acid encoding an miRNA so that the subject has a reduction in at least one symptom of a given liver disease (e.g., liver fibrosis or non-alcoholic fatty liver disease) or an improvement in the disease, for example, beneficial or desired clinical results. For purposes of this disclosure, beneficial or desired clinical results include, but are not limited to, alleviation of one or more symptoms (e.g., presence of liver enzymes in serum), diminishment of extent of disease, disease stabilization (e.g., not worsening), delay or slowing of disease progression, amelioration or palliation of the disease state, and remission (whether partial or total), whether detectable or undetectable. In some embodiments, treating can refer to prolonging survival as compared to expected survival if not receiving treatment. Thus, one of skill in the art realizes that a treatment can improve the disease condition, but may not be a complete cure for the disease. In some embodiments, treatment can include prophylaxis. However, in alternative embodiments, treatment does not include prophylaxis.

"Treatment" of a liver disorder, a liver disease, or a liver injury (e.g., acute liver injury) as referred to herein refers to therapeutic intervention that stabilizes or improves the function of the liver or stabilizes or reduces liver fibrosis. That is, "treatment" is oriented to the function of the liver. A therapeutic approach that stabilizes or improves the function of the liver or reduces liver fibrosis by at least 10%, and preferably by at least 20%, 30%, 40%, 50%, 75%, 90%, 100% or more, e.g., 2-fold, 5-fold, 10-fold or more, up to and including full function, relative to such function prior to such therapy is considered effective treatment. Effective treatment need not cure or directly impact the underlying cause(s) and/or risk factor(s) of the disease or disorder (e.g., metabolic disease, obesity, hypercholesterolemia or other risk factors) to be considered effective treatment.

As used herein, "prevention" or "preventing," when used in reference to a disease, disorder or symptoms thereof, refers to a reduction in the likelihood that an individual will develop a disease or disorder, e.g., liver fibrosis. The likelihood of developing a disease or disorder is reduced, for example, when an individual having one or more risk factors for a disease or disorder either fails to develop the disorder or develops such disease or disorder at a later time or with less severity, statistically speaking, relative to a population having the same risk factors and not receiving treatment as described herein. The failure to develop symptoms of a disease, or the development of reduced (e.g., by at least 10% on a clinically accepted scale for that disease or disorder) or delayed (e.g., by days, weeks, months or years) symptoms is considered effective prevention.

As used herein, the phrases "therapeutically effective amount" and "prophylactically effective amount" refer to an amount of e.g., engineered HSCs, miRNA, or nucleic acid encoding an miRNA that provides a therapeutic benefit in the treatment, prevention, or management of liver disease, including those involving or inducing liver fibrosis. The specific amount that is therapeutically effective can be readily determined by an ordinary medical practitioner, and can vary depending on factors known in the art, such as, for example, the type and severity of liver disease, the patient's history and age, and the ability to control or mitigate risk factors associated with the induction of liver fibrosis.

The phrase "combination therapy" embraces the administration of miR-412, a miR-412 mimic, a hepatic stellate cell expressing miR-412, or a nucleic acid encoding miR-412 in combination with administration of miR-15a, a miR-15a mimic, a hepatic stellate cell expressing miR-15a, or a nucleic acid encoding miR-15a as part of a specific treatment regimen intended to provide a beneficial effect from the co-action of these therapeutic agents. "Combination therapy" generally is not intended to encompass the administration of two or more of these therapeutic agents as part of separate monotherapy regimens that incidentally and arbitrarily result in the combinations of the present invention. "Combination therapy" is intended to embrace administration of these therapeutic agents in a substantially simultaneous or sequential manner, that is, wherein each therapeutic agent is administered at the same or a different time. Substantially simultaneous administration can be accomplished, for example, by administering to the subject a single composition having a fixed ratio of each therapeutic agent or in multiple, single compositions for each of the therapeutic agents. For example, combination therapy comprising administering a nucleic acid encoding miR-412 with a nucleic acid encoding miR-15a can be achieved by expressing both miRNAs on a single vector. Sequential or substantially simultaneous administration of each therapeutic agent can be effected by any appropriate route including, but not limited to, intrahepatic routes, intravenous routes, and parenteral routes. The therapeutic agents can be administered by the same route or by different routes. For example, a first therapeutic agent of the combination selected may be administered by intravenous injection while the other therapeutic agents of the combination may be administered by intra-hepatic injection. Alternatively, for example, all therapeutic agents may be administered by direct injection into the liver or all therapeutic agents may be administered by intravenous injection. The sequence in which the therapeutic agents are administered is not narrowly critical. "Combination therapy" also can embrace the administration of the therapeutic agents as described above in further combination with other biologically active ingredients (such as, but not limited to, a second and different agent for treatment of liver fibrosis or for reducing risk factors) and non-drug therapies (such as, but not limited to, surgery). Combination agents can include drugs that are used to reduce or eliminate risk factors of liver fibrosis, for example, reduce hypercholesterolemia by co-treatment with a statin agent, or reduce diabetic symptoms by administration of metformin.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g., the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, at least about a 20-fold increase, at least about a 50-fold increase, at least about a 100-fold increase, at least about a 1000-fold increase or more as compared to a reference level.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment of the invention.

Hepatic Stellate Cells (HSCs) & Liver Fibrosis

Hepatic Stellate Cells (also known as perisinusoidal cells or Ito cells) are the major cell type involved in liver fibrosis. HSCs can exist in one of two states: (i) quiescent state or (ii) activated state. In a non-diseased liver, HSCs generally exist in the quiescent state and can be distinguished from other liver cells by the presence of multiple intracellular lipid droplets.

When the liver is damaged HSCs become activated or enter into an activated state. Activation of HSCs is characterized by enhanced proliferation, contractility, chemotaxis, and secretion of collagen scar tissue. This collagen scar tissue is the first step in the pathogenesis of liver fibrosis.

As used herein, the term "liver fibrosis" refers to a scarring process that occurs in the liver in response to injury to the liver and involves excessive accumulation of extracellular matrix proteins such as collagen. Liver fibrosis can result from a wide variety of conditions that cause chronic inflammation of the liver, including chronic alcohol exposure, hepatitis B virus (HBV) infection, non-alcoholic fatty liver disease (NAFLD), hepatitis C virus (HCV) infection, Wilson's disease, alpha-1-antitrypsin deficiency, hemochromatosis, primary biliary cirrhosis, primary sclerosing cholangitis, and autoimmune hepatitis. Such chronic inflammation leads to changes in liver structure, slowing of blood circulation, and necrosis of liver cells. Liver fibrosis is a dynamic process that can progress or regress over periods as short as months. As scar tissue builds up, due to inflammation and the continuance of liver injury, it can eventually disrupt the metabolic functions of the liver. Advanced liver fibrosis can result in cirrhosis, liver failure, and portal hypertension and often requires liver transplantation (and can occur following liver transplantation).

The extent of liver fibrosis can be classified as being in one of at least four stages. Stage 1 liver fibrosis (portal stage) is characterized by normal sized triads, portal inflammation and possible subtle bile duct damage. Granulomas may be detected in Stage 1 liver fibrosis. Stage 2 liver fibrosis (periportal stage) can be characterized by enlarged triads, periportal fibrosis and/or inflammation. Stage 2 is characterized by the finding of a proliferation of small bile ducts. Stage 3 (septal stage) liver fibrosis is characterized by active and/or passive fibrous septa. Stage 4 is characterized by biliary cirrhosis and liver nodules.

Clinically, liver fibrosis can be associated with elevations of liver enzymes such as aspartate aminotransferase (AST), alanine aminotransferase (ALT) and alkaline phosphatase (AP). Elevated liver enzymes can show up in blood tests before any actual fibrosis occurs in response to the damage that leads to the fibrosis. As liver functioning is impaired overt signs and symptoms can manifest, for example, inflammation, pain in the area of the liver, loss of appetite, nausea and vomiting, jaundice (yellowing of the skin and the whites of the eyes), spider angioma, caput medusa (appearance of dilated veins on the abdomen), and discoloration of the skin in rash-like patches. Overt signs and/or symptoms can indicate that the scarring has progressed to a potentially dangerous level but will not occur in all cases or stages of liver fibrosis.

These clinical features of liver fibrosis can be used in the diagnosis of liver disease in a subject and is well within the abilities of a skilled clinician. In addition, such clinical features can be monitored to determine efficacy of one or more of the treatments described herein. For example, movement of an individual from a more severe stage of liver fibrosis, such as stage 4, to a less severe stage, such as stage 3, can indicate the efficacy of a given treatment. In addition, it is also contemplated herein that while an individual may not move from one liver fibrosis stage to another, that reduction in at least one symptom characteristic of that liver stage can also be considered efficacious treatment.

miRNAs that Induce Hepatic Stellate Cell Quiescence

Certain non-coding RNAs are known to produce functional RNA molecules with important roles in diverse cellular processes. Such non-translated, non-coding RNA molecules can include ribosomal RNAs, tRNAs, snRNAs, snoRNAs, tncRNAs, rasiRNAs, short hairpin RNAs (shRNAs), short temporal RNAs (stRNAs), short hairpin RNAs (shRNAs), siRNAs, miRNAs and smnRNAs. These non-coding RNAs can be involved in a variety of cellular processes including transcriptional regulation, translational regulation, developmental timing, viral surveillance, immunity, chromosome maintenance, ribosomal structure and function, gene imprinting, subcellular compartmentalization, pre-mRNA splicing, and guidance of RNA modifications. RNA-mediated processes are now also believed to direct heterochromatin formation, genome rearrangements, cellular differentiation and DNA elimination.

The studies described in the working Examples indicate that miR-412 and miR-15a (administered independently or in combination) can induce a quiescent state in a hepatic stellate cell. Further, the studies described herein show that induction of quiescence in a hepatic stellate cell can treat and/or prevent liver disease. Thus, both miR-412 and miR-15a, or nucleic acids encoding miR-412 and miR-15a, are contemplated herein for the treatment of liver disease in a variety of mammals, including humans, mice, horses, sheep, and primates.

In some embodiments, modifications can be made to the miRNA, which are preferably in the lesser conserved region of the miRNA. One of skill in the art can easily compare the sequences and orthologs in the following two tables to determine an appropriate region in which to introduce a modification, such as a substitution, insertion or deletion. In some embodiments, an ortholog from one mammalian species can be used with the methods and composition described herein for the treatment of a second species or for the generation of quiescent HSCs from a different species. For example, a human miRNA can be used to generate a quiescent HSC from a mouse. Similarly, an HSC expressing a human miRNA as described herein can be administered to a mouse (see e.g., the working Examples). One of skill in the art will appreciate that administration of any of the compositions described herein should be performed in a manner, or with formulations, that do not induce an unwanted immune cell reaction in the subject to be treated.

TABLE 1 miR-412 sequences of selected mammals

| | miR-412 | SEQ ID NO. |
|---|---|---|
| Human<br>NCBI Ref No:<br>NR_030155.1 | ctggggtacg gggatggatg gtcgaccagt tggaaagtaa ttgtttctaa tgtacttcac ctggtccact agccgtccgt atccgctgca g | 1 |
| Mouse<br>NCBI Ref No.<br>NR_029917.1 | gggtatggga cggatggtcg accagctgga aagtaattgt ttctaatgta cttcacctgg tccactagcc gtcggtgccc | 2 |
| Horse<br>NCBI Ref No.<br>NR_033027.1 | gggtacagga gggatggtcg accagttgga aagtaattgt ttctaatgta cttcacctgg tccactagcc gtccgtaccc | 3 |
| Sheep<br>NCBI Ref No.<br>NR_107931.1 | agggaagaac gtcagtacca gcaaccactc tggggtacag gacggatggt cgaccagttg gaaagtaatt gtttctaatg tacttcacct ggtccactag ctgtccgtac ccactgcagc ctgc | 4 |
| Chimpanzee<br>NCBI Ref No:<br>NR_035792 | tggggtacgg ggatggatgg tcgaccagtt ggaaagtaat tgtttctaat gtacttcacc tggtccacta gccgtccgta tccgctgcag | 5 |
| Rhesus Monkey<br>NCBI Ref No:<br>NR_032514.1 | ctggggtacg gggatggatg gtcgaccagt tggaaagtaa ttgtttctaa tgtacttcac ctggtccact agccgtccgt atccgctgca g | 6 |
| Cow<br>NCBI Ref No:<br>NR_031065.1 | ctggggtaca ggacggatgg tcgaccagtt ggaaagtaat tgtttctaat gtacttcacc tggtccacta gctgtccgta cccactgcag | 7 |
| Goat<br>NCBI Ref No:<br>NR_129746.1 | agggaagaac gtcagtacca gcaaccactc gggtacagga cggatggtcg accagttgga aagtaattgt ttctaatgta cttcacctgg tccactagct gtccgtaccc actgcagcct gc | 8 |
| Rat<br>NCBI Ref No:<br>NR_032115 | gggacggatg gtcgaccagc tggaaagtaa ttgtttctaa tgtacttcac ctggtccact agccgtcggt | 9 |

TABLE 2 miR-15a sequences of selected mammals

| | miR-15a | SEQ ID NO. |
|---|---|---|
| Human<br>NCBI Ref No:<br>NR_000013.11 | ccttggagta aagtagcagc acataatggt ttgtggattt tgaaaaggtg caggccatat tgtgctgcct caaaaataca agg | 10 |
| Mouse<br>NCBI Ref No.<br>NR_000080.6 | cccttggagt aaagtagcag cacataatgg tttgtggatg ttgaaaaggt gcaggccata ctgtgctgcc tcaaaataca agga | 11 |
| Horse<br>NCBI Ref No.<br>NR_032957.1 | tagcagcaca taatggtttg tggattttga aaaggtgcag gccatattgt gctgcct | 12 |
| Dog<br>NCBI Ref No.<br>NR_006604.3 | tagcagcaca taatggtttg tggattttga aaaggtgcag gccatattgt gctgcctca | 13 |
| Chimpanzee<br>NCBI Ref No:<br>NR_106592.1 | ccttggagta aagtagcagc acataatggt ttgtggattt tgaaaaggtg caggccatat tgtgctgcct caaaaataca agg | 14 |
| Rhesus Monkey<br>NCBI Ref No:<br>NR_032066.1 | ccttggagta aagtagcagc acataatggt ttgtggattt tgaaaaggtg caggccatat tgtgctgcct caaaaataca agg | 15 |
| Cow<br>NCBI Ref No:<br>NR_030793.1 | ccttggagta aagtagcagc acataatggt ttgtggattt tgaaaaggtg caggccatat tgtgctgcct caaaaataca agg | 16 |

TABLE 2-continued miR-15a sequences of selected mammals

| | miR-15a | SEQ ID NO. |
|---|---|---|
| Goat<br>NCBI Ref No:<br>NR_129605.1 | accttggagt aaagtagcag cacataatgg tttgtggatt<br>ttgaaaaggt gcaggccata ttgtgctgcc tcaaaaatac<br>aaggatctga tcttc | 17 |

Nucleic acids encoding one or more of the miRNAs described herein can be included on a vector, such as a lentiviral, retroviral, adenoviral, AAV, pox vector, or other vector. Such vectors are specifically contemplated herein for use in the treatment of liver disease. Alternatively, the miRNA can be administered via a plasmid or naked nucleic acid sequence delivery.

In some embodiments, the miRNAs described herein are synthetically produced or obtained from commercial sources, such as Dharmacon and Invitrogen.

In one embodiment, the compositions described herein comprise a miRNA mimic of miR-412 and/or miR-15a. In one embodiment, the miRNA mimic is an oligomeric compound.

The term "oligomeric compound(s)" refers to polymeric structures which are capable of mimicking small non-coding RNAs. The term "oligomeric compound" includes, but is not limited to, compounds comprising oligonucleotides, oligonucleosides, oligonucleotide analogs, oligonucleotide mimmetics and combinations of these. Oligomeric compounds also include, but are not limited to, antisense oligomeric compounds, antisense oligonucleotides, siRNAs, alternate splicers, primers, probes and other compounds that hybridize to at least a portion of the target nucleic acid. Oligomeric compounds are routinely prepared linearly but can be joined or otherwise prepared to be circular and may also include branching. Separate oligomeric compounds can hybridize to form double stranded compounds that can be blunt-ended or may include overhangs on one or both termini. In general, an oligomeric compound comprises a backbone of linked monomeric subunits where each linked monomeric subunit is directly or indirectly attached to a heterocyclic base moiety. The linkages joining the monomeric subunits, the sugar moieties or sugar surrogates and the heterocyclic base moieties can be independently modified giving rise to a plurality of motifs for the resulting oligomeric compounds including hemimers, gapmers and chimeras.

Generally, oligomeric compounds designed to mimic pri-miRNAs are from about 70 to about 450 monomeric subunits in length, or from about 110 to 430 subunits in length. Oligomeric compounds of the invention designed to mimic pre-miRNAs are from about 50 to about 110 monomeric subunits in length, or from about 60 to about 80 subunits in length. Oligomeric compounds of the invention designed to mimic mature miRNAs are from about 17 to about 25 monomeric subunits in length, and can be single- or double-stranded with either or both strands comprising from about 17 to about 25 subunits.

Where the oligomeric compounds act as mimics or replacements for small non-coding RNAs, the oligomeric compounds at least 70% sequence identity to a small non-coding RNA (e.g., miR-412 or miR-15a) or a region thereof. In some embodiments the oligomeric compound as that term is used herein can comprise at least 90% sequence identity and in some embodiments can comprise at least 95% sequence identity to the small non-coding RNA or a region thereof.

RNA oligomers can be synthesized by methods known in the art or purchased from various RNA synthesis companies such as for example Dharmacon Research Inc., (Lafayette, Colo.). Irrespective of the particular protocol used, the oligomeric compounds as described herein can be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed.

In some embodiments, the miR-412 and/or miR-15a miRNA is a pre-miRNA.

miRNAs useful with the methods and compositions described herein include sequence variants of miR-412 and/or miR-15a that retain at least 50% of the target gene-inhibitory function or ability to induce quiescence in an HSC of wild type mature miR-412 and/or miR-15a. miRNA variants generally fall into one or more of three classes: substitution, insertional or deletional variants. Insertions include 5' and/or 3' terminal fusions as well as intrasequence insertions of single or multiple residues. Insertions can also be introduced within the mature sequence of the miRNA. Intrasequence insertions ordinarily will be smaller insertions than those at the 5' or 3' terminus, on the order of 1 to 4 or 1-10 residues. It is understood that the variants, substitutions, insertions or deletions of residues will not result in a deleterious effect on the function of the variant in its ability to bind to, and inhibit the expression of e.g., at least one gene marker of HSC activation, unless so desired. It is specifically contemplated herein that the modified miRNA can have improved function over the unmodified miRNA, for example, in inducing quiescence in a hepatic stellate cell.

Alternatively, as discussed below, variants can have improved properties such as avoiding endogenous mechanisms that would otherwise inhibit or limit miRNA function, or be processed more efficiently to active form.

Substitutional variants are those in which at least one residue has been removed and a different residue inserted in its place. Deletion variants are characterized by the removal of one or more residues from the RNA sequence. These variants ordinarily are prepared by site specific mutagenesis of nucleotides in the DNA encoding miR-412 or miR-15a, thereby producing DNA encoding the variant, and thereafter expressing the DNA in recombinant cell culture. However, variant fragments can be conveniently prepared by in vitro synthesis. The variants typically exhibit the same qualitative biological activity as the naturally-occurring analogue, although variants also are selected in order to modify the characteristics of the desired miRNA (e.g., miR-412 and/or miR-15a).

While the site for introducing a sequence variation is selected, the mutation per se need not be predetermined. Thus, if the nucleotide at a site to be mutated is a G, mutation to any of A, T, or C can be made with the expectation that the change will modify function of the products; while, in this example, one of A, T, or C may be optimal, it is to be expected that any of them will be beneficial. Of course, in order to optimize the performance of a mutation at a given site, random mutagenesis can be conducted at the target region and the expressed variants screened for the optimal combination of desired activity. Techniques for making substitution mutations at predetermined sites in DNA having a known sequence are well known. Nucleotide substitutions are typically of single residues; insertions can be on the order of about 1 to 10 residues; and deletions can range from about 1 to 30 residues. Deletions or insertions preferably are made in adjacent pairs; i.e., a deletion of 2 residues or insertion of 2 residues.

Substitutions, deletion, insertions or any combination thereof can be combined to arrive at a final construct. Changes can be made to increase the activity of the miRNA, to increase its biological stability or half-life, and the like. All such modifications to the nucleotide sequences encoding such miRNA are encompassed.

Suitable nucleic acids for use in the methods described herein include, but are not limited to, miR-412 and/or miR-15a pri-miRNA, miR-412 and/or miR-15a pre-miRNA, mature miR-412 and/or miR-15a miRNA or fragments of variants thereof that retain the biological activity of miR-412 and/or miR-15a miRNA and DNA encoding miR-412 and/or miR-15a pri-miRNA, miR-412 and/or miR-15a pre-miRNA, mature miR-412 and/or miR-15a miRNA, fragments or variants thereof, or DNA encoding regulatory elements of miR-412 and/or miR-15a miRNA.

miRNA Modifications to Enhance Processing

MicroRNAs (miRNAs) are a group of short, non-coding RNAs that bind target mRNAs to either inhibit their translation or reduce their stability. miRNAs are transcribed in the nucleus as part of a primary microRNA (pri-miRNA), which are cleaved by the cellular Microprocessor complex and liberating a structure known as the precursor microRNA (pre-miRNA).

The pre-miRNA is transported from the nucleus to the cytoplasm and is subsequently cleaved by the enzyme Dicer with its cofactor trans-activator RNA (tar)-binding protein (TRBP).

It is now appreciated that miRNAs are involved with the onset of various diseases, immunoregulation, neural growth and stem cell renewal/maintenance. Thus, miRNAs can be designed to enhance or repress processing of the endogenous form of the messenger RNA by removing or introducing mis-matches, which are removed to enhance processing, and alternatively introduced to repress processing.

Within the context of the designed artificial miRNAs, the term "miRNA" refers to any non-endogenous microRNA molecule that can be involved in RNA-based gene regulation. Accordingly, "miRNA" refers to a short, non-coding mRNA capable of modulating the productive utilization of mRNA. The term "mRNA" refers to a nucleic acid transcribed from a gene from which a polypeptide is translated, and can include non-translated regions such as a 5'UTR and/or a 3'UTR. A miRNA can include a nucleotide sequence that is completely or partially complementary to any sequence of an mRNA molecule, including translated regions, the 5'UTR, the 3'UTR, and sequences that include both a translated region and a portion of either 5'UTR or 3'UTR. A miRNA can also comprise a nucleotide sequence that is complementary to a region of an mRNA molecule spanning the start codon or the stop codon.

In some embodiments, a miRNA is introduced as a pre-miRNA nucleic acid sequence, which can optionally include nucleic acid sequences that affect the intracellular processing of the pre-miRNA. One such element can include a nucleic acid sequence encoding a miRNA flanking sequence. As used herein, the term "miRNA flanking sequence" refers to nucleotide sequences comprising miRNA processing elements. miRNA processing elements are the minimal nucleic acid sequences which contribute to the production of mature miRNA from precursor miRNA. Often these elements are located within a 40 nucleotide sequence that flanks a miRNA stem-loop structure. In some instances the miRNA processing elements are found within a stretch of nucleotide sequences of between 5 and 4,000 nucleotides in length that flank a miRNA stem-loop structure.

Thus, in some embodiments the flanking sequences are 5-4,000 nucleotides in length. As a result, the length of the precursor molecule may be, in some instances at least about 150 nucleotides or 270 nucleotides in length. The total length of the precursor molecule, however, may be greater or less than these values. In other embodiments the minimal length of the miRNA flanking sequence is 10, 20, 30, 40, 50, 60, 70, 80, 90, 100, 150, 200 and any integer there between. In other embodiments the maximal length of the miRNA flanking sequence is 2000, 2100, 2200, 2300, 2400, 2500, 2600, 2700, 2800, 2900, 3000, 3100, 3200, 3300, 3400, 3500, 3600, 3700, 3800, 3900 4000 and any integer there between. In other embodiments, the flanking sequence is between 25-500 nucleotides, between 25-400 nt, between 25-300 nt, between 25-200 nt, between 25-100 nt, between 25-50 nt, between 50-500 nt, between 75-500 nt, between 100-500 nt, between 200-500 nt, between 250-500 nt, between 300-500 nt, between 350-500 nt, between 400-500 nt, between 450-500 nt, between 75-300 nt, between 100-300 nt, between 100-200 nt, or any range in between.

The miRNA flanking sequences may be native/endogenous miRNA flanking sequences or artificial miRNA flanking sequences. A native/endogenous miRNA flanking sequence is a nucleotide sequence that is ordinarily associated in naturally existing systems with miRNA sequences, i.e., these sequences are found within the genomic sequences surrounding the minimal miRNA hairpin in vivo. Artificial miRNA flanking sequences are nucleotide sequences that are not found to be flanking to miRNA sequences in naturally existing systems. The artificial miRNA flanking sequences may be flanking sequences found naturally in the context of other miRNA sequences. Alternatively they may be composed of minimal miRNA processing elements which are found within naturally occurring flanking sequences and inserted into other random nucleic acid sequences that do not naturally occur as flanking sequences or only partially occur as natural flanking sequences.

The miRNA flanking sequences within the precursor miRNA molecule can flank one or both sides of the stem-loop structure encompassing the miRNA sequence. Thus, one end (i.e., 5') of the stem-loop structure can be adjacent to a single flanking sequence and the other end (i.e., 3') of the stem-loop structure cannot be adjacent to a flanking sequence. Particular structures have flanking sequences on both ends of the stem-loop structure. The flanking sequences may be directly adjacent to one or both ends of the stem-loop structure or may be connected to the stem-loop structure through a linker, additional nucleotides or other molecules.

In some instances the pri-miRNA molecule can include more than one stem-loop structure. The multiple stem-loop structures can be linked to one another through a linker, such as, for example, a nucleic acid linker or by a miRNA flanking sequence or other molecule or some combination thereof.

The artificial RNAs disclosed herein can be synthesized from a polymer of nucleotides (i.e., molecules comprising a sugar (e.g., ribose) linked to a phosphate group and to an exchangeable organic base, which is either a substituted pyrimidine (e.g., cytosine (C), or uracil (U)) or a substituted purine (e.g., adenine (A) or guanine (G)). As used herein, the term nucleotides also can include polynucleosides (i.e., a polynucleotide minus the phosphate) and any other organic base containing polymer.

The artificial miRNAs can also encompass nucleotides with substitutions or modifications, such as in the bases and/or sugars. Modified bases include any base that is chemically distinct from the naturally occurring bases typically found in RNA (C, G, A, and U), but which share basic chemical structures with these naturally occurring bases. The modifications can improve, e.g., stability, target binding affinity, or target specificity, among other effects. The modified nucleotide base may be, for example, dihydrouracil, pseudouracil, 2-thiouracil, 4-thiouracil, 5-aminouracil, 5-(C1-C6)-alkyluracil, 5-(C2-C6)-alkenyluracil, 5-(C2-C6)-alkynyluracil, 5-(hydroxymethyl)uracil, 5-chlorouracil, 5-fluorouracil, 5-bromouracil, 5-hydroxycytosine, 5-(C1-C6)-alkylcytosine, 5-(C2-C6)-alkenylcytosine, 5-(C2-C6)-alkynylcytosine, 5-chlorocytosine, 5-fluorocytosine, 5-bromocytosine, N2-dimethylguanine, 2,4-diamino-purine, 8-azapurine, a substituted 7-deazapurine, 7-deaza-7-substituted and/or 7-deaza-8-substituted purine, 5-hydroxymethylcytosine, N4-alkylcytosine, N4-ethylcytosine, 5-hydroxydeoxycytidine, 5-hydroxymethyldeoxycytidine, N4-alkyldeoxycytidine, N4-ethyldeoxycytidine, 6-thiodeoxyguanosine, deoxyribonucleosides of nitropyrrole, C5-propynylpyrimidine, diaminopurine, 2,6-diaminopurine, inosine, 5-methylcytosine, 2-aminopurine, 2-amino-6-chloropurine, hypoxanthine or other modifications of a natural nucleoside bases.

The artificial RNAs can also encompass various chemical modifications and substitutions, in comparison to natural RNA involving phosphodiester internucleotide bridges and/or 3-D-ribose units. Replacing a phosphodiester bridge located at the 3' and/or the 5' end of a nucleotide can make artificial RNAs disclosed herein more resistant to degradation (i.e., are stabilized). Exemplary modified internucleotide bridges include phosphorothioate, phosphorodithioate, NR1 R2-phosphoramidate, boranophosphate, a-hydroxybenzyl phosphonate, phosphate-(C1-021)-0-alkyl ester, phosphate-[(C6-C12)aryl-(C1-021)-0-alkyl]ester, (C1-C8) alkylphosphonate and/or (C6-12)arylphosphonate bridges, (C7-C12)-a-hydroxymethyl-aryl, wherein (C6-C12)aryl, (C6-C20)aryl and (C6-C14)aryl are optionally substituted by halogen, alkyl, alkoxy, nitro, cyano, and where R1 and R2 are, independently of each other, hydrogen, ($C_1$-C18)-alkyl, (C6-C20)-aryl, (C6-C14)-aryl-(C1-C8)-alkyl, hydrogen, ($C_1$-C8)-alkyl, (C1-C4)-alkyl and/or methoxyethyl, or R1 and R2 form, together with the nitrogen atom carrying them, a 5-6-membered heterocyclic ring which can additionally contain a further heteroatom from the group 0, S and N. Dephospho bridges can also be used. Dephospho bridges are described, for example, in Uhlmann and Peyman in "Methods in Molecular Biology", Vol. 20, "Protocols for Oligonucleotides and Analogs", Agrawal, Ed., Humana Press, Totowa 1993, Chapter 16, pp. 355 if). Exemplary dephospho bridges include formacetal, 3'-thioformacetal, methylhydroxylamine, oxime, methylenedimethyl-hydrazo, dimethylenesulfone and/or silyl groups.

Beta-ribose units can be replaced by modified sugar units such as 3-D-ribose, 6-D-2'-deoxyribose, L-2'-deoxyribose, 2'-F-2'-deoxyribose, 2'-F-arabinose, 2'-0-(C1-C6)alkyl-ribose, 2'-0-(C1-C6)alkyl-ribose, 2'-0-methyl ribose, 2'-0-(C2-C6)alkenyl-ribose, 2'-[0-(C1-C6)alkyl-0-(C1-C6)alkyl]-ribose, 2'-NH2-2'-deoxyribose, 6-D-xylo-furanose, a-arabinofuranose, 2,4-dideoxy-6-D-erythro-hexo-pyranose or carbocyclic and/or open-chain sugar analogs and/or bicyclosugar analogs.

Sugar phosphate units from the sugar phosphate backbone can also be replaced by other units such as "morpholino-derivative" oligomers (see, for example, Stirchak et al. (1989) Nucleic Acids Res 17:6129-41); polyamide nucleic acids (PNA; see, for example, Nielsen et al. (1994) Bioconjug Chem 5:3-7) such as by 2-aminoethylglycine; peptide nucleic acids with phosphate groups (PHONA); locked nucleic acids (LNA); and/or nucleotides having backbone sections with alkyl linkers or amino linkers. Alkyl linkers can be branched or unbranched, substituted or unsubstituted, and chirally pure or a racemic mixture.

Artificial RNAs disclosed herein can also be conjugated to lipophilic or lipid moieties. Exemplary lipophilic or lipid moieties include cholesteryls, modified cholesteryls, cholesterol derivatives, reduced cholesterols, substituted cholesterols, cholestans, C1-6 alkyl chains, cholic acid, taurocholic acid, deoxycholate, oleyl litocholic acid, oleoyl cholenic acid, glycolipids, phospholipids, sphingolipids, isoprenoids, saturated fatty acids, unsaturated fatty acids or fatty acid esters. The lipophilic or lipid moieties can be attached via any suitable direct or indirect linkage such as, without limitation, by an ester or an amide. Linkages can include spacer moieties, for example one or more nucleotide residues, oligoethyleneglycol, triethyleneglycol, hexaethylenegylcol or an alkane-diol, such as butanediol.

Artificial RNAs disclosed herein can also be conjugated to Nuclear Localization Signals (NLS). "Nuclear localization signals" are sequences (in some embodiments amino acid sequences) that can direct artificial RNAs across the nuclear membrane and into the nucleus of the cell. A nuclear localization signal can also target the exterior surface of a cell. Nuclear localization signals are generally basic, comprise a short sequence of 4-8 amino acids and are typically rich in lysine and arginine residues while also often comprising proline residues.

Additional methods contemplated for generating modified miRNAs for use in the methods and compositions described herein can be found in PCT/US13/76256, which is incorporated herein by reference in its entirety.

Nucleic Acid Vectors

In some embodiments of the aspects described herein, a nucleic acid sequence(s) encoding miR-412 and/or miR-15a are introduced into a hepatic stellate cell (e.g., in vivo, in vitro or ex vivo) using a vector or plasmid. As used herein, the term "vector" is used interchangeably with "plasmid" to refer to a nucleic acid molecule capable of transporting another nucleic acid to which it has been linked. Vectors capable of directing the expression of genes and/or nucleic acid sequence to which they are operatively linked are referred to herein as "expression vectors." In general, expression vectors of utility in the methods and described herein are often in the form of "plasmids," which refer to circular double stranded DNA loops which, in their vector form are not bound to the chromosome.

Expression vectors can be used in different embodiments, for example, but not limited to, plasmids, episomes, bacteriophages or viral vectors, and such vectors can integrate into the host's genome or replicate autonomously in the particular cellular system used. In some embodiments, integration of the nucleic acid sequence encoding miR-412 and/or miR-15a into the host genome is desired to maintain hepatic stellate cells in their quiescent state, which in turn prevents and/or treats liver fibrosis even in the presence of environmental and/or genetic factors that favor hepatic stellate cell activation. In embodiments where engineered HSCs expressing miR-412 and/or miR-15a are administered to a subject, it may also be desirable to ablate activated endogenous HSCs, thus "replacing" the activated endogenous HSCs with the engineered, quiescent HSCs. Genomic integration can be achieved by the use of a genomic integrated vector, or "integrated vector", which can become integrated into the chromosomal DNA or RNA of a hepatic stellate cell in vivo or in vitro. In some embodiments, the nucleic acid sequence or sequences encoding miR-412 and/or miR-15a integrates into the chromosomal DNA of a HSC along with components of the vector sequence. In other embodiments, the nucleic acid sequence encoding miR-412 and/or miR-15a directly integrates into chromosomal DNA of a HSC, in the absence of any components of the vector by which it was introduced. The number of copies of miR-412 and/or miR-15a that integrate into the chromosomal DNA of a HSC can impact the HSC, and thus it is preferred, in some embodiments, that only one copy is integrated per HSC.

Inducible and non-inducible expression vectors can also be used. Other forms of expression vectors known by those skilled in the art which serve the equivalent functions can also be used.

Another type of vector is an episomal vector, i.e., a nucleic acid capable of extra-chromosomal replication. Such plasmids or vectors can include plasmid sequences from bacteria, viruses or phages. Such vectors include chromosomal, episomal and virus-derived vectors e.g., vectors derived from bacterial plasmids, bacteriophages, yeast episomes, yeast chromosomal elements, and viruses, vectors derived from combinations thereof, such as those derived from plasmid and bacteriophage genetic elements, cosmids and phagemids. A vector can be a plasmid, bacteriophage, bacterial artificial chromosome (BAC) or yeast artificial chromosome (YAC). A vector can be a single or double-stranded DNA, RNA, or phage vector. In some embodiments, the miR-412 and/or miR-15a are introduced into a cellular system using a BAC vector.

In some embodiments where miR-412 and miR-15a are simultaneously expressed in an HSC, miR-412 and/or miR-15a can be encoded separately by individual expression vectors expressed in the same HSC. In some embodiments, miR-412 and miR-15a can be encoding by the same expression vector expressed in a HSC.

In certain embodiments, the nucleic acid(s) encoding miR-412 and/or miR-15a can be encoded on a vector for CRISPR/Cas mediated integration of the nucleic acid(s) into the genome of a hepatic stellate cell, in vitro, ex vivo or in vivo. For example, in regard to using sequences associated with CRISPR, one of skill in the art can insert a short DNA fragment containing the DNA binding domain target site into a guide RNA expression plasmid. The sgRNA expression plasmid contains the DNA binding domain target site (about 20 nucleotides), a form of the tracrRNA sequence (the scaffold) as well as a suitable promoter and necessary elements for proper processing in eukaryotic cells. Such vectors are commercially available (see, for example, Add-gene). Many of the systems rely on custom, complementary oligos that are annealed to form a double stranded DNA and then cloned into the sgRNA expression plasmid. In some embodiments, co-expression of the sgRNA and the appropriate Cas enzyme or domain thereof can be achieved using the same or separate plasmids in transfected cells results.

Inducing Quiescence/Engineering a Hepatic Stellate Cell

The vectors comprising miR412 and/or miR-15a described herein can be "introduced" into hepatic stellate cells as a nucleic acid sequence comprising polynucleotides, preferably DNA, by techniques well-known in the art for introducing DNA and RNA into cells. The term "transduction" refers to any method whereby a nucleic acid sequence is introduced into a cell, e.g., by transfection, lipofection, electroporation, biolistics, passive uptake, lipid:nucleic acid complexes, viral vector transduction, injection, contacting with naked DNA, gene gun, and the like. The vectors, in the case of phage and viral vectors can also be introduced into cells as packaged or encapsidated virus by well-known techniques for infection and transduction. Viral vectors can be replication competent or replication defective. In the latter case, viral propagation generally occurs only in complementing host cells. In some embodiments, the biological converter switches are introduced into a cell using other mechanisms known to one of skill in the art, such as a liposome, microspheres, gene gun, fusion proteins, such as a fusion of an antibody moiety with a nucleic acid binding moiety, or other such delivery vehicle.

Vectors comprising nucleic acid sequences encoding miR-412 and/or miR-15a can be introduced into a cell using any method known to one of skill in the art. The term "transformation" as used herein refers to the introduction of genetic material (e.g., a vector comprising one or more modules of an engineered DNA methylation system) comprising one or more modules or engineered DNA methylation systems described herein into a cell, tissue or organism. Transformation of a cell can be stable or transient. The term "transient transformation" or "transiently transformed" refers to the introduction of one or more transgenes into a cell in the absence of integration of the transgene into the host cell's genome. Transient transformation can be detected by, for example, enzyme linked immunosorbent assay (ELISA), which detects the presence of a polypeptide encoded by one or more of the transgenes. Alternatively, transient transformation can be detected by detecting the activity of the protein encoded by the transgene. The term "transient transformant" refers to a cell which has transiently incorporated one or more transgenes.

In contrast, the term "stable transformation" or "stably transformed" refers to the introduction and integration of one or more transgenes into the genome of a cell or cellular system, preferably resulting in chromosomal integration and stable heritability through meiosis. Stable transformation of a cell can be detected by Southern blot hybridization of genomic DNA of the cell with nucleic acid sequences, which are capable of binding to one or more of the transgenes. Alternatively, stable transformation of a cell can also be detected by the polymerase chain reaction of genomic DNA of the cell to amplify transgene sequences. The term "stable transformant" refers to a cell, which has stably integrated one or more transgenes into the genomic DNA. Thus, a stable transformant is distinguished from a transient transformant in that, whereas genomic DNA from the stable transformant contains one or more transgenes, genomic DNA from the transient transformant does not contain a transgene. Stable transformation results in the constitutive expression of the transgene in the cell. In some embodiments, it may be desirable to also include sequences around the integrated transgene such that the integrated transgene can be easily removed using the CRISPR/Cas system if (i) treatment is no longer desired, (ii) complete reversal of liver fibrosis is achieved, (iii) integration into the host genome disrupted normal gene expression patterns and/or cell function, or (iv) liver tissue protection and/or regeneration induced by activated HSCs, for example, from acute liver damage by collagen secretion, cytokine secretion and/or growth factor secretion from activated HSCs is warranted.

In one embodiment, miR-412 and/or miR-15a is/are transiently expressed in a hepatic stellate cell in vivo or in an engineered quiescent HSC. Alternatively, miR-412 and/or miR-15a can be constitutively expressed in a hepatic stellate cell in vivo or in an engineered quiescent HSC. Whether transient or constitutive expression is selected can be determined by one of skill in the art based on the severity of existing liver fibrosis, the length of time treatment is required to treat/prevent liver fibrosis, genetic markers indicating a risk of liver fibrosis development, and the degree to which existing risk factors can be controlled or mitigated in the subject.

CRISPR/Cas-Mediated Delivery of Compositions

It is specifically contemplated herein that a nucleic acid encoding an miRNA, such as miR-412, can be introduced/delivered and integrated into the genome of a hepatic stellate cell (e.g., in vivo, ex vivo, or in vitro). Therefore, in some embodiments, the miRNA or nucleic acid encoding the miRNA can be modified such that they are recognized by the CRISPR (Clustered Regularly Interspaced Short Palindromic Repeats)/Cas system for integration of the coding sequence into the genome. For example, the nucleic acid encoding the desired miRNA can comprise a CRISPR sequence element, such as a CRISPR DNA sequence that can be bound by a Cas protein or DNA binding domain.

CRISPR (Clustered Regularly Interspaced Short Palindromic Repeats) is an acronym for DNA loci that contain multiple, short, direct repetitions of base sequences. CRISPRs are often associated with cas genes which code for proteins that perform various functions related to CRISPRs. The CRISPR/Cas system functions as a prokaryotic immune system by conferring resistance to exogenous genetic elements such as plasmids and phages thereby imparting for a form of acquired immunity. Endogenous CRISPR spacers recognize and silence exogenous genetic elements in a manner similar to RNAi in eukaryotic organisms. In embodiments of the methods and compositions described herein, the CRISPR/Cas-mediated genome modulating composition refers to elements of a CRISPR system needed to carry out CRISPR/Cas-mediated genome modulation in a mammalian subject for use with the methods and compositions described herein.

CRISPR/Cas-mediated genome editing compositions (e.g., vectors) typically include one or more nucleic acids encoding a crRNA, a tracrRNA (or chimeric thereof also referred to a guide RNA or single guide RNA) and a Cas enzyme, such as, for example, Cas9. The CRISPR/Cas-mediated genome modulating composition includes a donor polynucleotide that can be recombined into the target cell's genome, such as a nucleic acid sequence encoding miR-412 or miR-15a at or adjacent to the target site (e.g., the site of single or double strand break induced by the Cas9).

The CRISPR/Cas system has been adapted for use as gene editing (silencing, enhancing or changing specific genes) for use in eukaryotes (see, for example, Cong, Science, 15:339 (6121):819-823 (2013) and Jinek, et al., iScience, 337 (6096):816-21 (2012)). By transfecting a cell with the required elements including a cas gene and specifically designed CRISPRs, an organism's genome can be cut and modified at any desired location. Methods of preparing compositions for use in genome editing and genome modulation using the CRISPR/Cas systems are described in detail in WO 2013/176772 and WO 2014/018423, which are specifically incorporated by reference herein in their entireties.

Non-limiting examples of Cas proteins that can be used with the methods and compositions described herein include Cas9, Cas3, Cas4, Cas5, Cas5e (or CasD), Cas6, Cas6e, Cas6f, Cas7, Cas8a1, Cas8a2, Cas8b, Cas8c, Cas10, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, and Cu196, and TALES.

In some embodiments, the CRISPR/Cas protein can be a wild type CRISPR/Cas protein, a modified CRISPR/Cas protein, or a fragment of a wild type or modified CRISPR/Cas protein. The CRISPR/Cas-like protein can be modified to increase nucleic acid binding affinity and/or specificity, alter an enzymatic activity, and/or change another property of the protein. Alternatively, the CRISPR/Cas-like protein can be truncated to remove domains that are not essential for the functions of the systems described herein.

In some embodiments of the methods and compositions disclosed herein, a nucleic acid sequence encoding a CRISPR enzyme or domain thereof is codon optimized for expression in particular cells, such as eukaryotic cells. The eukaryotic cells can be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules.

In some embodiments, the CRISPR protein and/or miRNA (or nucleic acids thereof) comprise one or more nuclear localization sequences (NLSs). When more than one NLS is present, each may be selected independently of the others, such that a single NLS may be present in more than one copy and/or in combination with one or more other NLSs present in one or more copies. In general, the one or more NLSs are of sufficient strength to drive accumulation of the CRISPR enzyme or domain thereof in a detectable amount in the nucleus of a eukaryotic cell. In general, strength of nuclear localization activity can derive from the number of NLSs in the CRISPR enzyme, the particular NLS(s) used, or a combination of these factors. Confirmation of accumulation in the nucleus can be performed by any suitable technique known to those of skill in the art.

Sources of Hepatic Stellate Cells

A hepatic stellate cell, for example an HSC to be engineered, can be obtained from a variety of sources. For example, primary hepatic stellate cells (e.g., activated or quiescent) or hepatic progenitor cells (e.g., adult stem cells) can be obtained directly from a liver biopsy. However, it is also contemplated herein that the HSC or population thereof is a cultured and/or immortalized cell(s). The HSC or population thereof can also be derived from a reprogrammed cell, such as an induced pluripotent stem cell, or a pluripotent stem cell. In certain embodiments, the HSC can be derived from an embryonic stem cell or an amniotic stem cell.

In some embodiments, the HSCs are autologous cells but HSCs can also be derived from another individual (e.g., allogeneic cells) or from another species (e.g., xenogeneic cells), if so desired.

Stem Cells and/or Pluripotent Stem Cells

Essentially any stem cell with the ability to differentiate along the mesodermal lineage ((e.g., an embryonic stem cell) and/or pluripotent stem cell (e.g., an induced pluripotent stem cell)) can be used to derive hepatic stellate cells in vitro. In one embodiment, the stem cells and/or pluripotent stem cells are human stem cells and/or human pluripotent stem cells. Methods for differentiation of such pluripotent or multipotent stem cells or progenitor cells to hepatic stellate cells is known in the art and/or can be performed by exposing the stem or pluripotent stem cells to conditions that mimic the developmental landscape during generation of hepatic stellate cells. For example, the stem or pluripotent cells can be exposed to a series of environments and growth factors/cytokines that can directly or step-wise generate hepatic stellate cells. There are a variety of different methods that can be performed during cell differentiation that will result in the generation of a hepatic stellate cell, and any one of such methods can be employed. That is, differentiation of stem or pluripotent cells to hepatic stellate cells is not limited by any method of differentiation, provided that the resulting hepatic stellate cells retain substantially similar functional properties to primary HSCs.

Embryonic Stem Cells: Embryonic stem cells and methods of their retrieval are well known in the art and are described, for example, in Trounson A O (Reprod Fertil Dev (2001) 13: 523), Roach M L (Methods Mol Biol (2002) 185: 1), and Smith A G (Annu Rev Cell Dev Biol (2001) 17:435). The term "embryonic stem cell" is used to refer to the pluripotent stem cells of the inner cell mass of the embryonic blastocyst (see e.g., U.S. Pat. Nos. 5,843,780, 6,200,806). Such cells can similarly be obtained from the inner cell mass of blastocysts derived from somatic cell nuclear transfer (see, for example, U.S. Pat. Nos. 5,945,577, 5,994,619, 6,235,970).

Cells derived from embryonic sources can include embryonic stem cells or stem cell lines obtained from a stem cell bank or other recognized depository institution. Other means of producing stem cell lines include methods comprising the use of a blastomere cell from an early stage embryo prior to formation of the blastocyst (at around the 8-cell stage). Such techniques correspond to the pre-implantation genetic diagnosis technique routinely practiced in assisted reproduction clinics. The single blastomere cell is co-cultured with established ES-cell lines and then separated from them to form fully competent ES cell lines.

Embryonic stem cells are considered to be undifferentiated when they have not committed to a specific differentiation lineage. Such cells display morphological characteristics that distinguish them from differentiated cells of embryo or adult origin. Undifferentiated embryonic stem (ES) cells are easily recognized by those skilled in the art, and typically appear in the two dimensions of a microscopic view in colonies of cells with high nuclear/cytoplasmic ratios and prominent nucleoli. In some embodiments, the hepatic stellate cells described herein are not derived from embryonic stem cells or any other cells of embryonic origin.

Adult Stem Cells: Adult stem cells are stem cells derived from tissues of a post-natal or post-neonatal organism or from an adult organism. An adult stem cell is structurally distinct from an embryonic stem cell not only in markers it does or does not express relative to an embryonic stem cell, but also by the presence of epigenetic differences, e.g., differences in DNA methylation patterns.

Induced Pluripotent Stem Cells (iPSCs): In some embodiments, the hepatic stellate cells described herein are derived from induced pluripotent stem cells (iPSCs). An advantage of using induced pluripotent stem cells is that the cells can be derived from the same subject to which the engineered HSCs are to be administered. That is, a somatic cell can be obtained from a subject, reprogrammed to an induced pluripotent stem cell, and then re-differentiated into a hepatic stellate cell to be engineered to a quiescent HSC for administration to the subject (e.g., autologous cells). Since the hepatic stellate cell progenitors are essentially derived from an autologous source, the risk of engraftment rejection or allergic responses is reduced compared to the use of cells from another subject or group of subjects. In some embodiments, the hepatic stellate cell progenitors are derived from non-autologous sources. In addition, the use of iPSCs negates the need for cells obtained from an embryonic source. Thus, in one embodiment, the stem cells used in the disclosed methods are not embryonic stem cells.

Although differentiation is generally irreversible under physiological contexts, several methods have been recently developed to reprogram somatic cells to induced pluripotent stem cells. Exemplary methods are known to those of skill in the art and are described briefly herein below. iPSCs resemble ES cells as they restore the pluripotency-associated transcriptional circuitry and much of the epigenetic landscape. In addition, iPSCs satisfy all the standard assays for pluripotency: specifically, in vitro differentiation into cell types of the three germ layers, teratoma formation, contribution to chimeras, germline transmission (Maherali and Hochedlinger, 2008), and tetraploid complementation (Woltjen et al., 2009).

As used herein, the term "reprogramming" refers to a process that alters or reverses the differentiation state of a differentiated cell (e.g., a somatic cell). Stated another way, reprogramming refers to a process of driving the differentiation of a cell backwards to a more undifferentiated or more primitive type of cell. It should be noted that placing many primary cells in culture can lead to some loss of fully differentiated characteristics. Thus, simply culturing such cells included in the term differentiated cells does not render these cells non-differentiated cells (e.g., undifferentiated cells) or pluripotent cells. The transition of a differentiated cell to pluripotency requires a reprogramming stimulus beyond the stimuli that lead to partial loss of differentiated character in culture. Reprogrammed cells also have the characteristic of the capacity of extended passaging without loss of growth potential, relative to primary cell parents, which generally have capacity for only a limited number of divisions in culture.

The term "reprogramming" is intended to be distinguished from the process of inducing quiescence of a hepatic stellate cell (e.g., modification of an activated hepatic stellate cell to a quiescent hepatic stellate cell), which is termed "quiescent reprogramming" herein.

A cell to be reprogrammed can be either partially or terminally differentiated prior to reprogramming. In some embodiments, reprogramming encompasses reversion of the differentiation state of a differentiated cell (e.g., a somatic cell) to a pluripotent state or a multipotent state. In some embodiments, reprogramming encompasses complete or partial reversion of the differentiation state of a differentiated cell (e.g., a somatic cell) to an undifferentiated cell (e.g., an embryonic-like cell). The resulting cells are referred to as "reprogrammed cells;" when the reprogrammed cells are pluripotent, they are referred to as "induced pluripotent stem cells (iPSCs or iPS cells)."

Reprogramming can involve alteration, e.g., reversal, of at least some of the heritable patterns of nucleic acid modification (e.g., methylation), chromatin condensation, epigenetic changes, genomic imprinting, etc., that occur during cellular differentiation. Reprogramming is distinct from simply maintaining the existing undifferentiated state of a cell that is already pluripotent or maintaining the existing less than fully differentiated state of a cell that is already a multipotent cell (e.g., a hematopoietic stem cell). Reprogramming is also distinct from promoting the self-renewal or proliferation of cells that are already pluripotent or multipotent. The specific reprogramming approach or method used to generate pluripotent stem cells from somatic cells is not critical to the methods and compositions described herein. Thus, any method that re-programs a somatic cell to the pluripotent phenotype would be appropriate for use in the methods described herein.

Reprogramming methodologies using defined combinations of transcription factors have been described for generating induced pluripotent stem cells. Yamanaka and Takahashi converted mouse somatic cells to ES cell-like cells with expanded developmental potential by the direct transduction of genes encoding Oct4, Sox2, Klf4, and c-Myc (Takahashi and Yamanaka, 2006).

Subsequent studies have shown that human iPS cells can be obtained using similar transduction methods (Lowry et al., 2008; Park et al., 2008; Takahashi et al., 2007; Yu et al., 2007b), and the transcription factor trio, OCT4, SOX2, and NANOG, has been established as the core set of transcription factors that govern pluripotency (Jaenisch and Young, 2008). The production of iPS cells can be achieved by the introduction of nucleic acid sequences encoding stem cell-associated genes into an adult, somatic cell, historically using viral vectors.

iPS cells can be generated or derived from terminally differentiated somatic cells, as well as from adult stem cells, or somatic stem cells. That is, a non-pluripotent progenitor cell can be rendered pluripotent or multipotent by reprogramming. In such instances, it may not be necessary to include as many reprogramming factors as required to reprogram a terminally differentiated cell. Further, reprogramming can be induced by the non-viral introduction of reprogramming factors, e.g., by introducing the proteins themselves, or by introducing nucleic acids that encode the reprogramming factors, or by introducing messenger RNAs that upon translation produce the reprogramming factors (see e.g., Warren et al., Cell Stem Cell, 2010 Nov. 5; 7(5):618-30). Reprogramming can be achieved by introducing a combination of nucleic acids encoding stem cell-associated genes including, for example Oct-4 (also known as Oct-3/4 or Pouf51), Sox1, Sox2, Sox3, Sox 15, Sox 18, NANOG, Klf1, Klf2, Klf4, Klf5, NR5A2, c-Myc, 1-Myc, n-Myc, Rem2, Tert, and LIN28. In one embodiment, reprogramming using the methods and compositions described herein can further comprise introducing one or more of Oct-3/4, a member of the Sox family, a member of the Klf family, and a member of the Myc family to a somatic cell.

In one embodiment, the methods and compositions described herein further comprise introducing one or more of each of Oct-4, Sox2, Nanog, c-MYC and Klf4 for reprogramming. As noted above, the exact method used for reprogramming is not necessarily critical to the methods and compositions described herein. However, where cells differentiated from the reprogrammed cells are to be used in, e.g., human therapy, in one embodiment the reprogramming is not effected by a method that alters the genome. Thus, in such embodiments, reprogramming is achieved, e.g., without the use of viral or plasmid vectors. In addition to the protein-based and the RNA-based methods (see e.g., Warren et al., supra), recent evidence indicates somatic cells can be re-programmed by e.g., exposure of the cells to unphysiological stress, e.g., in culture (see e.g., WO2013/163296, which is incorporated herein by reference in its entirety). These methods of re-programming may be preferred for cells to be used for therapeutic purposes, as they are less likely to provoke genomic damage likely to promote, e.g., cancer.

The efficiency of reprogramming (i.e., the number of reprogrammed cells) derived from a population of starting cells can be enhanced by the addition of various small molecules as shown by Shi, Y., et al (2008) Cell-Stem Cell 2:525-528, Huangfu, D., et al (2008) Nature Biotechnology 26(7):795-797, and Marson, A., et al (2008) Cell-Stem Cell 3:132-135. Thus, an agent or combination of agents that enhance the efficiency or rate of induced pluripotent stem cell production can be used in the production of patient-specific or disease-specific iPSCs. Some non-limiting examples of agents that enhance reprogramming efficiency include soluble Wnt, Wnt conditioned media, BIX-01294 (a G9a histone methyltransferase), PD0325901 (a MEK inhibitor), DNA methyltransferase inhibitors, histone deacetylase (HDAC) inhibitors, valproic acid, 5'-azacytidine, dexamethasone, suberoylanilide, hydroxamic acid (SAHA), vitamin C, and trichostatin (TSA), among others.

Other non-limiting examples of reprogramming enhancing agents include: Suberoylanilide Hydroxamic Acid (SAHA (e.g., MK0683, vorinostat) and other hydroxamic acids), BML-210, Depudecin (e.g., (−)-Depudecin), HC Toxin, (4-(1,3-Dioxo-1H,3H-benzo[de]isoquinolin-2-yl)-N-hydroxybutanamide), Phenylbutyrate (e.g., sodium phenylbutyrate) and Valproic Acid ((VPA) and other short chain fatty acids), Scriptaid, Suramin Sodium, Trichostatin A (TSA), APHA Compound 8, Apicidin, Sodium Butyrate, pivaloyloxymethyl butyrate (Pivanex, AN-9), Trapoxin B, Chlamydocin, Depsipeptide (also known as FR901228 or FK228), benzamides (e.g., CI-994 (e.g., N-acetyl dinaline) and MS-27-275), MGCD0103, NVP-LAQ-824, CBHA (m-carboxycinnaminic acid bishydroxamic acid), JNJ16241199, Tubacin, A-161906, proxamide, oxamflatin, 3-C1-UCHA (e.g., 6-(3-chlorophenylureido)caproic hydroxamic acid), AOE (2-amino-8-oxo-9,10-epoxydecanoic acid), CHAP31 and CHAP 50. Other reprogramming enhancing agents include, for example, dominant negative forms of the HDACs (e.g., catalytically inactive forms), siRNA inhibitors of the HDACs, and antibodies that specifically bind to the HDACs. Such inhibitors are available, e.g., from BIOMOL International, Fukasawa, Merck Biosciences, Novartis, Gloucester Pharmaceuticals, Aton Pharma, Titan Pharmaceuticals, Schering AG, Pharmion, MethylGene, and Sigma Aldrich.

To confirm the induction of pluripotent stem cells for use with the methods described herein, isolated clones can be tested for the expression of a stem cell marker. Such expression in a cell derived from a somatic cell identifies the cells as induced pluripotent stem cells. Stem cell markers can be selected from the non-limiting group including SSEA3, SSEA4, CD9, Nanog, Fbx15, Ecat1, Esg1, Eras, Gdf3, Fgf4, Cripto, Dax1, Zpf296, Slc2a3, Rex1, Utf1, and Nat1. In one embodiment, a cell that expresses Oct4 or Nanog is identified as pluripotent. Methods for detecting the expression of such markers can include, for example, RT-PCR and immunological methods that detect the presence of the encoded polypeptides, such as Western blots or flow cytometric analyses. In some embodiments, detection does not involve only RT-PCR, but also includes detection of protein markers. Intracellular markers may be best identified via RT-PCR, while cell surface markers are readily identified, e.g., by immunocytochemistry.

The pluripotent stem cell character of isolated cells can be confirmed by tests evaluating the ability of the iPSCs to differentiate to cells of each of the three germ layers. As one example, teratoma formation in nude mice can be used to evaluate the pluripotent character of the isolated clones. The cells are introduced to nude mice and histology and/or immunohistochemistry is performed on a tumor arising from the cells. The growth of a tumor comprising cells from all three germ layers, for example, further indicates that the cells are pluripotent stem cells.

Somatic Cells for reprogramming to iPSCs: Somatic cells, as that term is used herein, refer to any cells forming the body of an organism, excluding germline cells. Every cell type in the mammalian body—apart from the sperm and ova, the cells from which they are made (gametocytes) and undifferentiated stem cells—is a differentiated somatic cell. For example, internal organs, skin, bones, blood, and connective tissue are all made up of differentiated somatic cells.

Additional somatic cell types for use with the compositions and methods described herein include: a fibroblast (e.g., a primary fibroblast), a muscle cell (e.g., a myocyte), a cumulus cell, a neural cell, a mammary cell, a hepatocyte, a cardiomyocyte and a pancreatic islet cell. In some embodiments, the somatic cell is a primary cell line or is the progeny of a primary or secondary cell line. In some embodiments, the somatic cell is obtained from a human sample, e.g., a hair follicle, a blood sample, a biopsy (e.g., a skin biopsy or an adipose biopsy), a swab sample (e.g., an oral swab sample), and is thus a human somatic cell.

Some non-limiting examples of differentiated somatic cells include, but are not limited to, epithelial, endothelial, neuronal, adipose, cardiac, skeletal muscle, immune cells, hepatic, splenic, lung, circulating blood cells, gastrointestinal, renal, bone marrow, and pancreatic cells. In some embodiments, a somatic cell can be a primary cell isolated from any somatic tissue including, but not limited to brain, liver, lung, gut, stomach, intestine, fat, muscle, uterus, skin, spleen, endocrine organ, bone, etc. Further, the somatic cell can be from any mammalian species, with non-limiting examples including a murine, bovine, simian, porcine, equine, ovine, or human cell. In some embodiments, the somatic cell is a human somatic cell.

When reprogrammed cells are used for generation of hepatic stellate cells to be used in the therapeutic treatment of disease, it is desirable, but not required, to use somatic cells isolated from the patient being treated. In some embodiments, a method for selecting the reprogrammed cells from a heterogeneous population comprising reprogrammed cells and somatic cells they were derived or generated from can be performed by any known means. For example, a drug resistance gene or the like, such as a selectable marker gene can be used to isolate the reprogrammed cells using the selectable marker as an index. It is emphasized that such a selectable marker is not required—that is, in some embodiments reprogrammed pluripotent stem cells can be identified on the basis of morphology. See, e.g., US 2010/0184051. It is noted herein that reprogramming can be performed using any means known in the art. That is, the specific reprogramming approach is not critical for the methods or processes of generating or engineering hepatic stellate cells as described herein.

Reprogrammed somatic cells as disclosed herein can express any number of pluripotent cell markers, including: alkaline phosphatase (AP); ABCG2; stage specific embryonic antigen-1 (SSEA-1); SSEA-3; SSEA-4; TRA-1-60; TRA-1-81; Tra-2-49/6E; ERas/ECAT5, E-cadherin; b-III-tubulin; a-smooth muscle actin (a-SMA); fibroblast growth factor 4 (Fgf4), Cripto, Dax1; zinc finger protein 296 (Zfp296); N-acetyltransferase-1 (Nat1); (ES cell associated transcript 1 (ECAT1); ESG1/DPPA5/ECAT2; ECAT3; ECAT6; ECAT7; ECAT8; ECAT9; ECAT10; ECAT15-1; ECAT15-2; Fth117; Sa114; undifferentiated embryonic cell transcription factor (Utf1); Rex1; p53; G3PDH; telomerase, including TERT; silent X chromosome genes; Dnmt3a; Dnmt3b; TRIM28; F-box containing protein 15 (Fbx15); Nanog/ECAT4; Oct3/4; Sox2; Klf4; c-Myc; Esrrb; TDGF1; GABRB3; Zfp42, FoxD3; GDF3; CYP25A1; developmental pluripotency-associated 2 (DPPA2); T-cell lymphoma breakpoint 1 (Tc11); DPPA3/Stella; DPPA4; other general markers for pluripotency, etc. Other markers can include Dnmt3L; Sox15; Stat3; Grb2; b-catenin, and Bmi1. Such cells can also be characterized by the down-regulation of markers characteristic of the somatic cell from which the induced pluripotent stem cell is derived.

Pharmaceutically Acceptable Carriers

The methods of administering one or more miRNAs, miRNA mimics, nucleic acid sequences encoding one or more miRNAs or quiescent, engineered HSCs to a subject as described herein involve the use of therapeutic compositions comprising such miRNAs, miRNA mimics, nucleic acid sequences encoding one or more miRNAs or quiescent, engineered HSCs. Therapeutic compositions can contain a physiologically tolerable carrier together with the cell composition and optionally at least one additional bioactive agent as described herein, dissolved or dispersed therein as an active ingredient. In a preferred embodiment, the therapeutic composition is not substantially immunogenic when administered to a mammal or human patient for therapeutic purposes, unless so desired. As used herein, the terms "pharmaceutically acceptable", "physiologically tolerable" and grammatical variations thereof, as they refer to compositions, carriers, diluents and reagents, are used interchangeably and represent that the materials are capable of administration to, into, or upon a mammal without the production of undesirable physiological effects such as nausea, dizziness, gastric upset, transplant rejection, allergic reaction, and the like. The preparation of a composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared.

In general, the engineered hepatic stellate cells described herein are administered as a suspension with a pharmaceutically acceptable carrier. One of skill in the art will recognize that a pharmaceutically acceptable carrier to be used in a cell composition will not include buffers, compounds, cryopreservation agents, preservatives, or other agents in amounts that substantially interfere with the viability of the cells to be delivered to the subject. A formulation comprising cells can include e.g., osmotic buffers that permit cell membrane integrity to be maintained, and optionally, nutrients to maintain cell viability or enhance engraftment upon administration. Such formulations and suspensions are known to those of skill in the art and/or can be adapted for use with the hepatic stellate cells as described herein using routine experimentation. In one embodiment, the engineered hepatic stellate cells are formulated for direct injection into the liver (e.g., intrahepatic injection).

An miRNA, nucleic acid encoding an miRNA, or a cell composition can also be emulsified or presented as a liposome composition, provided that the emulsification procedure does not adversely affect miRNA/nucleic acid stability or cell viability. The miRNA, nucleic acids encoding such miRNAs, engineered cells and any other desired active ingredient can be mixed with excipients which are pharmaceutically acceptable and compatible with the active ingredient and in amounts suitable for use in the therapeutic methods described herein.

Additional agents included in the composition as described herein can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active compound used in the cell compositions as described herein that is effective in the treatment of a particular disorder or condition will depend on the nature of the disorder or condition, and can be determined by standard clinical techniques.

Cell Therapy

Cell based therapy includes the administration of cells to a subject or directly to a diseased liver in order to reestablish, at the desired location, a structurally and functionally intact unit. In some embodiments, cells can be transplanted by forming a hepatic-like tissue structure, which is promoted by seeding cells onto a porous, fibrous or hydrogel scaffold. Besides using scaffolds, techniques have also been developed to engineer scaffold-free tissues, composed only of cells and the matrix they secrete, circumventing common problems occurring when using scaffolds, as residual polymer fragments can interfere with the cell organization and an inherent weakness of tissue engineered vessel.

Essentially any liver disease, disorder or injury associated with activated hepatic stellate cells can be treated using the methods and compositions described herein. In one embodiment, the liver disease, disorder or injury is associated with hepatic fibrosis, such that administration of the compositions described herein will replace lost liver tissue and/or function. Optionally, administration of the compositions described herein can completely or partially reverse existing liver fibrosis. Examples of liver diseases, disorders, or injuries that can lead to liver fibrosis and/or liver failure include, but are not limited to, α1 anti-trypsin deficiency, autoimmune hepatitis, biliary atresia, cirrhosis, non-alcoholic fatty liver disease, hepatic cancer, hepatic fibrosis, hepatic steatosis (fatty liver disease), galactosemia, gallstones, Gilbert's syndrome, hemochromatosis, lysosomal acid lipase deficiency, primary biliary cholangitis, porphyria, Reye's syndrome, sarcoidosis, toxic hepatitis, type 1 glycogen storage disease, tyrosinemia, viral hepatitis A, viral hepatitis B, viral hepatitis C, or Wilson disease. In one embodiment, non-alcoholic fatty liver disease can be treated with engineered hepatic stellate cells, as described herein. In one embodiment, the liver disorder is hepatotoxicity.

In one embodiment, the hepatic stellate cells can be administered as a graft to the subject by implantation. The graft may include an autograft, an allograft, and a xenograft. The term autograft as used in the present invention describes the transfer of tissues or cells within the same mammal. Allografts, as that term is used herein, describe the transfer of tissues or cells between two genetically dissimilar mammals of the same species. The term xenograft as used herein describes the transfer of tissues or cells between two mammals of different species.

A hepatic stellate cell graft can be administered using any technique capable of introducing the combination into the mammal. Such techniques can include, for example, through a catheter, subcutaneous injection, or through a small incision in the mammal's abdomen. In one embodiment, the HSC graft is administered to the mammal's liver. An immunosuppressive agent can be administered to the mammal to further suppress rejection of the transplanted graft. Examples of immunosuppressive agents or anti-rejection drugs that can be administered to the mammal include dacliximab, sirolimus, tacrolimus and cyclosporine. The amount of graft cells included in the combination can be a therapeutically effective amount to treat a disorder and/or repair a defect in the mammal.

Treatment with miRNA(s), miRNA Mimic(s) or Nucleic Acids Encoding miRNA(s)

The delivery of an miRNA to a subject in need thereof can be achieved in a number of different ways. In vivo delivery can be performed by administering a composition comprising an miRNA, e.g., miR-412 and/or miR-15a, to a subject. Alternatively, delivery can be performed by administering one or more vectors that encode and direct the expression of the miRNA.

In general, any method of delivering a nucleic acid molecule can be adapted for use with an miRNA (see e.g., Akhtar S. and Julian R L. (1992) Trends Cell. Biol. 2(5): 139-144 and WO94/02595, which are incorporated herein by reference in their entireties). However, successful delivery of an miRNA molecule in vivo requires design of an miRNA, miRNA mimic or a nucleic acid encoding an miRNA that ensures biological stability of the delivered molecule, prevention of non-specific effects, and accumulation of the delivered molecule in the target tissue. The non-specific effects of an miRNA can be minimized by local administration, for example by direct injection or implantation into a tissue (as a non-limiting example, liver). Local administration to a treatment site maximizes local concentration of the agent, limits the exposure of the agent to systemic tissues that may otherwise be harmed by the agent or that may degrade the agent, and permits a lower total dose of the miRNA molecule to be administered. For administering an miRNA systemically for the treatment of a disease, the RNA can be modified or alternatively delivered using a drug delivery system; both methods act to prevent the rapid degradation of the miRNA by enzymes in vivo. Modification of the miRNA or the pharmaceutical carrier can also permit targeting of the miRNA composition to the target tissue and avoid undesirable off-target effects. miRNA molecules can be modified by chemical conjugation to lipophilic groups such as cholesterol to enhance cellular uptake and prevent degradation. In an alternative embodiment, the miRNA can be delivered using drug delivery systems such as a nanoparticle, a dendrimer, a polymer, liposomes, or a cationic delivery system. Positively charged cationic delivery systems can facilitate binding of an miRNA molecule and also enhance interactions at the negatively charged cell membrane to permit efficient uptake of an miRNA by the cell. Cationic lipids, dendrimers, or polymers can either be bound to an miRNA, or induced to form a vesicle or micelle that encases an miRNA. The formation of vesicles or micelles further prevents degradation of the miRNA when administered systemically. Methods for making and administering cationic-miRNA complexes are well within the abilities of one skilled in the art.

Administration and Efficacy

Provided herein are methods for treating a liver disease, a liver disorder, or a liver injury involving or pre-disposing an individual to hepatic fibrosis, the method comprising administering quiescent hepatic stellate cells to a subject in need thereof.

As used herein, the terms "administering," "introducing" and "transplanting" are used interchangeably in the context of the placement of cells, e.g., quiescent hepatic stellate cells, as described herein into a subject, by a method or route which results in at least partial localization of the introduced cells at a desired site, such as a site of injury or repair, such that a desired effect(s) is produced. The cells e.g., quiescent hepatic stellate cells can be implanted directly into damaged liver tissue, or alternatively be administered by any appropriate route which results in delivery to a desired location in the subject where at least a portion of the implanted cells or components of the cells remain viable. The period of viability of the cells after administration to a subject can be as short as a few hours, e.g., twenty-four hours, to a few days, to as long as several years or more, i.e., long-term engraftment.

In one embodiment, quiescent hepatic stellate cells are administered to a subject having detectable liver disease, disorder, or injury. Measured or measurable parameters include clinically detectable markers of disease, for example, elevated or depressed levels of a clinical or biological marker (e.g., increased liver enzymes in the serum), as well as parameters related to a clinically accepted scale of symptoms or markers for a disease or disorder. It will be understood, however, that the total usage of the compositions and formulations as disclosed herein will be decided by the attending physician within the scope of sound medical judgment. The exact amount required will vary depending on factors such as the type of disease being treated.

In one embodiment, quiescent hepatic stellate cells are prophylactically administered to a subject having known risk factors for liver disease, disorder, or injury, in order to prevent the disease, disorder, or injury. In another embodiment, quiescent hepatic stellate cells are administered to a subject with existing liver fibrosis of any severity, wherein the quiescent HSCs can partially or completely reverse the existing liver fibrosis and/or restore normal liver function.

The term "effective amount" as used herein can refer to the amount of a population of quiescent hepatic stellate cells needed to alleviate at least one or more symptoms of the liver injury or the liver disease or disorder, and relates to a sufficient amount of a composition to provide the desired effect, e.g., treat a subject having damaged liver tissue. The term "therapeutically effective amount" therefore refers to an amount of quiescent hepatic stellate cells or a composition comprising quiescent hepatic stellate cells that is sufficient to promote a particular effect when administered to a typical subject, such as one who has or is at risk for a liver disease or disorder. An effective amount as used herein would also include an amount sufficient to prevent or delay the development of a symptom of the disease, alter the course of a symptom disease (for example but not limited to, slow the progression of a symptom of the disease), or reverse a symptom of the disease. It is understood that for any given case, an appropriate "effective amount" can be determined by one of ordinary skill in the art using routine experimentation.

In some embodiments, the subject is first diagnosed as having a disease or disorder affecting the liver tissue prior to administering the cells according to the methods described herein (e.g., as a result of an hepatic fibrosis). In some embodiments, the subject is first diagnosed as being at risk of developing liver disease or disorder prior to administering the cells (e.g., a subject having early symptoms of liver fibrosis).

For use in the various aspects described herein, an effective amount of quiescent hepatic stellate cells, comprises at least $1\times10^4$ quiescent hepatic stellate cells, at least $5\times10^4$ quiescent hepatic stellate cells, at least $1\times10^5$, at least $5\times10^5$, at least $1\times10^6$ quiescent hepatic stellate cells, at least $5\times10^6$ quiescent hepatic stellate cells, at least $1\times10^7$ quiescent hepatic stellate cells, at least $2\times10^7$ quiescent hepatic stellate cells, at least $3\times10^7$ quiescent hepatic stellate cells, at least $4\times10^7$ quiescent hepatic stellate cells, at least $5\times10^7$ quiescent hepatic stellate cells, at least $6\times10^7$ quiescent hepatic stellate cells, at least $7\times10^7$ quiescent hepatic stellate cells, at least $8\times10^7$ quiescent hepatic stellate cells, at least $9\times10^7$ quiescent hepatic stellate cells, at least $1\times10^8$ quiescent hepatic stellate cells, at least $2\times10^8$ quiescent hepatic stellate cells, at least $3\times10^8$ quiescent hepatic stellate cells, at least $4\times10^8$ quiescent hepatic stellate cells, at least $5\times10^8$ quiescent hepatic stellate cells, at least $6\times10^8$ quiescent hepatic stellate cells, at least $7\times10^8$ quiescent hepatic stellate cells, at least $8\times10^8$ quiescent hepatic stellate cells, at least $9\times10^8$ quiescent hepatic stellate cells, at least $1\times10^9$ quiescent hepatic stellate cells, at least $2\times10^9$ quiescent hepatic stellate cells, at least $3\times10^9$ quiescent hepatic stellate cells, at least $4\times10^9$ quiescent hepatic stellate cells, at least $5\times10^9$ quiescent hepatic stellate cells, at least $6\times10^9$ quiescent hepatic stellate cells, at least $7\times10^9$ quiescent hepatic stellate cells, at least $8\times10^9$ quiescent hepatic stellate cells, at least $9\times10^9$ quiescent hepatic stellate cells, at least $1\times10^{10}$ quiescent hepatic stellate cells at least $2\times10^{10}$ quiescent hepatic stellate cells, at least $3\times10^{10}$ quiescent hepatic stellate cells, at least $4\times10^{10}$ quiescent hepatic stellate cells, at least $5\times10^{10}$ quiescent hepatic stellate cells, at least $6\times10^{10}$ quiescent hepatic stellate cells, at least $7\times10^{10}$ quiescent hepatic stellate cells, at least $8\times10^{10}$ quiescent hepatic stellate cells, at least $9\times10^{10}$ quiescent hepatic stellate cells, or multiples thereof. Without wishing to be bound by theory, engineered hepatic stellate cells comprising permanent expression of miR-412 and/or miR-15a (i.e., such nucleic acids are integrated into the host genome) can be administered in lower numbers due to their ability to generate identical daughter cells by cell division. Thus, administration of engineered HSC cells in number as low as 10,000 is specifically contemplated for use with the methods described herein. For example, at least $1\times10^4$ quiescent hepatic stellate cells, at least $2\times10^4$ quiescent hepatic stellate cells, at least $3\times10^4$ quiescent hepatic stellate cells, at least $4\times10^4$ quiescent hepatic stellate cells, at least $5\times10^4$ quiescent hepatic stellate cells, at least $6\times10^4$ quiescent hepatic stellate cells, at least $7\times10^4$ quiescent hepatic stellate cells, at least $8\times10^4$ quiescent hepatic stellate cells, at least $9\times10^4$ quiescent hepatic stellate cells, at least $1\times10^5$ quiescent hepatic stellate cells, at least $2\times10^5$ quiescent hepatic stellate cells, at least $3\times10^5$ quiescent hepatic stellate cells, at least $4\times10^5$ quiescent hepatic stellate cells, at least $5\times10^5$ quiescent hepatic stellate cells, at least $6\times10^5$ quiescent hepatic stellate cells, at least $7\times10^5$ quiescent hepatic stellate cells, at least $8\times10^5$ quiescent hepatic stellate cells, or at least $9\times10^5$ quiescent hepatic stellate cells.

The quiescent hepatic stellate cells can be derived from one or more donors, or can be obtained from an autologous source. In some embodiments of the aspects described herein, the hepatic progenitor cells are expanded in culture prior to differentiation to quiescent hepatic stellate cells and administration to a subject in need thereof.

The pharmaceutical compositions featured herein are administered in dosages sufficient to induce quiescence of a hepatic stellate cell, as determined by monitoring the cells for the reappearance of lipid droplets, decrease in collagen secretion, or decreased expression of gene markers of HSC activation. A suitable dose of miRNA can be in the range of 0.01 to 200.0 milligrams per kilogram body weight of the recipient per day, generally in the range of 1 to 50 mg per kilogram body weight per day. For example, the miRNA can be administered at 0.05 mg/kg, 0.5 mg/kg, 1 mg/kg, 1.5 mg/kg, 2 mg/kg, 3 mg/kg, 10 mg/kg, 20 mg/kg, 30 mg/kg, 40 mg/kg, or 50 mg/kg per single dose. The pharmaceutical composition may be administered once daily, or the miRNA may be administered as two, three, or more sub-doses at appropriate intervals throughout the day or even using continuous infusion or delivery through a controlled release formulation. In that case, the miRNA contained in each sub-dose can be correspondingly smaller in order to achieve the total daily dosage. The dosage unit can also be compounded for delivery over several days, e.g., using a conventional sustained release formulation which provides sustained release of the miRNA over a several day period. Sustained release formulations are well known in the art and are particularly useful for delivery of agents at a particular site, such as could be used with the methods and compositions as described herein. In this embodiment, the dosage unit contains a corresponding multiple of the daily dose. It is specifically contemplated herein that the effect of a single dose of an miRNA, miRNA mimic or nucleic acid encoding an miRNA as described herein can be long lasting, such that subsequent doses are administered at not more than 3, 4, or 5 day intervals, or at not more than 1, 2, 3, or 4 week intervals.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual miRNAs encompassed by the invention can be made using conventional methodologies or on the basis of in vivo testing using an appropriate animal model, as described elsewhere herein.

Exemplary modes of administration for use in the methods described herein include, but are not limited to, injection, intrahepatic infusion, and implantation (with or without a scaffold material). "Injection" includes, without limitation, intravenous, parenteral and intrahepatic administration. The phrases "parenteral administration" and "administered parenterally" as used herein, refer to modes of administration other than enteral and topical administration, usually by injection, and includes, without limitation, intravenous, intrahepatic intraperitoneal, intramuscular, intra-arterial, intradermal, transtracheal, and subcutaneous administration.

In some embodiments, an effective amount of quiescent hepatic stellate cells is administered to a subject by systemic administration, such as intravenous administration or by direct injection to the liver.

The phrases "systemic administration," "administered systemically", "peripheral administration" and "administered peripherally" as used herein refer to the administration of a population of quiescent hepatic stellate cells other than directly into a target site, tissue, or organ, such as the liver, such that it enters, instead, the subject's circulatory system and, thus, is subject to metabolism and other like processes.

In some embodiments, additional agents to aid in treatment of the subject can be administered before or following treatment with the quiescent hepatic stellate cells described herein. Such additional agents can be used to prepare the liver tissue for administration of the quiescent hepatic stellate cells. Alternatively the additional agents can be administered after the quiescent hepatic stellate cells to support the engraftment and growth of the administered cell in the damaged liver.

The efficacy of treatment can be determined by the skilled clinician. However, a treatment is considered "effective treatment," as the term is used herein, if any one or all of the symptoms, or other clinically accepted symptoms or markers of liver disease, liver injury and/or a liver disorder are reduced, e.g., by at least 10% following treatment with a composition comprising quiescent hepatic stellate cells as described herein. Methods of measuring these indicators are known to those of skill in the art and/or described herein.

Indicators of liver disease or liver disorder, or liver injury include functional indicators, e.g., serum or urine bilirubin levels and test, alanine transaminase test, albumin test, etc.), as well as biochemical indicators. Other indicators of liver fibrosis are clinically relevant symptoms such as liver pain, jaundice, need for hospitalization, etc.

Scaffold Compositions

Biocompatible synthetic, natural, as well as semi-synthetic polymers, can be used for synthesizing polymeric particles that can be used as a scaffold material. In general, for the practice of the methods described herein, it is preferable that a scaffold biodegrades such that the quiescent hepatic stellate cells can be isolated from the polymer prior to implantation or such that the scaffold degrades over time in a subject and does not require removal. Thus, in one embodiment, the scaffold provides a temporary structure for growth and/or delivery of quiescent hepatic stellate cells to a subject in need thereof. In some embodiments, the scaffold permits quiescent hepatic stellate cells to be grown in a shape suitable for transplantation or administration into a subject in need thereof, thereby permitting removal of the scaffold prior to implantation and reducing the risk of rejection or allergic response initiated by the scaffold itself.

Examples of polymers which can be used include natural and synthetic polymers, although synthetic polymers are preferred for reproducibility and controlled release kinetics. Synthetic polymers that can be used include biodegradable polymers such as poly(lactide) (PLA), poly(glycolic acid) (PGA), poly(lactide-co-glycolide) (PLGA), and other polyhydroxyacids, poly(caprolactone), polycarbonates, polyamides, polyanhydrides, polyphosphazene, polyamino acids, polyortho esters, polyacetals, polycyanoacrylates and biodegradable polyurethanes; non-biodegradable polymers such as polyacrylates, ethylene-vinyl acetate polymers and other acyl-substituted cellulose acetates and derivatives thereof, polyurethanes, polystyrenes, polyvinyl chloride, polyvinyl fluoride, poly(vinyl imidazole), chlorosulphonated polyolefins, and polyethylene oxide. Examples of biodegradable natural polymers include proteins such as albumin, collagen, fibrin, silk, synthetic polyamino acids and prolamines; polysaccharides such as alginate, heparin; and other naturally occurring biodegradable polymers of sugar units. Alternately, combinations of the aforementioned polymers can be used.

PLA, PGA and PLA/PGA copolymers are particularly useful for forming biodegradable scaffolds. PLA polymers are usually prepared from the cyclic esters of lactic acids. Both L(+) and D(−) forms of lactic acid can be used to prepare the PLA polymers, as well as the optically inactive DL-lactic acid mixture of D(−) and L(+) lactic acids. Methods of preparing polylactides are well documented in the patent literature. The following U.S. Patents, the teachings of which are hereby incorporated by reference, describe in detail suitable polylactides, their properties and their preparation: U.S. Pat. No. 1,995,970 to Dorough; U.S. Pat. No. 2,703,316 to Schneider; U.S. Pat. No. 2,758,987 to Salzberg; U.S. Pat. No. 2,951,828 to Zeile; U.S. Pat. No. 2,676,945 to Higgins; and U.S. Pat. Nos. 2,683,136; 3,531,561 to Trehu. PGA is a homopolymer of glycolic acid (hydroxyacetic acid). In the conversion of glycolic acid to poly(glycolic acid), glycolic acid is initially reacted with itself to form the cyclic ester glycolide, which in the presence of heat and a catalyst is converted to a high molecular weight linear-chain polymer. PGA polymers and their properties are described in more detail in "Cyanamid Research Develops World's First Synthetic Absorbable Suture", Chemistry and Industry, 905 (1970).

Fibers can be formed by melt-spinning, extrusion, casting, or other techniques well known in the polymer processing area. Preferred solvents, if used to remove a scaffold prior to implantation, are those which are completely removed by the processing or which are biocompatible in the amounts remaining after processing.

Polymers for use in the matrix should meet the mechanical and biochemical parameters necessary to provide adequate support for the cells with subsequent growth and proliferation. The polymers can be characterized with respect to mechanical properties such as tensile strength using an Instron tester, for polymer molecular weight by gel permeation chromatography (GPC), glass transition temperature by differential scanning calorimetry (DSC) and bond structure by infrared (IR) spectroscopy.

Scaffolds can be of any desired shape and can comprise a wide range of geometries that are useful for the methods described herein. A non-limiting list of shapes includes, for example, hollow particles, tubes, sheets, cylinders, spheres, and fibers, among others. The shape or size of the scaffold should not substantially impede cell growth, cell differentiation, cell proliferation or any other cellular process, nor should the scaffold induce cell death via e.g., apoptosis or necrosis. In addition, care should be taken to ensure that the scaffold shape permits appropriate surface area for delivery of nutrients from the surrounding medium to cells in the population, such that cell viability is not impaired. The scaffold porosity can also be varied as desired by one of skill in the art.

In some embodiments, attachment of the cells to a polymer is enhanced by coating the polymers with compounds such as basement membrane components, agar, agarose, gelatin, gum arabic, collagens types I, II, III, IV, and V, fibronectin, laminin, glycosaminoglycans, polyvinyl alcohol, mixtures thereof, and other hydrophilic and peptide attachment materials known to those skilled in the art of cell culture or tissue engineering. Examples of a material for coating a polymeric scaffold include polyvinyl alcohol and collagen.

In some embodiments it can be desirable to add bioactive molecules to the scaffold. In one embodiment, the bioactive factors include growth factors. Examples of growth factors include platelet derived growth factor (PDGF), transforming growth factor alpha or beta (TGFα or TGFβ), bone morphogenic protein 4 (BMP4), fibroblastic growth factor 7 (FGF7), fibroblast growth factor 10 (FGF10), epidermal growth factor (EGF), or vascular endothelium growth factor (VEGF), some of which are also angiogenic factors.

These factors are known to those skilled in the art and are available commercially or described in the literature. Bioactive molecules can be incorporated into the scaffold (e.g., matrix) and released over time by diffusion and/or degradation of the matrix, or they can be suspended with the cell suspension.

Screening Assays

The methods and compositions described herein are useful to screen for agents for inducing quiescent hepatic stellate cells or for the treatment of a liver disease or disorder.

In some embodiments, the quiescent hepatic stellate cells derived using the methods described herein can be used in methods, assays, systems and kits to develop specific in vitro assays. Such assays for drug screening and toxicology studies have an advantage over existing assays because they are of human origin, and do not require immortalization of cell lines, nor do they require tissue from cadavers, which poorly reflect the physiology of normal human cells. For example, the methods, assays, systems, and kits described herein can be used to identify and/or test agents that can promote liver function and/or liver metabolism. In addition to, or alternatively, the methods, assays, systems, and kits can be used to identify and/or test for agents useful in treating a liver disease or liver disorder, or for preventing/treating a liver injury. In certain embodiments, activated HSCs can be used for testing of agents that induce quiescence and their efficacy compared to the quiescent, engineered hepatic stellate cells described herein.

Accordingly, provided herein are methods for screening a test compound for biological activity, the method comprising (a) contacting an activated hepatic stellate cells as described herein with a test compound and (b) determining any effect of the compound on the quiescent/activation status of the cell. In one embodiment, the screening method further comprises generating quiescent hepatic stellate cells as disclosed herein. The effect on the cell can be one that is observable directly or indirectly by use of physical properties of the cell and reporter molecules.

As used herein, the term "biological activity" or "bioactivity" refers to the ability of a test compound to affect a biological sample. Biological activity can include, without limitation, elicitation of a stimulatory, inhibitory, regulatory, toxic or lethal response in a biological assay. For example, a biological activity can refer to the ability of a compound to modulate the effect of an enzyme, block a receptor, stimulate a receptor, modulate the expression level of one or more genes, modulate cell proliferation, modulate cell division, modulate cell metabolism, modulate differentiation, modulate cell morphology, modulate contractile function, or a combination thereof. In some instances, a biological activity can refer to the ability of a test compound to produce a toxic effect in a biological sample.

As used herein, the term "test compound" or "candidate agent" refers to an agent or collection of agents (e.g., compounds) that are to be screened for their ability to have an effect on the cell. Test compounds can include a wide variety of different compounds, including chemical compounds, mixtures of chemical compounds, e.g., polysaccharides, small organic or inorganic molecules (e.g., molecules having a molecular weight less than 2000 Daltons, less than 1000 Daltons, less than 1500 Dalton, less than 1000 Daltons, or less than 500 Daltons), biological macromolecules, e.g., peptides, proteins, peptide analogs, and analogs and derivatives thereof, peptidomimetics, nucleic acids, nucleic acid analogs and derivatives, an extract made from biological materials such as bacteria, plants, fungi, or animal cells or tissues, naturally occurring or synthetic compositions.

Depending upon the particular embodiment being practiced, the test compounds can be provided free in solution, or can be attached to a carrier, or a solid support, e.g., beads. A number of suitable solid supports can be employed for immobilization of the test compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, polyaminemethylvinylether maleic acid copolymer, glass beads, amino acid copolymer, ethylene-maleic acid copolymer, nylon, silk, etc. Additionally, for the methods described herein, test compounds can be screened individually, or in groups. Group screening is particularly useful where hit rates for effective test compounds are expected to be low such that one would not expect more than one positive result for a given group.

A number of small molecule libraries are known in the art and commercially available. These small molecule libraries can be screened using the screening methods described herein. A chemical library or compound library is a collection of stored chemicals that can be used in conjunction with the methods described herein to screen candidate agents for a particular effect. A chemical library comprises information regarding the chemical structure, purity, quantity, and physiochemical characteristics of each compound. Compound libraries can be obtained commercially, for example, from Enzo Life Sciences™, Aurora Fine Chemicals™, Exclusive Chemistry Ltd.™, ChemDiv, ChemBridge™, TimTec Inc.™, AsisChem™, and Princeton Biomolecular Research™, among others.

Without limitation, the compounds can be tested at any concentration that can exert an effect on the cells relative to a control over an appropriate time period. In some embodiments, compounds are tested at concentrations in the range of about 0.01 nM to about 100 mM, about 0.1 nM to about 500 µM, about 0.1 µM to about 20 µM, about 0.1 µM to about 10 µM, or about 0.1 µM to about 5 µM.

The compound screening assay can be used in a high through-put screen. High through-put screening is a process in which libraries of compounds are tested for a given activity. High through-put screening seeks to screen large numbers of compounds rapidly and in parallel. For example, using microtiter plates and automated assay equipment, a laboratory can perform as many as 100,000 assays per day, or more, in parallel.

The compound screening assays described herein can involve more than one measurement of the cell or reporter function (e.g., measurement of more than one parameter and/or measurement of one or more parameters at multiple points over the course of the assay). Multiple measurements can allow for following the biological activity over incubation time with the test compound. In one embodiment, the reporter function is measured at a plurality of times to allow monitoring of the effects of the test compound at different incubation times.

The screening assay can be followed by a subsequent assay to further identify whether the identified test compound has properties desirable for the intended use. For example, the screening assay can be followed by a second assay selected from the group consisting of measurement of any of: bioavailability, toxicity, or pharmacokinetics, but is not limited to these methods.

Such a toxicity screening assay is particularly well-suited for determining a subject's susceptibility to hepatotoxicity from a particular drug. Thus in some embodiments, the assay and/or method comprises the steps of obtaining a biological sample from a subject (e.g., a somatic cell), reprogramming the cells in the biological sample to an iPSC (as necessary), inducing differentiation to hepatic stellate cells, and inducing the quiescent hepatic stellate cells as described herein. In such embodiments, a subject can be previously determined to have e.g., α1 anti-trypsin deficiency, autoimmune hepatitis, biliary atresia, cirrhosis, non-alcoholic fatty liver disease, hepatic cancer, hepatic fibrosis, hepatic steatosis (fatty liver disease), galactosemia, gallstones, Gilbert's syndrome, hemochromatosis, lysosomal acid lipase deficiency, primary biliary cholangitis, porphyria, Reye's syndrome, sarcoidosis, toxic hepatitis, type 1 glycogen storage disease, tyrosinemia, viral hepatitis A, viral hepatitis B, viral hepatitis C, or Wilson disease All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 4$^{th}$ ed., J. Wiley & Sons (New York, NY 2012); March, *Advanced Organic Chemistry Reactions, Mechanisms and Structure* 5$^{th}$ ed., J. Wiley & Sons (New York, NY 2001); and Sambrook and Russel, *Molecular Cloning: A Laboratory Manual* 4th ed., Cold Spring Harbor Laboratory Press (Cold Spring Harbor, NY 2012); provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

EXAMPLES

Example 1: Use of miRNAs to Treat and/or Prevent Liver Disease (e.g., NAFLD)

Non-alcoholic fatty liver disease (NAFLD) is the most common hepatic disorder in industrialized nations. It is predicted that in the coming decades, it will become the most common cause of end-stage liver disease, hepatic transplant, and hepatocellular carcinoma in the developed world. In the United States, 80 million people are estimated to be affected due to the high prevalence of NAFLD risk factors including obesity, diabetes, and hyperlipidemia. Given that reducing risk factors for NAFLD is currently the main mode of management and that most patients have difficult time avoiding those risk factors, the unmet need for treating this common but serious hepatic disease is obvious. Thus, developing effective therapies for NAFLD is of utmost importance.

Provided herein are novel biologic therapies for NAFLD using microRNAs (miRNAs). The miRNA therapy for NAFLD can target relatively healthy patients with known risk factors for NAFLD and early evidence of liver disease. It can reduce steatosis, hepatitis, and fibrosis that can lead to end-stage liver disease and organ failure resulting from NAFLD.

miRNA therapy can be used alone or in conjunction with the current standard of care, which is avoidance or reduction of risk factors. Risk factors for NAFLD can include obesity, diabetes, high cholesterol, high triglycerides, poor diet/eating habits, or rapid weight loss. As such, current lifestyle modifications used in the treatment of NAFLD can include exercise, healthy dietary changes, reduce or eliminate alcohol consumption, and medication to control levels of triglycerides, blood glucose, and cholesterol.

The miRNA therapies described herein can be sued to promote hepatic stellate cells (HSCs) of the liver to remain in, or revert back, to the state of quiescence, since their activation is essential and required for fibrotic progression in NAFLD. Prior to the the studies described herein, few attempts have been made to exploit the primary pathophysiologic role of HSCs in fibrogenesis to discover novel therapies. miRNAs are known to have the ability influence an entire cellular program by targeting multiple genes, which led us to test their ability to induce quiescence in HSCs. The study described herein screened for miRNAs that force activated HSCs to become quiescent. Several candidates were identified that induce the reversion of HSCs back to quiescence from the activated form.

It is contemplated herein that the identified miRNAs described herein can be translated to the treatment and/or prevention of hepatic steatosis and inflammation, for example, in a NAFLD animal model and in humans. It is further contemplated herein that such miRNAs can be used as therapeutic agents to regulate HSCs and decrease liver fibrosis.

The studies provided herein define key molecular pathways utilized by miRNAs in determining HSC activation status and identify miRNAs that can prevent or decrease hepatic steatosis, inflammation, and fibrosis in a mouse model of NAFLD. Also provided herein is data relating to the identification of direct targets of the candidate miRNAs that revert activated HSCs back to quiescence, an treatment of a mouse model of NAFLD with the candidate miRNAs that revert activated HSCs to quiescence.

Deep RNA sequencing can be used to assess the gene expression of three HSC groups: 1) quiescent HSCs freshly harvested from control mice, 2) activated HSCs, 3) HSCs that were once activated but reverted to quiescence after the treatment with candidate miRNAs. Any coding genes that are significantly downregulated in set 3 compared to set 2 and are predicted to be direct targets of transfected miRNA based on prediction algorithms have a relatively high potential to be true direct targets of the treated candidate miRNA.

Hence, the downregulated genes can be tested for direct interaction with the miRNA using a luciferase assay. Identifying direct targets of the candidate miRNAs can be used to screen for small molecules to induce HSC quiescence and treat hepatic fibrogenesis. The candidate miRNAs that revert activated HSCs to quiescence can be tested in vivo to treat a mouse model(s) of NAFLD. It is also contemplated that chemically modified forms of candidate miRNAs, such as those sold commercially from Exiqon and Invitrogen, can be used in testing and/or treatment of liver disease as described herein.

Example 2: Cell Therapy for Non-Alcoholic Fatty Liver Disease Using Quiescently Reprogrammed Hepatic Stellate Cells Like most fatal liver diseases, NAFLD promotes chronic inflammation and fibrosis that ultimately lead to cirrhotic end-stage organ failure. During this pathologic progression, hepatic stellate cells (HSCs) are considered to play a central role in fibrogenesis (6-8). HSCs exist in two forms. In healthy individuals, they are quiescent and are morphologically characterized by multiple retinoid-rich lipid droplets. However, once activated, HSCs lose their lipid droplets and become pro-fibrotic by secreting collagen and factors that promote inflammation and fibrosis (9, 10).

miRNAs are short, non-coding RNAs that regulate expression of coding genes by base pairing imperfectly with their mRNA targets. Remarkably, because miRNAs can promiscuously target multiple different genes simultaneously, they can influence an entire biological program such as organ development, carcinogenesis, or cellular reprogramming (11, 12). Furthermore, certain miRNAs or their inhibitors have already been proposed to be used as therapeutic agents for diseases, including miR-29 (13) and anti-miR-21 (14) for cardiac and renal fibrosis and Miravirsen (miR-122 antagonist) for hepatitis C (15). Finally, miRNAs have been used by several labs to reprogram or to transdifferentiate one cell type to another (16-18).

Although it is accepted that activated hepatic stellate cells (HSCs) play an essential role in fibrotic progression of the liver, little is known about the function of microRNAs in the activation status of this cell type. The data presented herein demonstrate that miR-15a or miR-412 independently reverts activated HSCs back toward quiescence, and these quiescent-like cells improve hepatocyte steatosis and fibrosis in both in vitro and in vivo settings. This study aims to test the hypothesis that miR-15a and miR-412 promote quiescence in HSCs, which can subsequently suppress fibrotic progression in NAFLD. Further, the inventors proposed that promoting quiescence of HSCs can be a way to control fibrotic progression in the liver. Thus, a mouse model of NAFLD was treated with either mouse or human HSCs "quiescently reprogrammed" into a perpetual quiescent-like state using candidate microRNAs and to assess the efficacy in attenuating liver pathology.

This study provides novel methods and compositions related to purposefully engineered HSCs and their use to prevent, decrease, or reverse hepatic fibrosis.

Results miRNAs that can revert activated HSCs toward quiescence were sought. To test this, a whole genome microRNA (miRNA) library was screened to identify those that reverse HSC activation and induce quiescence. This survey screened for re-formation of retinoid-positive lipid droplets, a sign of quiescence, in HSCs when they are introduced to different miRNAs. The survey produced several hits, which were narrowed to two, miR-15a and miR-412, based on independent validation in both mouse and human HSCs and the existence of human homologue.

Figure 6A:
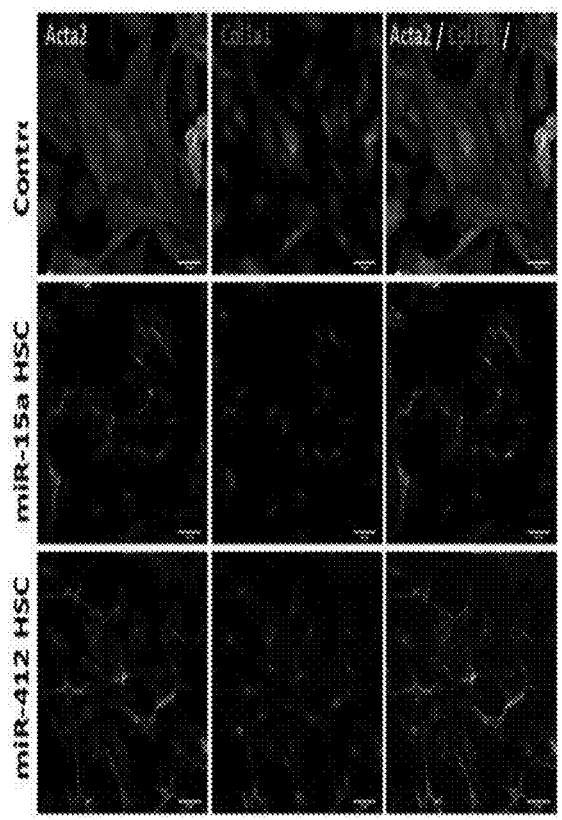
FIGS. 6A-6B show data relating to the delivery of miR-15a or miR-412 to activated HSCs, which causes changes in morphology toward that of quiescence. The size of the HSCs decreased by 10-100 folds supported by same scale bar for all panels (FIG. 6A). Forced expression of miR-15a or miR-412 downregulated alpha smooth muscle actin (Acta2) and alpha-1 type I collagen (Colla1) measured with PCR (FIG. 6B). Data are presented as mean +/−SD.
Figure 6B:
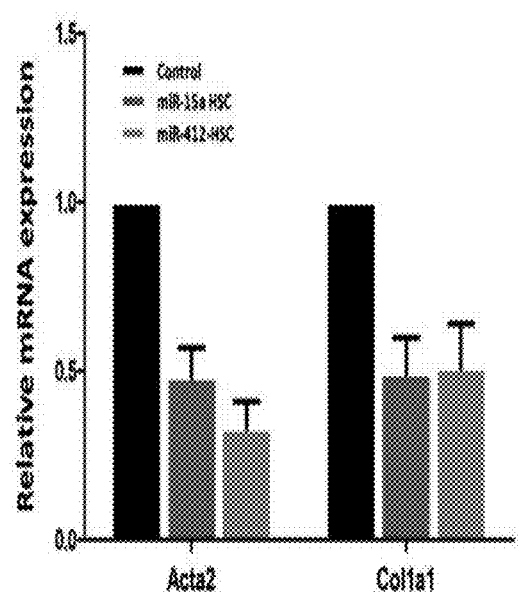

The two miRNA candidates, miR-15a and miR-412 force reversion of HSCs from the activated to the quiescent state even in a culture condition that promotes activation. Delivering miR-15a or miR-412 to activated HSCs caused dramatic changes in morphology toward that of quiescence. The overall size of the HSCs decreased by 10-100 folds, becoming more quiescent-like (FIG. 6A). Furthermore, forced expression of miR-15a or miR-412 downregulated two of the most important gene markers of activation, alpha smooth muscle actin (Acta2) and alpha-1 type I collagen (Col1a1) (FIG. 6B). For more comprehensive expression analysis, deep-RNA sequencing demonstrated that the quiescent-like HSCs that received miR-15a or miR-412 had a global transcriptional profile 40-50% closer to the quiescent HSCs than the activated cells (data not shown). Most importantly, these HSCs that became quiescent-like by miR-15a or miR-412 had a functional phenotype similar to truly quiescent HSCs.

Figure 7A:
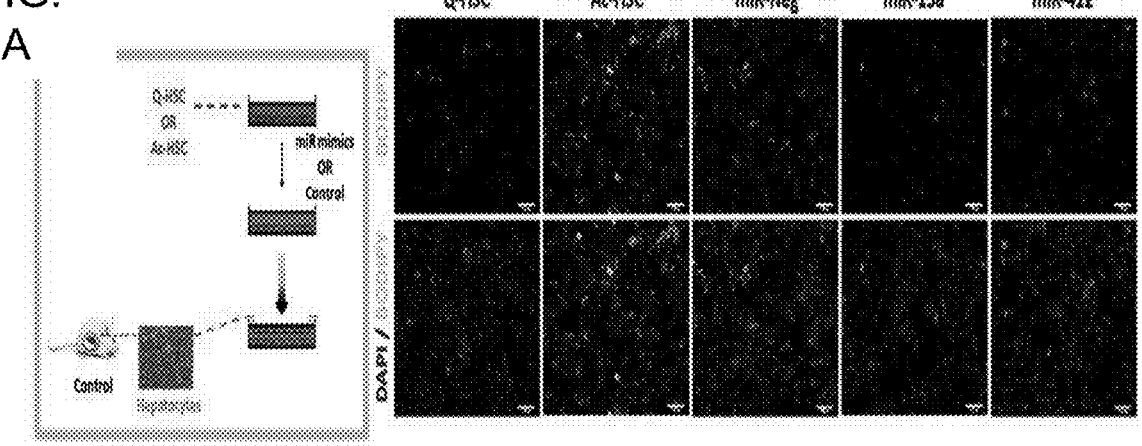
FIGS. 7A-7B shows miR-15a or miR-412-transfected HSCs that have reverted to quiescent-like state have a functional phenotype in that they do not cause steatosis in hepatocytes when the two cell types are co-cultured (FIG. 7A). Activated HSCs untreated with candidate miRNAs induce hepatocyte steatosis when they are co-cultured. Hepatocyte steatosis stained green with BODIPY. Q-HSC, quiescent hepatic stellate cell; Ac-HSC, activated hepatic stellate cell; miR-Neg, microRNA negative control (FIG. 7A). Control HSCs harvested from a mouse model of NAFLD induce steatosis in adjacent hepatocytes during co-culture. These same HSCs infected with lentivirus carrying miR-15a or miR-412 lose their ability to induce steatosis in adjacent hepatocytes, reverting to phenotype seen in quiescent HSCs (FIG. 7B).
Figure 7B:
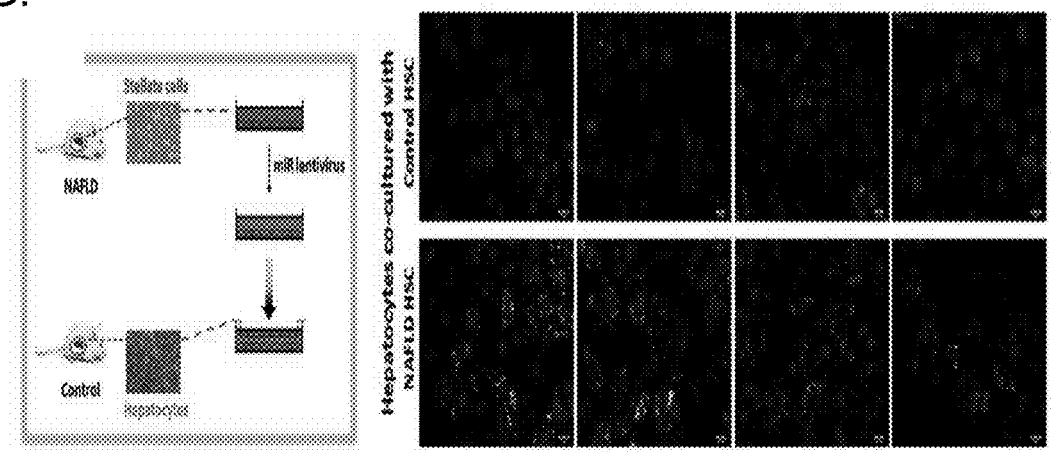

In vitro experiments indicated that the quiescent-like HSCs did not induce steatosis in healthy hepatocytes when the two cell types were co-cultured. In contrast, activated HSCs untreated with candidate miRNAs induced hepatocyte steatosis when they were co-cultured (FIG. 7A). Similarly, the steatosis-inducing effect of HSCs harvested from a mouse model of NAFLD (choline-deficient, L-amino acid defined, high fat diet or CDA-HFD) became abrogated when miR-15a or miR-412 was delivered, adopting the phenotype of healthy, quiescent HSCs (FIG. 7B).

Figure 8A:
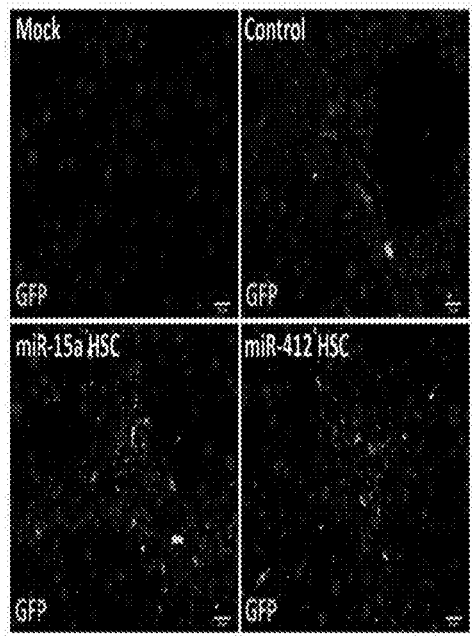
FIGS. 8A-8C Quiescence reprogrammed HSCs injected into the spleen grafted on to the liver, as evidenced by the liver producing the GFP signal built into the vector driving the miRNA expression (FIG. 8A). Mock, olive oil gavage and injecting no HSC; Control, CCl4 gavage and injecting HSCs with empty GFP-vector; miR-15a HSC, CCl4 gavage and injecting HSCs with miR-15a-GFP-vector; miR-412 HSC, CCl4 gavage and injecting HSCs with miR-412-GFP-vector. Alpha-1 type I collagen (Colla1) immunofluorescence shows decreased expression in the liver when injected with HSCs quiescently reprogrammed with miRNA compared to control (FIG. 8B). Decreased expression of Acta2 and Colla1 in the whole liver when treated with quiescently reprogrammed HSCs, measured with PCR (FIG. 8C). Data are presented as mean +/−SD.
Figure 8B:
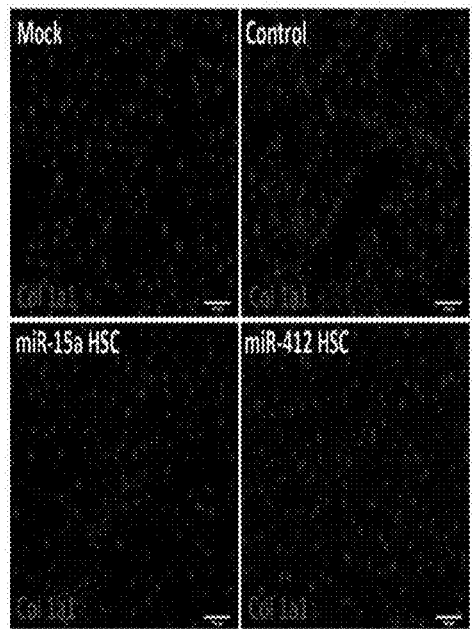
Figure 8C:
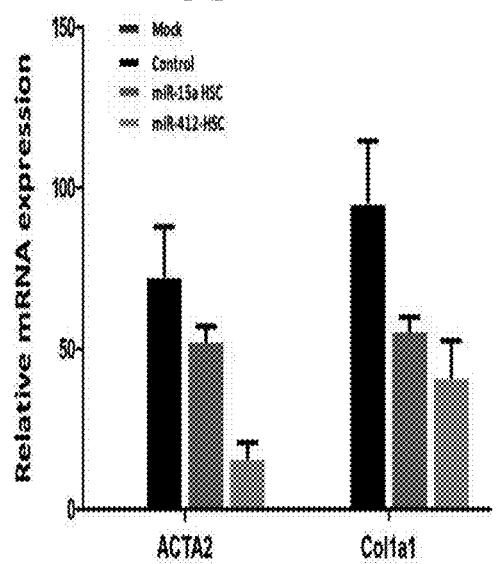

Lastly, it was tested whether activated HSCs that have been permanently quiescently reprogrammed by constitutive expression of either miR-15a or miR-412 using a piggyBac transposon vector (FIG. 6A) that can be injected into a mouse model of liver fibrosis to improve the degree of liver pathology. Remarkably, the quiescently reprogrammed HSCs injected into the spleen grafted on to the liver, evidenced by the liver producing the GFP signal built into the vector driving the miRNA expression (FIG. 8A). Mice challenged with CCl4 for four weeks that received a single injection of cell therapy on the third week showed attenuated hepatic steatosis (data not shown) and decreased expression of Acta2 and Col1a1 by 50% or greater in the whole liver by the fourth week (FIGS. 8B and 8C). It is also contemplated herein that the miRNAs described herein will also have a beneficial effect on animal models of NAFLD.

Further, a CDA-HFD mouse model of NAFLD can be utilized to test and/or confirm efficacy of administration of miR-15a and/or miR-412. By the end of week 6, the mice in this model develop enlarged fatty liver with at least stage 1 fibrosis (on a 0-4 scale) (20). Mice can be treated with either a single injection of cell therapy on week 3 or three injections on weeks 1, 3, and 5. Efficacy can be assessed by performing PCR of profibrotic genes, Masson's trichrome stain, and hydroxyproline assay in the liver, and measuring plasma ALT.

A similar experiment using this model, the CDA-HFD treatment is sustained for 12 weeks when fibrosis reaches stage 3. One can base the total number and/or interval of cell therapy on the results of the CDA-HFD treatment at 6 weeks, however treatment in this experiment will be initiated at 6 weeks. It is specifically contemplated herein that fibrosis and cirrhosis are reversible using a composition comprising miR-15a and/or miR-412 or a cell expressing miR-15a and/or miR-412.

In addition, these NAFLD mouse models can be executed using human HSCs. The inventors have shown that human HSCs can revert to a quiescent-like state using the human homologue of miRNA-15a or miR-412 and this effect can be tested in in vivo mouse models of NAFLD. It may be desirable to use severe combined immunodeficiency (SCID) mice to avoid immune rejection of human cells by the animal model.

Transient transfection of miR-15a or miR-412 on human HSCs can be used to achieve a quiescent-like state. However, it is also contemplated herein that a human HSC can be permanently quiescently reprogrammed using miR-15a and miR-412, One of skill in the art will recognize that acquiring human HSCs for the purpose of quiescence reprogramming and putting them back into patients can encounter technical obstacles, such as triggering of an immune response. However, such obstacles can be avoided by obtaining an autologous liver biopsy to isolate HSCs, followed by ex vivo expansion and quiescence reprogramming. Since NAFLD and other progressive liver diseases take years if not decades to reach cirrhosis, this option may be adequate. Alternatively, readily available somatic cells, such as skin or blood cells, can be quiescently reprogrammed to become HSC-like cells. It is also possible to render human HSCs non-immunogenic through bioengineering.

REFERENCES FOR EXAMPLE 2

1. Clark J M, Brancati F L, Diehl A M. The prevalence and etiology of elevated aminotransferase levels in the United States. Am J Gastroenterol 2003; 98:960-967.
2. Charlton M R, Burns J M, Pedersen R A, Watt K D, Heimbach J K, Dierkhising R A. Frequency and outcomes of liver transplantation for nonalcoholic steatohepatitis in the United States. Gastroenterology 2011; 141:1249-1253.
3. Starley B Q, Calcagno C J, Harrison S A. Nonalcoholic fatty liver disease and hepatocellular carcinoma: a weighty connection. Hepatology 2010; 51:1820-1832.
4. Browning J D, Szczepaniak L S, Dobbins R, Nuremberg P, Horton J D, Cohen J C, Grundy S M, et al. Prevalence of hepatic steatosis in an urban population in the United States: impact of ethnicity. Hepatology 2004; 40:1387-1395.
5. Corey K E, Rinella M E. Medical and Surgical Treatment Options for Nonalcoholic Steatohepatitis. Dig Dis Sci 2016.
6. Friedman S L. Mechanisms of hepatic fibrogenesis. Gastroenterology 2008; 134:1655-1669.
7. Friedman S L. Hepatic stellate cells: protean, multifunctional, and enigmatic cells of the liver. Physiol Rev 2008; 88:125-172.
8. Puche J E, Lee Y A, Jiao J, Aloman C, Fiel M I, Munoz U, Kraus T, et al. A novel murine model to deplete hepatic stellate cells uncovers their role in amplifying liver damage in mice. Hepatology 2013; 57:339-350.
9. Kisseleva T, Cong M, Paik Y, Scholten D, Jiang C, Benner C, Iwaisako K, et al. Myofibroblasts revert to an inactive phenotype during regression of liver fibrosis. Proc Natl Acad Sci USA 2012; 109:9448-9453.
10. Mederacke I, Hsu C C, Troeger J S, Huebener P, Mu X, Dapito D H, Pradere J P, et al. Fate tracing reveals hepatic stellate cells as dominant contributors to liver fibrosis independent of its aetiology. Nat Commun 2013; 4:2823.
11. Ivey K N, Srivastava D. MicroRNAs as regulators of differentiation and cell fate decisions. Cell Stem Cell 2010; 7:36-41.
12. Kim B M, Thier M C, Oh S, Sherwood R, Kanellopoulou C, Edenhofer F, Choi M Y. MicroRNAs are indispensable for reprogramming mouse embryonic fibroblasts into induced stem cell-like cells. PLoS One 2012; 7:e39239.
13. Zhang Y, Huang X R, Wei L H, Chung A C, Yu C M, Lan H Y. miR-29b as a therapeutic agent for angiotensin I I-induced cardiac fibrosis by targeting TGF-beta/Smad3 signaling. Mol Ther 2014; 22:974-985.
14. He Y, Huang C, Li J. miR-21 is a critical therapeutic target for renal fibrosis. Cell Biochem Biophys 2014; 68:635-636.
15. Janssen H L, Reesink H W, Lawitz E J, Zeuzem S, Rodriguez-Torres M, Patel K, van der Meer A J, et al. Treatment of HCV infection by targeting microRNA. N Engl J Med 2013; 368:1685-1694.
16. Anokye-Danso F, Trivedi C M, Juhr D, Gupta M, Cui Z, Tian Y, Zhang Y, et al. Highly Efficient miRNA-Mediated Reprogramming of Mouse and Human Somatic Cells to Pluripotency. Cell Stem Cell 2011; 8:376-388.
17. Miyoshi N, Ishii H, Nagano H, Haraguchi N, Dewi D L, Kano Y, Nishikawa S, et al. Reprogramming of mouse and human cells to pluripotency using mature microRNAs. Cell Stem Cell 2011; 8:633-638.
18. Yoo A S, Sun A X, Li L, Shcheglovitov A, Portmann T, Li Y, Lee-Messer C, et al. MicroRNA-mediated conversion of human fibroblasts to neurons. Nature 2011; 476: 228-231.
19. Terai S, Tsuchiya A. Status of and candidates for cell therapy in liver cirrhosis: overcoming the "point of no return" in advanced liver cirrhosis. J Gastroenterol 2017; 52:129-140.
20. Matsumoto M, Hada N, Sakamaki Y, Uno A, Shiga T, Tanaka C, Ito T, et al. An improved mouse model that rapidly develops fibrosis in non-alcoholic steatohepatitis. Int J Exp Pathol 2013; 94:93-103.
21. Rockey D C. Translating an understanding of the pathogenesis of hepatic fibrosis to novel therapies. Clin Gastroenterol Hepatol 2013; 11:224-231 e221-225.
22. Ellis E L, Mann D A. Clinical evidence for the regression of liver fibrosis. J Hepatol 2012; 56:1171-1180.
23. Mallet V, Gilgenkrantz H, Serpaggi J, Verkarre V, Vallet-Pichard A, Fontaine H, Pol S. Brief communication: the relationship of regression of cirrhosis to outcome in chronic hepatitis C. Ann Intern Med 2008; 149:399-403.
24. Czaja A J, Carpenter H A. Decreased fibrosis during corticosteroid therapy of autoimmune hepatitis. J Hepatol 2004; 40:646-652.
25. Hammel P, Couvelard A, O'Toole D, Ratouis A, Sauvanet A, Flejou J F, Degott C, et al. Regression of liver fibrosis after biliary drainage in patients with chronic pancreatitis and stenosis of the common bile duct. N Engl J Med 2001; 344:418-423.
26. Dufour J F, DeLellis R, Kaplan M M. Reversibility of hepatic fibrosis in autoimmune hepatitis. Ann Intern Med 1997; 127:981-985.
27. Ieda M, Fu J D, Delgado-Olguin P, Vedantham V, Hayashi Y, Bruneau B G, Srivastava D. Direct reprogramming of fibroblasts into functional cardiomyocytes by defined factors. Cell 2010; 142:375-386.

28. Sekiya S, Suzuki A. Direct conversion of mouse fibroblasts to hepatocyte-like cells by defined factors. Nature 2011; 475:390-393.
29. Huang P, He Z, Ji S, Sun H, Xiang D, Liu C, Hu Y, et al. Induction of functional hepatocyte-like cells from mouse fibroblasts by defined factors. Nature 2011; 475: 386-389.
30. Vierbuchen T, Ostermeier A, Pang Z P, Kokubu Y, Sudhof T C, Wernig M. Direct conversion of fibroblasts to functional neurons by defined factors. Nature 2010; 463: 1035-1041.
31. Zhou Q, Brown J, Kanarek A, Rajagopal J, Melton D A. In vivo reprogramming of adult pancreatic exocrine cells to beta-cells. Nature 2008; 455:627-632.

Example 3: Determining the Mechanism/Function of microRNAs in Hepatic Stellate Cell Activation and Non-Alcoholic Fatty Liver Disease With the advent of highly effective antiviral therapies against hepatitis B and C, non-alcoholic fatty liver disease (NAFLD) has become the most serious hepatic disorder. NAFLD is now considered the most common liver disease in the developed world [1], and is projected to become the leading cause of end-stage liver disease, hepatic transplant, and hepatocellular carcinoma by 2025 [2, 3]. The disease is particularly common in rich nations such as the United States where 64 to 80 million people are estimated to be affected due to the high prevalence of risk factors including obesity, diabetes, and hyperlipidemia [4, 5]. Moreover, the economic burden of NAFLD is staggering, with annual direct medical costs projected to be about $103 billion [5]. The disease starts as hepatic steatosis but can progress to non-alcoholic steatohepatitis (NASH), fibrosis, and ultimately cirrhotic liver failure or hepatocellular carcinoma. NAFLD is currently managed mainly by decreasing risk factors. However, these measures are often difficult to achieve, and even eliminating them does not guarantee improvement [6]. Given that NAFLD is becoming the most common cause of liver related morbidity and that there are no drugs to manage it currently, better treatment options are urgently needed.

NAFLD progresses in a stepwise fashion through steatosis, inflammation, and fibrosis. During this pathologic cascade, hepatic stellate cells (HSCs) are considered to play a central role in hepatic fibrogenesis [7-9]. HSCs exist in two forms. In healthy individuals, they are quiescent, characterized by multiple retinoid-rich lipid droplets. However, once activated, they lose their lipid droplets and become pro-fibrotic myofibroblasts, secreting collagen and mediators that promote scar formation [10, 11]. Although the importance of HSCs in hepatic fibrosis is well established, there is still much that is not known about this cell type. For example, it is not known if. (i) there are genes that can reverse activated HSCs back toward quiescence, (ii) HSCs are also involved in early NAFLD, promoting steatosis and inflammation (i.e., not just fibrosis), and (iii) there are important mediators involved in the processes of HSCs that contribute to steatohepatitis or fibrosis.

Among many gaps in the knowledge, understanding the role of microRNAs (miRNAs) in determining HSC activation status is particularly poor. Although many groups have profiled expression of miRNAs in HSCs the functional significance of their expression status is largely unclear [12-14]. In response, the instant research has focused on quickly discovering key miRNAs that influence HSC's activation status. Instead of relying on large scale expression profiling, the inventors developed a functional screen and assays to systematically identify miRNAs that force activated HSCs back toward quiescence, and through this effort, identified miR-15a and miR-412. Surprisingly, transiently delivering just one of these miRNAs can shift global gene expression about halfway back toward quiescence from the activated state along the transcriptional axis connecting them. Promoting HSC quiescence through these miRNAs or their downstream targets can prevent fibrotic progression in NAFLD.

One of the major problems many anti-NAFLD/NASH agents currently being developed is that they tend to have non-specific biological actions that lead to significant side effects. Hence, they may have untoward outcome when used in certain populations. For example, vitamin E is one of the best studied drugs for NAFLD and has shown promise, but two meta-analyses have suggested that its use may increase all-cause mortality at higher doses, likely from other effects besides their role in the liver [15-17]. For these reasons, frustrating HSC's activation in the liver may be a more specific approach to treat NAFLD.

Finally, activated HSCs causing fibrosis is not unique to NAFLD. Most chronic liver diseases involve HSCs promoting fibrosis for many years before arriving at cirrhosis. Thus, if a therapeutic agent can decrease the rate of fibrotic progression by targeting HSCs, it is contemplated herein that this approach can be used in the treatment of other liver diseases besides NAFLD. Even for diseases such as primary biliary cirrhosis or autoimmune hepatitis that have established drug therapies, an additional agent that inhibits fibrotic progression can significantly improve the ability to manage these chronic illnesses.

Although several compounds are in human trials for treating NAFLD, none of them rely on preventing or reversing HSC activation as the primary goal [6, 18, 19]. In response, the first major innovation of this study started with the attempt to control the activation status of HSCs as a way to prevent progressive liver disease. The in vitro screen capitalized on the natural tendency of HSCs to become activated when they are grown on plastic surface. As HSCs become activated, they lose lipid droplets present abundantly in quiescent HSCs. Utilizing this useful phenotypic dichotomy, miRNAs were identified that force activated HSCs to become more quiescent-like by tracking the level of lipid droplets that re-form in the cytoplasm. Since miRNAs are known to simultaneously target multiple coding genes to influence an entire cellular program, it was reasoned that even one miRNA can induce this transdifferentiation. Thus, through an unbiased survey, several miRNA candidates were identified that revert HSCs back toward quiescence from the activated state, as demonstrated by the reappearance of intracellular lipid droplets. It is contemplated herein that this innovation in utilizing miRNAs to control HSC activation status can serve as the foundation for developing a novel category of therapy that prevents hepatic fibrosis.

The next major innovation of the instant study comes in the form of a novel cell therapy using quiescent-like HSCs. Although the initial screen and follow-up in vitro assays were initially performed using transient transfection with miRNA mimics of miR-15a or miR-412, it is also contemplated herein that nucleic acids encoding the miRNA mimics can be integrated into the genome for constitutive expression (e.g., using a piggyBac transposon vector that can integrate into the genome to constitutively express either miRNA). HSCs having constitutive expression of the miRNA(s) [20] seem to transdifferentiate permanently toward a quiescent-like state with dramatic changes in expression, morphology, and function. Remarkably, these quiescently reprogrammed HSCs engrafted on to CCl4 challenged mouse liver and caused improvement in steatosis and fibrosis. Thus, purposefully engineered HSCs are contemplated for use as therapy for NASH or hepatic fibrosis.

Another major innovation of the instant study is technical in nature. To confirm that HSCs are the main driver of hepatic fibrosis in NASH, the disruption of HSC activation should prevent hepatic fibrosis. One of the biggest obstacles that hinders the study of HSC function and mechanism of action is the paucity of good in vitro models for HSC's interaction with other cell types, allowing simple assays to assess functional phenotype and mechanism of action. To meet this need, a co-culture system was developed using primary mouse HSCs and hepatocytes to recreate the microenvironment of these two cell types in close proximity. Moreover, by combining this technology with mouse models of NASH, NASH-HSC's effect on nearby hepatocytes can be reliably measured. Interestingly, NASH-HSCs from choline-deficient, L-amino acid defined, high fat diet (CDAHFD) model induced steatosis stimulated expression of inflammatory cytokines in co-cultured hepatocytes harvested from healthy mice [22]. This signaling does not require cell-cell contact because the two cell types in co-culture can be separated, for example, by a TRAN-SWELL™, implying secretion of soluble factor(s) by HSCs. Furthermore, induction of fatty accumulation in hepatocytes can be reproduced even when the conditioned media from cultured NASH-HSCs is applied to normal hepatocytes, without the co-culture. This system permits identification of HSC-secreted mediators that induce steatosis and proinflammatory cytokines in hepatocytes.

By modeling the interaction between HSCs and hepatocytes during NAFLD using a simple, yet robust, ex vivo system, the inventors have created a technology that is amenable to mechanistic and drug discovery experiments. In particular, by utilizing primary cells instead of cell lines our co-culture system more faithfully simulates the pathophysiologic microenvironment of these two cell types in vivo [23]. This co-culture system was made feasible by improving existing protocols for harvesting and culturing these cells so that the quality is maximized while the effort is minimized [24]. These technical enhancements were critical for delivering consistent and reproducible results using primary cells.

The potential impact of this co-culture system that models NAFLD in the pursuit of developing new therapies is significant. First, the co-culture system can be leveraged to study the molecular interaction between these two cell types. For instance, by analyzing the conditioned media of HSCs or hepatocytes from NAFLD, one can easily investigate secreted factors that can function in paracrine or autocrine fashion. This system permits these fundamental questions that facilitate the discovery of potential therapeutics to be answered. In addition, this culturing system enables one to perform in vitro functional screens to identify agents that can prevent or reverse hepatic steatosis and inflammation since the system is amenable to various experimental manipulations. For instance, potential drugs can be tested on either hepatocytes or HSCs exclusively, or together. Besides small molecules, non-traditional agents, such as siRNAs, miRNAs, and antibodies, can be tested. Finally, this co-culture system can be used to study other liver diseases as long as there is a representative mouse model. For example, the interaction of hepatocytes and HSCs in alcoholic liver disease can be modeled by isolating these cell types in alcohol-fed mice [25].

Elucidating the Function of miR-15a and miR-412 in Influencing HSC Activation Status Activated HSCs that received miR-15a or miR-412 changed their morphology, expression profile and functional phenotype closer to that of quiescent HSCs. The mechanistic underpinning behind this initial observation can be determined by identifying direct targets of miR-15a and miR-412 by comparing the available global gene expression profiles of HSCs that are 1) quiescent, 2) activated, and 3) quiescent-like after receiving miR-15a or miR-412, and using a prediction algorithm and a luciferase assay to identify their direct targets.

The following studies are contemplated herein to elucidate the mechanism of miR-15a and/or miR-412 in the treatment of NAFLD:
  (i) CRISPR technology can be used to knockout miR-15a and miR-412 in HSCs to characterize miRNA-deleted HSCs using morphology, gene expression, proliferation, and interaction with hepatocytes,
  (ii) miR-15a and miR-412 can be administered simultaneously to HSCs to assess whether they work in concert to revert activated HSCs even closer to true quiescence.

Testing Whether Delivery of miR-15a or miR-412 to Mouse Models of Hepatic Fibrosis or NASH Decreases their Disease Severity $CCl_4$ challenged mice that received injection of HSCs locked into a quiescent-like state by constitutive expression of miR-15a or miR-412 showed improvement of hepatic steatosis, inflammation and collagen expression, thus it is hypothesized that delivering miR-15a and/or miR-412 are a potential therapy for NAFLD.

Given the in vitro and in vivo data that support the beneficial effect of HSCs expressing miR-15a or miR-412 in decreasing steatosis and fibrosis, the in vivo treatment studies can be expanded using a mouse model of diet-induced NAFLD and $CCl_4$ induced hepatic fibrosis. Furthermore, three different miRNA delivery systems can be tested: (i) cell therapy using quiescently reprogrammed mouse HSCs constitutively expressing miR-15a or miR-412; using quiescent-like human HSCs constitutively expressing miR-15a or miR-412 and (ii) injecting lentivirus overexpressing miR-15a or miR-412 into a subject, such as a mouse (e.g., tail vein injection, (iii) injecting chemically modified mimics of miR-15a or miR-412 packaged in a lipid based carrier into the subject, for example in the tail vein or peritoneal space of a research animal (e.g., mouse). After 8-12 weeks of therapy, both control and test mice are sacrificed and tested for the extent of liver steatosis, inflammation, and fibrosis.

Results

Hepatic stellate cells (HSCs) make up only 5% to 15% of all cells in the liver, but their great influence in promoting fibrosis in progressive liver diseases by transdifferentiating into myofibroblasts is well recognized [7, 8, 27, 28], however the role of miRNAs during the reversion of activated HSCs back toward quiescence, one possible fate of HSCs during the resolution of hepatic inflammation and fibrosis [10, 29].

To identify those miRNAs that promote reversion of activated HSCs toward quiescence, an unbiased functional screen was designed to look for reappearance of intracellular lipid droplets with retinoids, a marker of quiescence, after activated HSCs received individual miRNA mimics from a full genome miRNA library (data not shown). This survey was performed in 96 well plates, each well culturing activated HSCs with almost no lipid droplets. Once individual miRNAs were transfected into each well, HSCs in some of the wells showed Bodipy stain positive lipid droplets reformed within three days. This initial screen produced 15 primary hits. miRNAs miR-15a and miR-412 were selected for further investigation based on the existence of human orthologs and their robust ability to re-form lipid droplets and to dramatically change cell morphology toward quiescence in both mouse and human HSCs. The newly formed lipid droplets were retinoid positive evidenced by fluorescence under ultraviolet light, consistent with those in quiescent HSCs. The overall size of the transfected HSCs decreased by 10-100 fold, becoming more quiescent-like. Furthermore, forced expression of miR-15a or miR-412 downregulated two gene markers of HSC activation: alpha smooth muscle actin (Acta2) and alpha-1 type I collagen (Colla1). For more comprehensive expression analysis, deep-RNA sequencing demonstrated that the quiescent-like HSCs that received miR-15a or miR-412 had a global transcriptional profile 40-50% closer to quiescent HSCs than activated cells. Most importantly, HSCs that became quiescent-like by miR-15a or miR-412 had a functional phenotype similar to truly quiescent HSCs. In vitro experiments demonstrated that the quiescent-like HSCs did not induce steatosis in healthy hepatocytes when the two cell types were co-cultured. In contrast, activated HSCs untreated with candidate miRNAs induced hepatocyte steatosis when they were co-cultured.

miR-15a and miR-412 have not been studied in the context of hepatic stellate cell. miRNAs are small non-coding genes that are usually 22 nucleotides in length and are involved in all biologic and pathologic processes. They downregulate target coding genes by imperfectly base-pairing with complementary sequences within their mRNA targets to induce degradation or translational inhibition. Each miRNA can regulate many different coding genes while each target gene can be regulated by many different miRNAs, constituting a complex layer of gene regulatory network. miRNAs directly target about 50% of all mammalian coding genes, demonstrating their wide reach in gene regulation [33]. This study and others have shown that miRNAs are essential for cellular proliferation and reprogramming [34-36]. Nonetheless, miRNAs' role in HSC activation or reversion to quiescence has not been explored.

In addition, HSCs expressing both miRa-15a and miR-412 can be tested for cell therapy in the setting of CCl4 induced hepatic fibrosis and diet induced NASH. It is specifically contemplated herein that one or more of the HSC line(s) described herein may prevent of decrease liver damage and fibrosis at a greater degree than that observed with HSC lines expressing either miR-15a or miR-412 alone.

Testing Whether Delivery or miR-15a or miR-412 to Mouse Models of Hepatic Fibrosis or NASH Decreases their Disease Severity HSCs obtained from a diet model of NASH that were treated with miR-15a or miR-412 to revert them back toward quiescence abrogated their ability to induce both steatosis and expression of pro-inflammatory cytokines in co-cultured hepatocytes ex vivo. Furthermore, miR-15a and miR-412 force reversion of activated HSCs toward quiescence even in culture conditions that promote activation. miRNAs were tested to determine if, when delivered in vivo, they attenuate the level of hepatic pathology in a CCl4 mouse model, especially since HSCs expressing either miR-15a or miR-412 will likely maintain a quiescent-like state even in the diseased liver with activation promoting signals. Through cell contact and soluble mediators, quiescent-like HSCs can also induce other cell types within the liver to dampen their signals that promote steatosis, inflammation, or fibrosis.

Although there are a variety of methods to deliver miRNAs to live mice, the inventors initially selected injection of HSCs that have become quiescent-like by constitutively expressing miR-15a or miR-412. Hence, the viability of a new cell therapy for liver disease was assessed using HSCs that have been engineered to a quiescent-like state. This experiment was performed in mice challenged with four-weeks of CCl4. Remarkably, injected HSCs grafted onto the liver, as confirmed by visualizing within the liver cells emitting the GFP signal inserted into the piggyBac vector expressing miRNA [20]. More importantly, mice treated with a single intrasplenic injection of quiescent-like HSCs had lower hepatic collagen expression and histology showing decreased ballooning, apoptosis, inflammation, and fibrosis in the liver. Additional in vivo experiments can be performed to further assess the potential of miR-15a and miR-412 in treating hepatic steatosis, inflammation, and fibrosis using mouse models of NASH and hepatic fibrosis.

Treating mouse models of hepatic fibrosis and NASH with cell therapy using quiescence reprogrammed mouse HSCs with miR-15a or miR-412: The experiments provided in the Figures and Examples of the instant specification provide novel, purposefully engineered HSCs used to prevent or reverse hepatic fibrosis. The miRNAs were delivered ex vivo to revert activated to HSCs toward quiescence, which were then injected into CCl4 challenged mice. The HSCs originated from separate, congenic mice, and 500,000 cells were injected once on the third week of four week course of CCl4. Further tests to determine the therapeutic potential of cell therapy using miRNA-quiescence reprogrammed HSCs are specifically contemplated herein. For example, the beneficial effect of the cell therapy can be tested to determine if it increases with an increasing number of cells and/or injections/doses. For all cell therapy experiments, the injection of 500,000 quiescent reprogrammed HSCs with miR15a or miR-412 into the spleen is specifically contemplated and the efficacy can be assessed by performing PCR of pro-fibrotic genes in the liver, histology including H&E and Masson's trichrome stain, hepatic hydroxyproline assay, and measuring plasma ALT. All appropriate controls including mouse models with no treatment and treatment with HSCs that have not been quiescently reprogrammed can be included in the experimental design.

CCl4 model of hepatic fibrosis: To test whether quiescent-like HSCs can prevent or reverse hepatic fibrosis, two separate experiments with different cell injection schedules can be performed. All CCl4 administration can be performed by oral gavage twice a week.

Fibrosis prevention study: Mice challenged with CCl4 for 8 weeks normally develop cirrhosis. Quiescence reprogrammed HSCs can be injected on the second, fourth, and sixth week during the 8 week course of CCl4 challenge. All mice can be sacrificed at the end of week 8.

Fibrosis reversion study: To test whether the cell therapy can reverse pre-existing hepatic fibrosis compared to control, quiescence reprogrammed HSCs can be injected on the ninth, eleventh, and thirteenth week after 8 week course of CCl4 challenge has been completed. All mice will be sacrificed at the end of week 14.

Diet model of NASH: The choline-deficient, L-amino acid defined, high fat diet (CDAHFD) model develops significant NASH by week 3 and stage 1 fibrosis (on a 0-4 scale) by week 6 [22]. Mice can be treated with either a single injection of cell therapy on week 3 or three injections on weeks 1, 3, and 5 during 6 weeks of CDAHFD. All mice can be sacrificed at the end of week 6.

Treating mouse models of hepatic fibrosis and NASH with cell therapy using human HSCs quiescence reprogrammed with miR-15a or miR-412: It has already been shown that activated human HSCs can revert to a quiescent-like state after receiving human ortholog of miR-15a or miR-412. These reverted cells re-formed retinoid positive lipid droplets and were able to decrease pro-inflammatory cytokine expression from co-cultured hepatocellular carcinoma cell line HepG2. It is specifically contemplated herein to test primary human HSCs for treating a mouse model of hepatic fibrosis in determining the therapeutic potential of miR-15a and miR-412. CCl4 induced hepatic fibrosis can be generated in severe combined immune deficient (SCID) mice to prevent immune rejection of human cells. CCl4-based hepatic fibrosis models have been generated successfully by other groups [39].

Fibrosis prevention study: Quiescently reprogrammed human HSCs can be injected on the second, fourth, and sixth week during an 8 week course of CCl4 challenge in SCID mice. All mice can be sacrificed at the end of week 8.

Fibrosis reversion study: To test whether quiescently reprogrammed human HSCs can reverse pre-existing hepatic fibrosis compared to control, such HSCs can be injected on the ninth, eleventh, and thirteenth week after 8 week course of CCl4 challenge has been completed. All mice will be sacrificed at the end of week 14.

Treating mouse models of hepatic fibrosis and NASH by injecting lentivirus overexpressing miR15a or miR-412: These initial experiments demonstrated that injecting quiescently reprogrammed HSCs with miR-15a and miR-412 can decrease collagen expression and the overall level of liver damage in progressive hepatic fibrosis. Injection of lentivirus expressing miRNA(s) is specifically contemplated herein. The use of a lentiviral vector is generally not preferred for human therapy, but modified lentiviral vectors or other retroviral vectors encoding the miRNA(s) as described herein are specifically contemplated for administration as a therapeutic agent to a human subject.

CCl4 Fibrosis study: Lentivirus expressing either miR-15a or miR-412 can be injected into tail vein on the second, fourth, and sixth week during the 8 week course of CCl4 challenge. All mice can be sacrificed at the end of week 8.

CDAHFD NASH study: Lentivirus expressing either miR-15a or miR-412 can be injected on weeks 1, 3, and 5 during 6 weeks of CDAHFD. All mice can be sacrificed at the end of week 6.

Treating mouse models of hepatic fibrosis and NASH by injecting mimics of miR-15a or miR-412 packaged in a carrier. As another delivery method, miRNA mimics packaged in a lipid based carrier (MaxSuppressor™ by BIOO Scientific) can be tested, for example, by injection into tail vein [40, 41]. By avoiding lentivirus, this method or its variation may be more desirable for the delivery of the miRNA(s) described herein to a human subject.

CCl4 Fibrosis study: Lipid carriers containing either miR-15a or miR-412 can be injected into tail vein on the second, fourth, and sixth week during the 8 week course of CCl4 challenge. All mice will be sacrificed at the end of week 8.

CDAHFD NASH study: Lipid carriers containing either miR-15a or miR-412 can be injected on weeks 1, 3, and 5 during 6 weeks of CDAHFD. All mice can be sacrificed at the end of week 6.

REFERENCES FOR EXAMPLE 3

1. Clark J M, Brancati F L, Diehl A M: The prevalence and etiology of elevated aminotransferase levels in the United States. Am J Gastroenterol 2003, 98(5):960-967.
2. Charlton M R, Burns J M, Pedersen R A, Watt K D, Heimbach J K, Dierkhising R A: Frequency and outcomes of liver transplantation for nonalcoholic steatohepatitis in the United States. Gastroenterology 2011, 141(4):1249-1253.
3. Starley B Q, Calcagno C J, Harrison S A: Nonalcoholic fatty liver disease and hepatocellular carcinoma: a weighty connection. Hepatology 2010, 51(5):1820-1832.
4. Browning J D, Szczepaniak L S, Dobbins R, Nuremberg P, Horton J D, Cohen J C, Grundy S M, Hobbs H H: Prevalence of hepatic steatosis in an urban population in the United States: impact of ethnicity. Hepatology 2004, 40(6):1387-1395.
5. Younossi Z M, Blissett D, Blissett R, Henry L, Stepanova M, Younossi Y, Racila A, Hunt S, Beckerman R: The economic and clinical burden of nonalcoholic fatty liver disease in the United States and Europe. Hepatology 2016, 64(5):1577-1586.
6. Lassailly G, Caiazzo R, Pattou F, Mathurin P: Perspectives on Treatment for Nonalcoholic Steatohepatitis. Gastroenterology 2016.
7. Friedman S L: Mechanisms of hepatic fibrogenesis. Gastroenterology 2008, 134(6):1655-1669.
8. Friedman S L: Hepatic stellate cells: protean, multifunctional, and enigmatic cells of the liver. Physiol Rev 2008, 88(1):125-172.
9. Puche J E, Lee Y A, Jiao J, Aloman C, Fiel M I, Munoz U, Kraus T, Lee T, Yee H F, Jr., Friedman S L: A novel murine model to deplete hepatic stellate cells uncovers their role in amplifying liver damage in mice. Hepatology 2013, 57(1):339-350.
10. Kisseleva T, Cong M, Paik Y, Scholten D, Jiang C, Benner C, Iwaisako K, Moore-Morris T, Scott B, Tsukamoto H et al: Myofibroblasts revert to an inactive phenotype during regression of liver fibrosis. Proc Natl Acad Sci USA 2012, 109(24):9448-9453.
11. Mederacke I, Hsu C C, Troeger J S, Huebener P, Mu X, Dapito D H, Pradere J P, Schwabe R F: Fate tracing reveals hepatic stellate cells as dominant contributors to liver fibrosis independent of its aetiology. Nat Commun 2013, 4:2823.
12. Guo C J, Pan Q, Cheng T, Jiang B, Chen G Y, Li D G: Changes in microRNAs associated with hepatic stellate cell activation status identify signaling pathways. FEBS J 2009, 276(18):5163-5176.
13. Maubach G, Lim M C, Chen J, Yang H, Zhuo L: miRNA studies in in vitro and in vivo activated hepatic stellate cells. World J Gastroenterol 2011, 17(22):2748-2773.
14. Lakner A M, Steuerwald N M, Walling T L, Ghosh S, Li T, McKillop I H, Russo M W, Bonkovsky H L, Schrum L W: Inhibitory effects of microRNA 19b in hepatic stellate cell-mediated fibrogenesis. Hepatology 2012, 56(1):300-310.
15. Miller E R, 3rd, Pastor-Barriuso R, Dalal D, Riemersma R A, Appel L J, Guallar E: Meta-analysis: high-dosage vitamin E supplementation may increase all-cause mortality. Ann Intern Med 2005, 142(1):37-46.
16. Lippman S M, Klein E A, Goodman P J, Lucia M S, Thompson I M, Ford L G, Parnes H L, Minasian L M, Gaziano J M, Hartline J A et al: Effect of selenium and vitamin E on risk of prostate cancer and other cancers: the Selenium and Vitamin E Cancer Prevention Trial (SELECT). JAMA 2009, 301(1):39-51.
17. Klein E A, Thompson I M, Jr., Tangen C M, Crowley J J, Lucia M S, Goodman P J, Minasian L M, Ford L G, Parnes H L, Gaziano J M et al: Vitamin E and the risk of prostate cancer: the Selenium and Vitamin E Cancer Prevention Trial (SELECT). JAMA 2011, 306(14):1549-1556.
18. Schuppan D, Kim Y O: Evolving therapies for liver fibrosis. J Clin Invest 2013, 123(5):1887-1901.
19. Corey K E, Rinella M E: Medical and Surgical Treatment Options for Nonalcoholic Steatohepatitis. Dig Dis Sci 2016.
20. Griffin T A, Anderson H C, Wolfe J H: Ex vivo gene therapy using patient iPSC-derived NSCs reverses pathology in the brain of a homologous mouse model. Stem Cell Reports 2015, 4(5):835-846.
21. Terai S, Tsuchiya A: Status of and candidates for cell therapy in liver cirrhosis: overcoming the "point of no return" in advanced liver cirrhosis. J Gastroenterol 2017, 52(2):129-140.
22. Matsumoto M, Hada N, Sakamaki Y, Uno A, Shiga T, Tanaka C, Ito T, Katsume A, Sudoh M: An improved mouse model that rapidly develops fibrosis in non-alcoholic steatohepatitis. Int J Exp Pathol 2013, 94(2):93-103.
23. Herrmann J, Gressner A M, Weiskirchen R: Immortal hepatic stellate cell lines: useful tools to study hepatic stellate cell biology and function?J Cell Mol Med 2007, 11(4):704-722.
24. Mederacke I, Dapito D H, Affo S, Uchinami H, Schwabe R F: High-yield and high-purity isolation of hepatic stellate cells from normal and fibrotic mouse livers. Nat Protoc 2015, 10(2):305-315.
25. Hamarneh S R, Kim B M, Kaliannan K, Morrison S A, Tantillo T J, Tao Q, Mohamed M M R, Ramirez J M, Karas A, Liu W et al: Intestinal Alkaline Phosphatase Attenuates Alcohol-Induced Hepatosteatosis in Mice. Dig Dis Sci 2017.
26. Younossi Z M, Koenig A B, Abdelatif D, Fazel Y, Henry L, Wymer M: Global Epidemiology of Non-Alcoholic Fatty Liver Disease-Meta-Analytic Assessment of Prevalence, Incidence and Outcomes. Hepatology 2015.
27. Geerts A: History, heterogeneity, developmental biology, and functions of quiescent hepatic stellate cells. Semin Liver Dis 2001, 21(3):311-335.
28. Yin C, Evason K J, Asahina K, Stainier D Y: Hepatic stellate cells in liver development, regeneration, and cancer. J Clin Invest 2013, 123(5):1902-1910.
29. Deleve L D, Wang X, Guo Y: Sinusoidal endothelial cells prevent rat stellate cell activation and promote reversion to quiescence. Hepatology 2008, 48(3):920-930.
30. Tijsen A J, van der Made I, van den Hoogenhof M M, Wijnen W J, van Deel E D, de Groot N E, Alekseev S, Fluiter K, Schroen B, Goumans M J et al: The microRNA-15 family inhibits the TGFbeta-pathway in the heart. Cardiovasc Res 2014, 104(1):61-71.
31. Ageilan R I, Calin G A, Croce C M: miR-15a and miR-16-1 in cancer: discovery, function and future perspectives. Cell Death Differ 2010, 17(2):215-220.
32. Klein U, Lia M, Crespo M, Siegel R, Shen Q, Mo T, Ambesi-Impiombato A, Califano A, Migliazza A, Bhagat G et al: The DLEU2/miR-15a/16-1 cluster controls B cell proliferation and its deletion leads to chronic lymphocytic leukemia. Cancer Cell 2010, 17(1):28-40.
33. Szabo G, Csak T: Role of MicroRNAs in NAFLD/NASH. Dig Dis Sci 2016.
34. Kim B M, Thier M C, Oh S, Sherwood R, Kanellopoulou C, Edenhofer F, Choi M Y: MicroRNAs are indispensable for reprogramming mouse embryonic fibroblasts into induced stem cell-like cells. PLoS One 2012, 7(6):e39239.
35. Kanellopoulou C, Muljo S A, Kung A L, Ganesan S, Drapkin R, Jenuwein T, Livingston D M, Rajewsky K: Dicer-deficient mouse embryonic stem cells are defective in differentiation and centromeric silencing. Genes Dev 2005, 19(4):489-501.
36. Kim B M, Choi M Y: Non-canonical microRNAs miR-320 and miR-702 promote proliferation in Dgcr8-deficient embryonic stem cells. Biochem Biophys Res Commun 2012, 426(2):183-189.
37. Betel D, Koppal A, Agius P, Sander C, Leslie C: Comprehensive modeling of microRNA targets predicts functional non-conserved and non-canonical sites. Genome Biol 2010, 11(8): R90.
38. Daneshvar K, Pondick J V, Kim B M, Zhou C, York S R, Macklin J A, Abualteen A, Tan B, Sigova A A, Marcho C et al: DIGIT Is a Conserved Long Noncoding RNA that Regulates GSC Expression to Control Definitive Endoderm Differentiation of Embryonic Stem Cells. Cell Rep 2016, 17(2):353-365.
39. Melhem A, Muhanna N, Bishara A, Alvarez C E, Ilan Y, Bishara T, Horani A, Nassar M, Friedman S L, Safadi R: Anti-fibrotic activity of N K cells in experimental liver injury through killing of activated HSC. J Hepatol 2006, 45(1):60-71.
40. Trang P, Wiggins J F, Daige C L, Cho C, Omotola M, Brown D, Weidhaas J B, Bader A G, Slack F J: Systemic delivery of tumor suppressor microRNA mimics using a neutral lipid emulsion inhibits lung tumors in mice. Mol Ther 2011, 19(6):1116-1122.
41. Wiggins J F, Ruffino L, Kelnar K, Omotola M, Patrawala L, Brown D, Bader A G: Development of a lung cancer therapeutic based on the tumor suppressor microRNA-34. Cancer Res 2010, 70(14):5923-5930.

The invention claimed is:

1. A method for treating or delaying progression of a disease associated with activated hepatic stellate cells (HSCs) in a subject, the method comprising in vivo administering to a subject who has, is suspected of having, or at risk of having a disease associated with activated HSCs a first composition comprising miR-412, a miR-412 mimic or a nucleic acid sequence encoding miR-412,
wherein the disease associated with activated hepatic stellate cells (HSCs) is selected from the group consisting of: liver fibrosis, alpha-1 antitrypsin deficiency, autoimmune hepatitis, biliary atresia, cirrhosis, nonalcoholic fatty liver disease (NAFLD), hepatic cancer, hepatic fibrosis, hepatic steatosis (fatty liver disease), Gilbert's syndrome, hemochromatosis, lysosomal acid lipase deficiency, primary biliary cholangitis, sarcoidosis, toxic hepatitis, tyrosinemia, viral hepatitis A, viral hepatitis B, viral hepatitis C, and Wilson disease.

2. The method of claim 1, wherein the disease associated with activated HSCs is NAFLD or hepatotoxicity.

3. The method of claim 1, wherein the first composition further comprises miR-15a, a miR-15a mimic or a nucleic acid sequence encoding miR-15a.

4. The method of claim 1, further comprising, after administering, a step of administering a second composition comprising miR15a or nucleic acid encoding miR15a.

5. The method of claim 1, wherein the first composition further comprises a pharmaceutically acceptable carrier.

6. The method of claim 1, further comprising, prior to administering, a step of diagnosing the subject as having or at risk of having a disease associated with activated HSCs.

7. The method of claim 1, wherein the administration is repeated at least once.

8. The method of claim 1, wherein the subject is a mammal.

9. The method of claim 1, wherein the subject is a human.

10. The method of claim 1, wherein the first composition is administered via direct injection, intra-hepatic injection, i.v. administration, or parenteral administration.

11. A method for treating or delaying progression of a disease associated with activated HSCs in a subject, the method comprising in vivo administering to a subject who has, is suspected of having, or at risk of having a disease associated with activated HSCs a first composition comprising miR-15a, a miR-15a mimic or a nucleic acid sequence encoding miR-15a,
wherein the disease associated with activated hepatic stellate cells (HSCs) is selected from the group consisting of: liver fibrosis, alpha-1 antitrypsin deficiency, autoimmune hepatitis, biliary atresia, cirrhosis, nonalcoholic fatty liver disease (NAFLD), hepatic cancer, hepatic fibrosis, hepatic steatosis (fatty liver disease), Gilbert's syndrome, hemochromatosis, lysosomal acid lipase deficiency, primary biliary cholangitis, sarcoidosis, toxic hepatitis, tyrosinemia, viral hepatitis A, viral hepatitis B, viral hepatitis C, and Wilson disease.

12. The method of claim 11, wherein the disease associated with activated HSCs is NAFLD or hepatotoxicity.

13. The method of claim 11, further comprising, after administering, a step of administering a second composition comprising miR-412, a miR-412 mimic or a nucleic acid sequence encoding miR-412.

14. The method of claim 11, wherein the first composition further comprises a pharmaceutically acceptable carrier.

15. A method for treating or delaying progression of a disease associated with activated HSCs in a subject, the method comprising in vivo administering to a subject who has, is suspected of having, or at risk of having a disease associated with activated HSCs (a) a composition comprising miR-15a, a miR-15a mimic or a nucleic acid sequence encoding miR-15a, and (b) a composition comprising miR-412, a miR-412 mimic or a nucleic acid sequence encoding miR-412, wherein the disease associated with activated hepatic stellate cells (HSCs) is selected from the group consisting of: liver fibrosis, alpha-1 antitrypsin deficiency, autoimmune hepatitis, biliary atresia, cirrhosis, nonalcoholic fatty liver disease (NAFLD), hepatic cancer, hepatic fibrosis, hepatic steatosis (fatty liver disease), Gilbert's syndrome, hemochromatosis, lysosomal acid lipase deficiency, primary biliary cholangitis, sarcoidosis, toxic hepatitis, tyrosinemia, viral hepatitis A, viral hepatitis B, viral hepatitis C, and Wilson disease.

16. The method of claim 15, wherein the composition of (a) is administered at substantially the same time as the composition of (b).

* * * * *

SEQUENCE LISTING

```
<160> NUMBER OF SEQ ID NOS: 17

<210> SEQ ID NO 1
<211> LENGTH: 91
<212> TYPE: DNA
<213> ORGANISM: Homo sapiens

<400> SEQUENCE: 1
ctggggtacg gggatggatg gtcgaccagt tggaaagtaa ttgtttctaa tgtacttcac      60
ctggtccact agccgtccgt atccgctgca g                                     91
```

<210> SEQ ID NO 2
<211> LENGTH: 80
<212> TYPE: DNA
<213> ORGANISM: Mus musculus

<400> SEQUENCE: 2
gggtatggga cggatggtcg accagctgga aagtaattgt ttctaatgta cttcacctgg      60
tccactagcc gtcggtgccc                                                  80

<210> SEQ ID NO 3
<211> LENGTH: 80
<212> TYPE: DNA
<213> ORGANISM: Equus caballus

<400> SEQUENCE: 3
gggtacagga gggatggtcg accagttgga aagtaattgt ttctaatgta cttcacctgg      60
tccactagcc gtccgtaccc                                                  80

<210> SEQ ID NO 4
<211> LENGTH: 124
<212> TYPE: DNA
<213> ORGANISM: Ovis aries

<400> SEQUENCE: 4
agggaagaac gtcagtacca gcaaccactc tggggtacag gacggatggt cgaccagttg      60
gaaagtaatt gtttctaatg tacttcacct ggtccactag ctgtccgtac ccactgcagc     120
ctgc                                                                  124

<210> SEQ ID NO 5
<211> LENGTH: 90
<212> TYPE: DNA
<213> ORGANISM: Pan troglodytes

<400> SEQUENCE: 5
tggggtacgg ggatggatgg tcgaccagtt ggaaagtaat tgtttctaat gtacttcacc      60
tggtccacta gccgtccgta tccgctgcag                                       90

<210> SEQ ID NO 6
<211> LENGTH: 91
<212> TYPE: DNA
<213> ORGANISM: Macaca mulatta

<400> SEQUENCE: 6
ctggggtacg gggatggatg gtcgaccagt tggaaagtaa ttgtttctaa tgtacttcac      60
ctggtccact agccgtccgt atccgctgca g                                     91

<210> SEQ ID NO 7
<211> LENGTH: 90
<212> TYPE: DNA
<213> ORGANISM: Bos taurus

<400> SEQUENCE: 7
ctggggtaca ggacggatgg tcgaccagtt ggaaagtaat tgtttctaat gtacttcacc      60
tggtccacta gctgtccgta cccactgcag                                       90

<210> SEQ ID NO 8
<211> LENGTH: 122
<212> TYPE: DNA

-continued

<213> ORGANISM: Capra hircus

<400> SEQUENCE: 8
agggaagaac gtcagtacca gcaaccactc gggtacagga cggatggtcg accagttgga    60
aagtaattgt ttctaatgta cttcacctgg tccactagct gtccgtaccc actgcagcct   120
gc                                                                  122

<210> SEQ ID NO 9
<211> LENGTH: 70
<212> TYPE: DNA
<213> ORGANISM: Rattus norvegicus

<400> SEQUENCE: 9
gggacggatg gtcgaccagc tggaaagtaa ttgtttctaa tgtacttcac ctggtccact    60
agccgtcggt                                                           70

<210> SEQ ID NO 10
<211> LENGTH: 83
<212> TYPE: DNA
<213> ORGANISM: Homo sapiens

<400> SEQUENCE: 10
ccttggagta aagtagcagc acataatggt ttgtggattt tgaaaaggtg caggccatat    60
tgtgctgcct caaaaataca agg                                            83

<210> SEQ ID NO 11
<211> LENGTH: 84
<212> TYPE: DNA
<213> ORGANISM: Mus musculus

<400> SEQUENCE: 11
cccttggagt aaagtagcag cacataatgg tttgtggatg ttgaaaaggt gcaggccata    60
ctgtgctgcc tcaaaataca agga                                           84

<210> SEQ ID NO 12
<211> LENGTH: 57
<212> TYPE: DNA
<213> ORGANISM: Equus caballus

<400> SEQUENCE: 12
tagcagcaca taatggtttg tggattttga aaaggtgcag gccatattgt gctgcct       57

<210> SEQ ID NO 13
<211> LENGTH: 59
<212> TYPE: DNA
<213> ORGANISM: Canis lupus

<400> SEQUENCE: 13
tagcagcaca taatggtttg tggattttga aaaggtgcag gccatattgt gctgcctca    59

<210> SEQ ID NO 14
<211> LENGTH: 83
<212> TYPE: DNA
<213> ORGANISM: Pan troglodytes

<400> SEQUENCE: 14
ccttggagta aagtagcagc acataatggt ttgtggattt tgaaaaggtg caggccatat    60
tgtgctgcct caaaaataca agg                                            83

```
<210> SEQ ID NO 15
<211> LENGTH: 83
<212> TYPE: DNA
<213> ORGANISM: Macaca mulatta

<400> SEQUENCE: 15
ccttggagta aagtagcagc acataatggt ttgtggattt tgaaaaggtg caggccatat        60
tgtgctgcct caaaaataca agg                                               83

<210> SEQ ID NO 16
<211> LENGTH: 83
<212> TYPE: DNA
<213> ORGANISM: Bos taurus

<400> SEQUENCE: 16
ccttggagta aagtagcagc acataatggt ttgtggattt tgaaaaggtg caggccatat        60
tgtgctgcct caaaaataca agg                                               83

<210> SEQ ID NO 17
<211> LENGTH: 95
<212> TYPE: DNA
<213> ORGANISM: Capra hircus

<400> SEQUENCE: 17
accttggagt aaagtagcag cacataatgg tttgtggatt ttgaaaaggt gcaggccata        60
ttgtgctgcc tcaaaaatac aaggatctga tcttc                                  95
```